US012037652B2

United States Patent
Gao et al.

(10) Patent No.: US 12,037,652 B2
(45) Date of Patent: Jul. 16, 2024

(54) METHODS OF IDENTIFYING DHA CANOLA NS-B50027-4

(71) Applicant: Nuseed Pty Ltd, Laverton North (AU)

(72) Inventors: Wenxiang Gao, Rocklin, CA (US);
Yonghe Bai, Sacramento, CA (US);
Tina Ngo, Stockton, CA (US)

(73) Assignee: NUSEED NUTRITIONAL AUSTRALIA PTY LTD, Laverton North (AU)

( * ) Notice: Subject to any disclaimer, the term of this patent is extended or adjusted under 35 U.S.C. 154(b) by 799 days.

(21) Appl. No.: 17/198,064

(22) Filed: Mar. 10, 2021

(65) Prior Publication Data

US 2021/0198757 A1    Jul. 1, 2021

Related U.S. Application Data

(63) Continuation-in-part of application No. PCT/US2019/050243, filed on Sep. 9, 2019.

(60) Provisional application No. 62/839,482, filed on Apr. 26, 2019, provisional application No. 62/729,805, filed on Sep. 11, 2018, provisional application No. 63/126,360, filed on Dec. 16, 2020.

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/13* (2013.01)

(58) Field of Classification Search
None
See application file for complete search history.

(56) References Cited

U.S. PATENT DOCUMENTS

| 10,563,218 B2 | 2/2020 | Devine et al. |
| 10,570,405 B2 | 2/2020 | Devine et al. |
| 2018/0016590 A1 | 1/2018 | Devine et al. |
| 2018/0016591 A1 | 1/2018 | Devine et al. |

FOREIGN PATENT DOCUMENTS

| WO | 2005/021761 A1 | 3/2005 | |
| WO | 2013/185184 A2 | 12/2013 | |
| WO | 2017/218969 A1 | 12/2017 | |
| WO | 2017/219006 A1 | 12/2017 | |
| WO | WO-2017219006 A1 * | 12/2017 | ............... A01H 5/10 |
| WO | 2018/165350 A1 | 9/2018 | |
| WO | 2020/055763 A1 | 3/2020 | |

OTHER PUBLICATIONS

European Search Report issued in EP Application No. 19858886.5 dated Jun. 5, 2022.
International Search Report and Written Opinion received for PCT Patent Application No. PCT/US2019/050243, mailed on Dec. 2, 2019, 7 pages.
Napier, et al. "Update on GM Canola Crops as Novel Sources of Omega-3 Fish Oils", Plant Biotechnology Journal, vol. 17, 2018, pp. 703-705.

* cited by examiner

*Primary Examiner* — Aaron A Priest
(74) *Attorney, Agent, or Firm* — Wiley Rein LLP

(57) ABSTRACT

The present embodiments provide compositions, methods and primers for detecting DNA of genetically modified canola, specifically of elite event DHA canola NS-B50027-4 and progeny thereof.

17 Claims, 22 Drawing Sheets

Specification includes a Sequence Listing.

FIG. 2A

```
         A02-282 forward primer
CTGATTCTCCCGTTCGAC TCAGATCTTCGAAGCCTCGG TCCCAGTCGCTCCTCTCCGCCCGATCACTTCTCC
CACTAACACCCCGGCCAAGCCTTCCCGGCAGCCTCACCCGCCCCCCCTACTCAACAGG  TER_Linus-Cnl2

GCCCCCAACAAGGCTTGTAGTTAATAAGGATTCATTTCAGGCGATTGCATTCCGGGCAGTAGCAGTATATCTATTA
CGCGGTTGCTTCCGAACACATATTATCCTTAACACTAAGTCCTAACATAATCATCATTAATTATATCATAAT  TER_Linus-Cnl2

GTATACAGAACCTCTTATTTAGCTAAAAGCATTATGTTCTTAATGTTGATAAGAAGTTGAGAAACAATATAATTGAGCT
CATATGTCTTCGGAGAATAAATCGATTTTCGTAATACAAGAATTACTAAGAATTCTTCAAACTCTTGTTTATTAACTCGA  Brassica napus chromosome A2 downstream
Brassica napus HPP gene 3' UTR TCTGATTAGTTGATCGTAATTGGTCATTAATTGGTCAGTATGTCTAACCAGTGGTCACCTATAAGACCGTATAAGAGACATCTCAAA
AGACTAATCAACTAGCATTAACACTAATTAACAGTAATATTATTAACCAGTCCATTCGTCACGTCATATCTCGATATTCTCCGAGAGTTT  Brassica napus chromosome A2 downstream
                                                                   A02-282 reverse primer
```

FIG. 5A

| 1 | CTCCGCCGCC AACAAGGCTT GTAGTTAATA GGAATCATTC AGGGATTGTG |
| --- | --- |
| | 5'-A02dn2 forward-3' →    5'-A02dn2 probe-3' → |
| 51 | ATTCCGGGCA GTAGTAATTA ATAATATAGT ATTAGTATAC AGAACCTCTT |
| | 5'-A02dn2 probe-3' → |
| 101 | ATTTAGCTAA AAGATTATGT TCTTAATGTT GATAAGAAGT TTGAGAAACA |
| 151 | AATATAATTG AGCTTCTGAT TAGTTGATCG TAATTGGTC |
| | 3' TTAAC TCGAAGACTA ATCAACTAGC A 5' |
| | ← 3'-A02dn2 reverse-5' |

FIG. 5B

| 1 | TTTTCGTCGA GTTGCTGAAA CTGGACCCAA GCCAGTGTAC GGCGCAGGAG |
| --- | --- |
| 51 | GTACTTTAAG CTTATAACCC TTTGTCTATC CTTTGGCTAG CGGCTAATGT |
| | 5'-A05up2 forward-3' → |
| 101 | TGATGAACTT TTTTATTCAA CCGTTGGCTA AGGTAACACT GATAGTTTAA |
| | 5'-A05up2 probe-3' → |
| 151 | ACTGAAGGCG GGAAACGACA ATCTGCTAGT GGATCTCCCA GTCACGACGT |
| | 3'ACGATCA CCTAGAGGGT CAGT5' |
| | ← 3'-A05up2 reverse-5' |
| 201 | TGTAAAACGG GCGCCCGCG GAAAGC |

FIG. 7
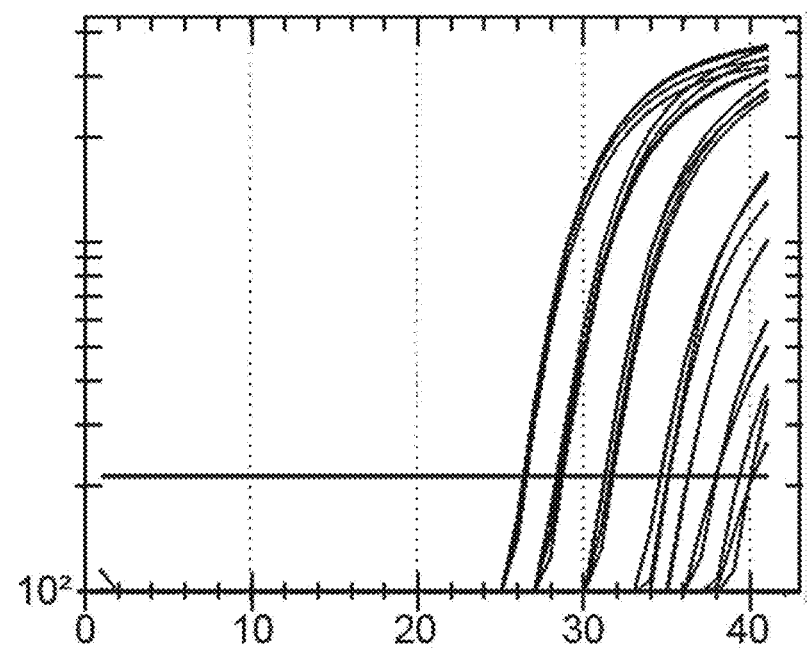
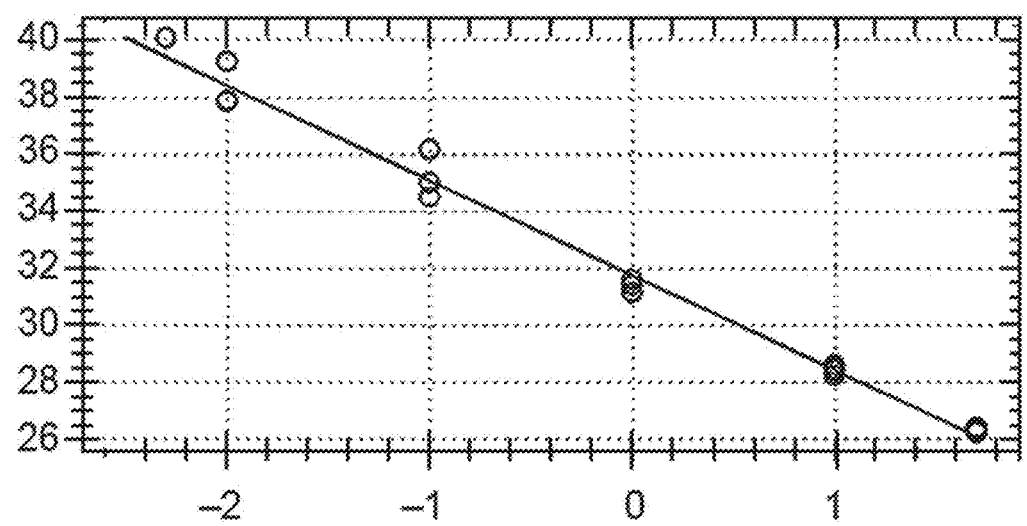

FIG. 20
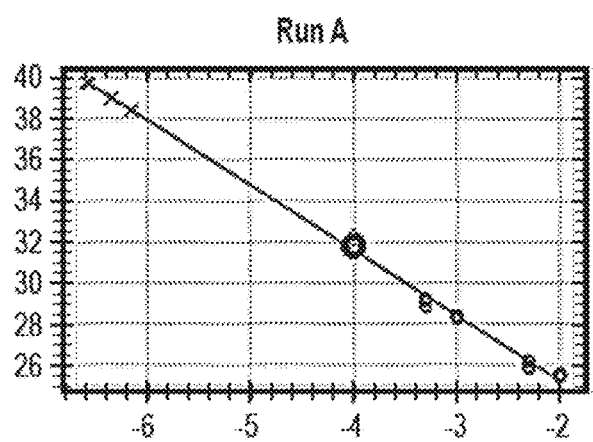
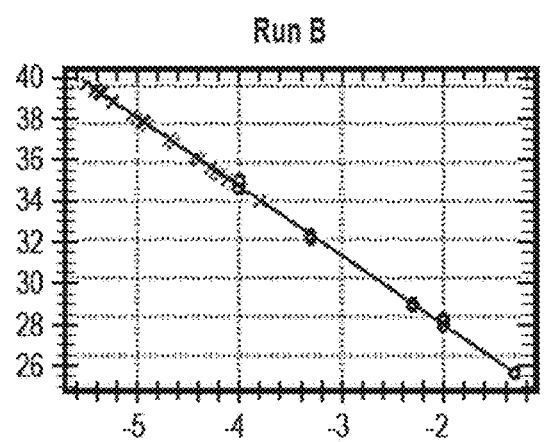
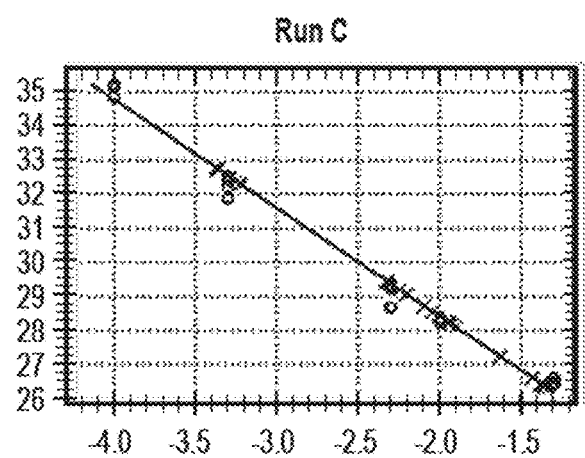
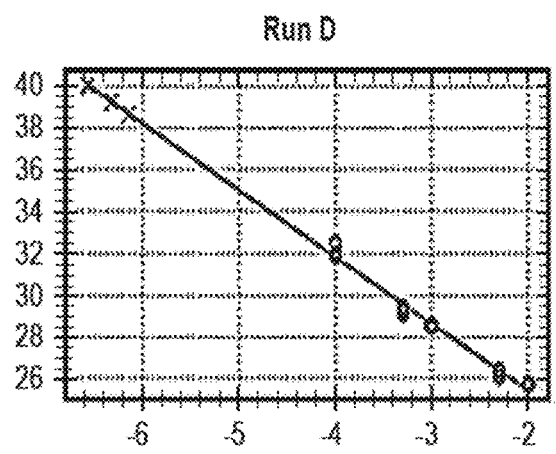

FIG. 21
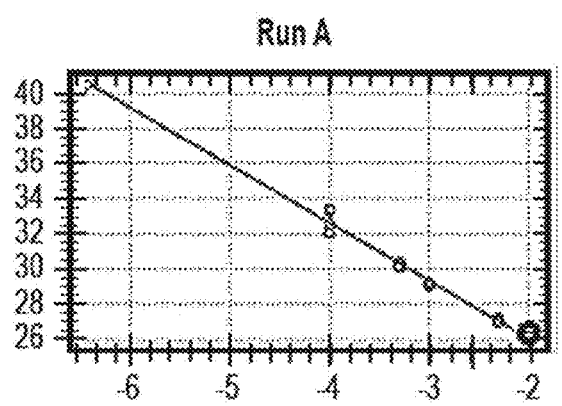
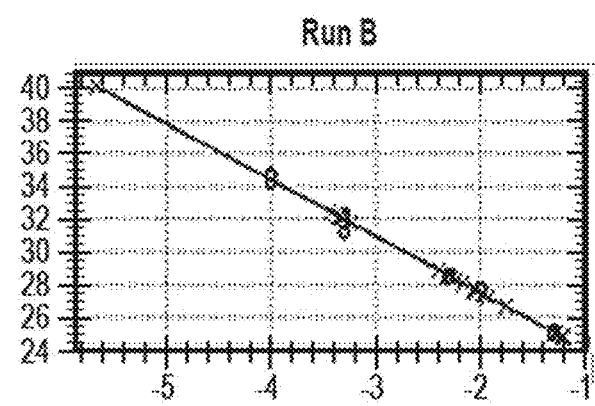
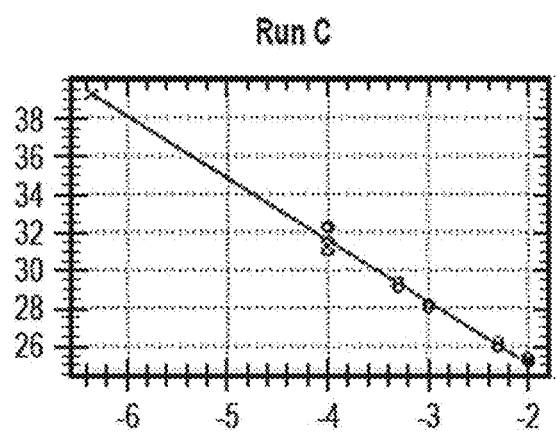
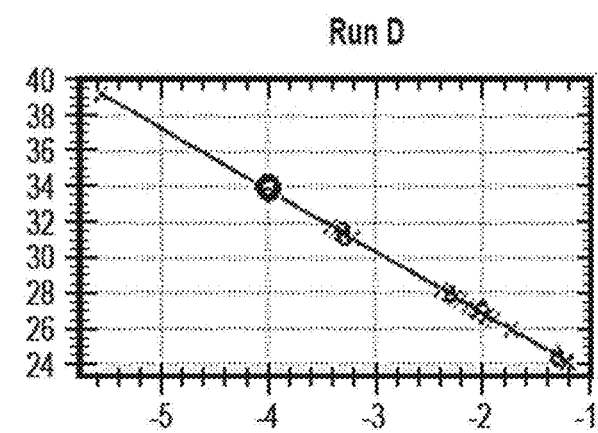

FIG. 22
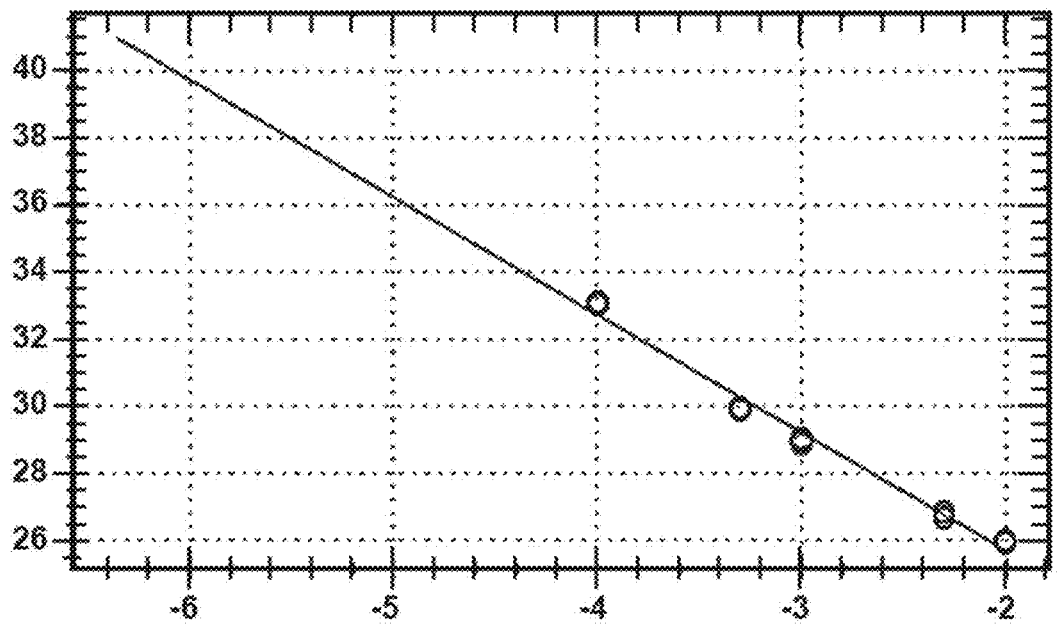
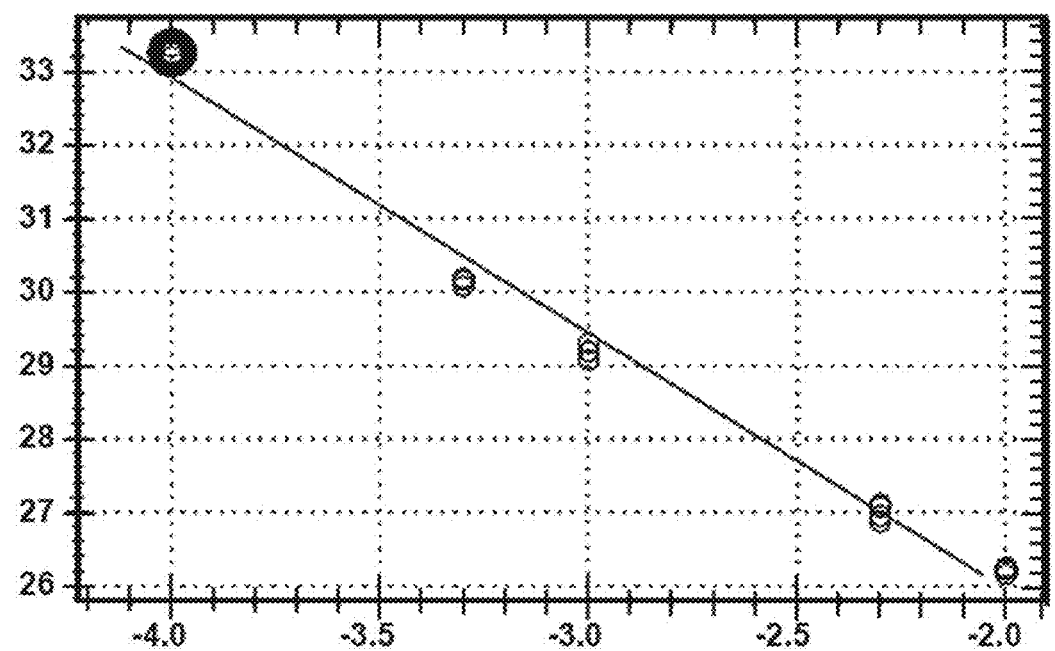

FIG. 23

ACAAGCCTTGTTGGCGGCGGAGAAGTGATCGGCGCGGCGAGAAGCAGCGG
TGTTCGGAACAACCGCCGCCTCTCACTAGCCGCGCCGCTCTTCGTCGCC

ACTCGGAGACGAGGCCTTGGAAGATCTGAGTCGAACGGGCGGTACCGCGG
TGAGCCTCTGCTCCGGAACCTTCTAGACTCAGCTTGCCCGCCATGGCGCC

CCGCAAGCTTTCCGCGGGGCGCCCGTTTTACAACGTCGTGACTGGGAGAT
GGCGTTCGAAAGGCGCCCCGCGGGCAAAATGTTGCAGCACTGACCCTCTA

CCACTAGCAGATTGTCGTTTCCCGCCTTCAGTTTAAACTATCAGTGTTTG
GGTGATCGTCTAACAGCAAAGGGCGGAAGTCAAATTTGATAGTCACAAAC

AAGGACAGACCCACCCAAGAACACACCAGTCATTCAGATGCAGCCTATCT
TTCCTGTCTGGGTGGGTTCTTGTGTGGTCAGTAAGTCTACGTCGGATAGA

CCGTGCCGGCTATTCCAGCTGATGAGTTGAAGGATATAACTGATAACTAT
GGCACGGCCGATAAGGTCGACTACTCAACTTCCTATATTGACTATTGATA

GGTTCCAAGTCCTTGATTGGTGAGGGCTCTTATGGAAGAGTGTTTTACGG
CCAAGGTTCAGGAACTAACCACTCCCGAGAATACCTTCTCACAAAATGCC

TGTTCTTAGAAGCGGCAAGGCAGCTGCCATTAAGAAGCTGGATTCTAGTA-3'
ACAAGAATCTTCGCCGTTCCGTCGACGGTAATTCTTCGACCTAAGATCAT-5'

FIG. 24

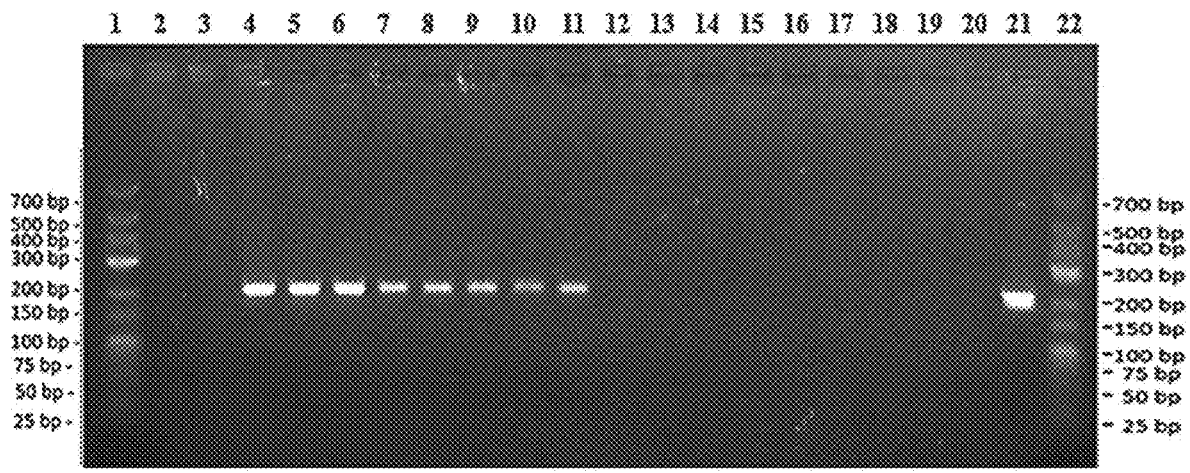

METHODS OF IDENTIFYING DHA CANOLA NS-B50027-4

RELATED APPLICATIONS

This Application is a continuation-in-part of application No. PCT/US2019/050243, filed Sep. 9, 2019, which claims the priority benefit of U.S. Patent Applications No. 62/839,482, filed Apr. 26, 2019, and No. 62/729,805, filed Sep. 11, 2018, each of which is incorporated herein by reference in its entirety for all purposes. This Application also claims the priority benefit of U.S. Patent Application No. 63/126,360, filed Dec. 16, 2020, which is incorporated herein by reference in its entirety for all purposes.

SEQUENCE LISTING

This Specification contains DNA sequences identified in a Sequence Listing entitled "Methods of Identifying DHA Canola NS-B50027-4," 10,684 bytes, created Feb. 22, 2021, submitted in ASCII format via EFS-Web, which is incorporated herein by reference in its entirety for all purposes.

BACKGROUND

Long chain omega-3 (LC-ω3) fatty acids such as docosahexaenoic acid (DHA) provide many health benefits, and can be included in human diets, e.g., by consuming algae-derived products or algae-eating fish. Alternative sources for LC-ω3 fatty acids are needed to satisfy increased human consumption needs. A genetically modified canola line, DHA canola NS-B50027-4, accumulates a significant concentration of DHA in canola seed. There remains a need for efficient identification of NS-B50027-4, e.g., for plant stewardship purposes.

SUMMARY

The present embodiments provide compositions, methods and primers to identify DHA canola NS-B50027-4 and progeny thereof.

One embodiment provides an agarose gel electrophoresis-based method to qualitatively detect the presence (or absence) of the Nuseed DHA Canola NS-B50027-4 event. More specifically, two event-specific PCR assays targeting the T-DNA insertion junction sites in the canola genome can be used for adventitious presence testing, trait purity testing, and trait introgression, and to support DHA Canola NS-B50027-4 plant stewardship.

One embodiment provides an event-specific Taqman-based quantitative detection method for identifying the Nuseed DHA canola NS-B50027-4 event. The event-specific Taqman assays targeting the T-DNA insertion junction sites in the canola genome from this study can be used for adventitious presence testing, low level presence (LLP) testing, trait purity testing, and trait introgression, and to support DHA Canola NS-B50027-4 plant stewardship.

BRIEF DESCRIPTION OF THE DRAWINGS

FIG. 2A shows primer locations (boxed) for assay A02-282, the transgene junction on NS-B50027-4 chromosome A02 (SEQ ID NO:24): A02-282 forward primer (SEQ ID NO:5) and A02-282 reverse primer (SEQ ID NO:6).

FIG. 5A is a scheme showing the transgene junction region in chromosome A02 (SEQ ID NO:9) with the locations of primer 5'A02dn2 forward-3' (SEQ ID NO:15), primer 3'-A02dn2 reverse-5' (SEQ ID NO:16), and probe 5'-A02dn2 probe-3' (SEQ ID NO:17). FIG. 5B is a scheme showing the transgene junction region in chromosome A05 (SEQ ID NO:10) with the locations of primer 5'-A05up2 forward-3' (SEQ ID NO:12), primer 3'-A05up2 reverse-5' (SEQ ID NO:13), and probe 5'A05up2 probe-3' (SEQ ID NO:14). Primer sequences are highlighted in light gray and probe sequences in medium gray. Sequences in dark gray indicate the complementary sequences of the reverse primers shown below it.

FIG. 7 is a diagram reflecting the amplification plot (top panel, RFU per Cycles) and standard curve (bottom panel, Cq over Log Starting Quantity) from A05up2 event-specific assay with the standard DNA samples and the controls. The R square value of the standard curve was 0.989 and the slope −3.323 for A05up2.

FIG. 8 shows primer locations (boxed) for primers A02-258F (SEQ ID NO:20) and A02-258R (SEQ ID NO:21), for the transgenic junction on chromosome A02 (SEQ ID NO:26) for assay A02-258.

FIG. 9 shows primer locations (boxed) for primers A05-200F (SEQ ID NO:18) and A05-200R (SEQ ID NO:19) for the transgenic junction on chromosome A05 (SEQ ID NO:27) for assay A05-200.

FIG. 20 shows standard curves (y-axis: Cq; x-axis: log starting quantity) from runs A (R square 0.986, slope −3.187), B (R square 0.998, slope 3.596), C (R square 0.989, slope −3.178), and D (R square 0.985, slope 3.194) with an A02Dn2 event-specific assay using different GM spiked DNA samples.

FIG. 21 shows standard curves (y-axis: Cq; x-axis: log starting quantity) from runs A (R square 0.983, slope −3.278), B (R square 0.994, slope −3.453), C (R square 0.982, slope −3.254), and D (R square 0.996, slope −3.475), with A05up2 event-specific assay using different GM spiked DNA samples.

FIG. 22 shows standard curves (y-axis: Cq; x-axis: log starting quantity) from two runs of a HMG assay using five different DNA contents in each reaction. Top panel R square 0.988, slope −3.491; bottom panel R square 0.988, slope −3.479.

FIG. 23 shows primer locations for the primers used as described herein to identify the event NS-B50027-4 transgenic junction on chromosome A05. Primers A05-216F and A05-216R (SEQ ID NO:28 and SEQ ID NO:29, respectively), underlined with arrows indicating direction; transgenic insert DNA, bold; *Brassica* DNA, normal text. The (+) strand of this junction region is also provided as SEQ ID NO:30.

FIG. 24 is a gel image from a qualitative event-specific assay (A05-216) for a 216-bp amplicon of AV Jade (negative control), no template control (NTC) samples, six different DHA canola NS-B50027-4 spike levels and eight conventional Nuseed canola lines. The 216-bp amplicon was unique to DHA canola NS-B50027-4.

DETAILED DESCRIPTION

Figure 1:
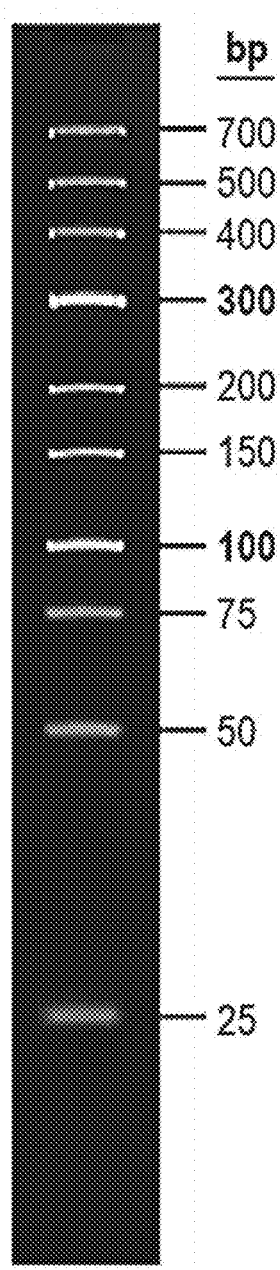
FIG. 1 is an image of a gel showing GeneRuler low range DNA ladder. More specifically, Thermo Scientific™ GeneRuler™ Low Range DNA Ladder, ready-to-use, contains a mix of ten chromatography-purified individual DNA fragments (in base pairs): 700, 500, 400, 300, 200, 150, 100, 75, 50, 25

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list.

All values are approximate as there is some fluctuation in fatty acid composition due to environmental conditions. Values are typically expressed as percent by weight of total fatty acid, or percent weight of the total seed. Accordingly, other than in the operating examples, or where otherwise indicated, all numbers expressing quantities or reaction conditions used herein should be understood as modified in all instances by the term "about."

NS-B50027-4 DHA canola was generated, inter alia, via *Agrobacterium tumefaciens*-mediated transformation of canola cultivar AV Jade with a binary vector designated pJP3416_GA7-ModB. Vector pJP3416_GA7-ModB was designed specifically to convert oleic acid to DHA in canola seed, and contains expression cassettes for seven microalgae and yeast transgenes (abbreviated Micpu-Δ6D, Pyrco-Δ5E, Pavsa-Δ5D, Picpa-ω3D, Pavsa-Δ4D, Lackl-Δ12D and Pyrco-Δ6E) involved in the DHA biosynthesis pathway (and for the herbicide selection gene PAT). Each transgene has its own expression cassette including seed-specific promoter, enhancer and terminator. See U.S. Pat. Nos. 10,563,218 and 10,570,405.

NS-B50027-4 DHA canola was characterized with vector-targeted sequencing, whole-genome sequencing and Polymerase Chain Reaction (PCR)-amplicon sequencing. Sequencing data indicated that the DHA canola contained no vector backbone, no binary vector bacterial selectable marker gene Neomycin Phosphotransferase II (NPT II) or any *A. tumefaciens* genome sequence. Sequencing information also indicated that DHA canola contained two T-DNA inserts, one on chromosome A02 (partial insert) and the other on chromosome A05 (two full inserts arranged in a palindrome). The full genomic DNA sequences of the two T-DNA inserts were verified and the sequence of each T-DNA insert perfectly matched the reference of vector pJP3416_GA7-ModB. Both transgenic inserts were required to accumulate about 10% DHA in canola seed. See U.S. Pat. Nos. 10,563,218 and 10,570,405.

More specifically, the A02 T-DNA insertion is a partial insert, containing complete gene expression cassettes for genes Micpu-Δ6D, Pyrco-Δ5E, Pavsa-Δ5D and Picpa-ω3D but not for genes Pavsa-Δ4D, Lackl-Δ12D, Pyrco-Δ6E and PAT. The sequence of the A02 T-DNA insert otherwise matches the reference of vector pJP3416_GA7-ModB. The A02 T-DNA insert replaced 15 bp DNA (GTAGCACGACAAGTT) (SEQ ID NO:1) from the *B. napus* genome, and is located within the 3' UTR of a hypothetical protein gene on chromosome A02. The A05 T-DNA insertion contains two T-DNA transgene sets from the binary vector that formed a palindromic structure in the right border-transgenes-left border:left border-transgenes-right border orientation. The sequence of the A05 T-DNA insert also matches the reference sequence in vector pJP3416_GA7-ModB. The A05 T-DNA insert replaced 20 bp DNA (CACGGTGGAGGTCACCATGT) (SEQ ID NO:2) from the *B. napus* genome, and is located within the second exon of a Pto-Interacting (PTI) gene on chromosome A05.

The present embodiments provide compositions, methods and DNA sequences (e.g., primers) for the relatively easy identification of the Nuseed DHA canola NS-B50027-4 event. More specifically, the present embodiments provide two event specific detection methods. In particular, for example, specific primers complementary to the junction region of each transgene insertion site are used to generate DNA fragments that can be identified using gel electrophoresis. In particular, for example, specific primers are used in a Taqman assay. These two detection methods are new, efficient, sensitive, and accurate for detecting Nuseed DHA canola NS B50027-4 event.

Event-specific gel-based assay, targeting an insert in DHA canola NS-B50027-4 on chromosomes A05 and A02 have been successfully developed and validated. The HMG reference gene PCR profile was designed to confirm the PCR ability of DNA sample.

The Limit of Detection (LOD) of the event-specific assay is determined at least 0.05% NS-B50027-4 DNA to total DNA, or less than 50 genome copies. The specificity of the assay was validated by testing 27 CRM materials available from AOCS and 7 different Nuseed non-GM conventional oilseeds varieties.

In addition, the present embodiments also provide a qualitative detection method for determining the presence of DHA Canola (Event NS-B50027-4) in oilseeds DNA sample. The assay can be used for adventitious presence testing, trait purity testing, and trait introgression, and to support DHA Canola NS-B50027-4 regulatory submission and commercialization. See also WO 2020/055763.

EXAMPLES

Example 1. Gel Electrophoresis-Based A02-282 and A05-286 Assays for Detection of the Transgenic Event in DHA Canola NS-B50027-4

T7 generation DHA canola NS-B50027-4 seed was obtained from two test plots. Comparator seed included Nuseed non-GMO canola germplasm as listed and described in Tables 3, 4 and 5, and Johnny's Dwarf Essex Rape seed. AV Jade and Essex Rape were used as negative controls. Certified Reference materials (CRM): Twenty-seven CRM from American Oil Chemists' Society (AOCS) are listed in Table A:

TABLE A

List of CRM

| Certified Reference materials from AOCS (American Oil Chemists' Society) | Sample ID |
|---|---|
| Canola Events: | |
| 0306B4-Canola Bayer CropScience Non-Modified Leaf DNA | AOCS-1 |
| 0711D3-Canola Bayer CropScience Event Topas 19/2 Leaf DNA | AOCS-2 |
| 0208A5-Canola Bayer CropScience Event T45 Genomic DNA Leaf Tissue | AOCS-3 |
| 0711C2-Canola Bayer CropScience Event Rf2 Leaf DNA | AOCS-4 |
| 0711B2-Canola Bayer CropScience Event Rfl Leaf DNA | AOCS-5 |
| 0306F6-Canola Bayer CropScience Event Ms8 Leaf DNA | AOCS-6 |
| 0711A3-Canola Bayer CropScience Event Ms1 Leaf DNA | AOCS-7 |
| 0306G5-Canola Bayer Crop Science Event Rf3 Leaf DNA | AOCS-8 |
| Soybean Events: | |
| 0906B-Soybean Monsanto Company Event MON89788 | AOCS-9 |
| 0809B-Soybean Monsanto Company Event MON87769 | AOCS-10 |
| 0311A-Soybean Monsanto Company Event MON87708 | AOCS-11 |
| 0210A-Soybean Monsanto Company Event MON87705 | AOCS-12 |
| 0809A-Soybean Monsanto Company Event MON87701 | AOCS-13 |
| 0610A3-Soybean Bayer CropScience Event FG72 Leaf DNA | AOCS-14 |
| 0707C6-Soybean Bayer CropScience Event A5547-127 Leaf DNA | AOCS-15 |
| Maize Events: | |
| 0407B-Maize Syngenta Event GA21 | AOCS-16 |
| 0906E-Maize Monsanto Company Event MON89034 | AOCS-17 |
| 0607A2-Maize Syngenta Event MIR604 | AOCS-18 |
| 0406D-Maize Monsanto Company Event MON88017 | AOCS-19 |
| 0512A-Maize Monsanto Company Event MON87427 | AOCS-20 |
| 0709A-Maize Monsanto Company Event MON87460 | AOCS-21 |
| 0306H9-Maize Bayer CropScience Event T25 DNA | AOCS-22 |
| Cotton Events: | |
| 0804D-Cotton Monsanto Company Event MON15985-7 | AOCS-23 |
| 0804C-Cotton Monsanto Company Event MON531 | AOCS-24 |
| 0804B-Cotton Monsanto Company Event MON1445 | AOCS-25 |
| 0306A3-Cotton Bayer CropScience Non-Modified Leaf DNA | AOCS-26 |
| 1108A5-Cotton Bayer CropScience Event GHB 614 Leaf DNA | AOCS-27 |

DNAs were extracted from seeds using a cetyl tri methyl ammonium bromide (CTAB) DNA extraction method briefly described as follows:

Step 1: Grind 3000 seeds per sample completely and transfer powder to 50 ml Falcon tubes. Clean grinder thoroughly between samples to prevent cross-contamination.

Step 2: Add 30 ml of 1× CTAB Extraction Buffer (100 CTAB, 50 mM Tris-HCl pH 8.0, 10 mM EDTA pH 8.0) and mix thoroughly by shaking and inverting the tube several times.

Step 3: Incubate the samples in 55-60° C. (e.g., 57.5° C.) water-bath for 1 hr. Mix the samples every 10 min by lightly inverting the tubes. After the incubation, allow the samples cool to room temperature.

Step 4: Centrifuge the samples for 2 min at 3000 g. Carefully remove as much as possible the top layer, which is oil, using pipet. The light brown middle layer contains DNA. Centrifuge the samples again for 10 min at 3000 g.

Step 5: For each sample, transfer 900 μl of the middle layer to a 2 ml centrifuge tube, add 900 μl chloroform under a fume hood. Mix the samples vigorously for 5 min. Centrifuge the samples for 5 min at 13000 g.

Step 6: Transfer 750 μl of the supernatant to a new 2.0 ml centrifuge tube, add 750 μl 1X CTAB Buffer and mix by inverting the tubes 10-15 times. Rest the samples at room temperature for 5 min. Centrifuge the samples at 13000 g for 7 min. Discard the supernatant.

Step 7: Add 250 μl 1M NaCl solution containing RNase A (final concentration 20 pg/ml) to each sample and mix by inverting 5-10 times. Incubate samples at 50° C. for 1 hr. Gently invert the tubes every 10 min during incubation.

Step 8: Let the samples cool down to room temperature. Then, add 500 μl −20° C. 100% ethanol. Invert the tubes gently for about 5 min to precipitate the DNA. Centrifuge the samples at 13000 g for 5 min and discard the supernatant. Wash the DNA pellet with 500 μl 70% ethanol at room temperature for at least 30 min.

Step 9: Centrifuge the tubes at 13000 g for 5 min and discard the supernatant. Dry the sample tubes under the fume hood for about 30-60 min. Do not over-dry DNA pellet. Add 100 μl of $H_2O$ to each sample and suspend the DNA by pipetting. Let the samples sit at room temperature for about 30 min before checking the DNA quality and quantity, e.g., via a Nanodrop.

Store the DNA samples at 4° C. for temporary storage (up to a week), or at −20° C. for long-term storage.

Samples with different DHA canola DNA spikes were prepared according to this protocol:

Prepare 10 ng/μl DNA solutions from DHA canola and negative control AV Jade before making up the following spike samples.

50% spike sample: Mix equal volume of the DHA canola DNA solution (10 ng/μl) and the negative control AV Jade DNA solution (10 ng/μl).

10% spike sample: Dilute 5 times of the 50% spike sample with DNA solutions from the AV Jade (10 ng/μl) to make up the 10% spike sample.

1% spike sample: Dilute 10 times of the 10% spike sample with DNA from AV Jade (10 ng/μl) to make up the 1% spike sample.

PCR was conducted as follows. For PCR assembly: Assemble all reaction (25 μl/reaction) components (New England BioLabs Inc., Catalog #M0480L) on ice as illustrated in Table 1:

TABLE 1

PCR reaction assembly

| Components | Volume (μl) |
|---|---|
| 5× OneTaq Standard Reaction Buffer (NEB) | 5.0 |
| 10 mM of each dNTPs | 0.5 |
| 5 μM Internal Reference Gene (HMG) forward and reverse primers mixture | 2.0 |
| 5 μM forward and reverse Primers mixture | 2.0 |
| OneTaq DNA Polymerase (5 units/μl) (NEB) | 0.2 |
| Template DNA (10 ng/μl) | 5.0 |
| Nuclease-free water | 10.3 |
| Total reaction | 25.0 |

For PCR cycling profile: Touchdown PCR was used for amplification with the following profile parameters: one cycle of 94° C. for 30 sec, followed by six cycles of 94° C. for 30 sec, 63-57° C. (drop 1° C. per cycle) for 20 sec and 68° C. for 70-80 sec, and followed by thirty-three cycles of 94° C. for 30 sec, 58° C. for 20 sec and 68° C. for 70-80 sec with a final extension at 68° C. for 5 min. Finally, hold the PCR reaction at 10° C.

Agarose gel electrophoresis was carried out according to this protocol: For each sample, 5 μl PCR products, 3 μl $H_2O$, and 1 μl loading dye (6X; Thermo Fisher Scientific #R1161) were mixed before loading, and 6 μl DNA Ladder was used as reference. Run 3% agarose gel at 120 Volts for 65 min. Gels were photographed using a Life Technology Image system.

Thirty-nine primer pairs in total were designed and tested initially with DHA canola NS-B50027-4 and non-DHA canola samples. Two primer pairs, A02-282 and A05-286 (Table 2), generated specific band patterns that clearly distinguished DHA canola NS-B50027-4 samples from all non-DHA canola samples, and were selected for further analyses.

Figure 2B:
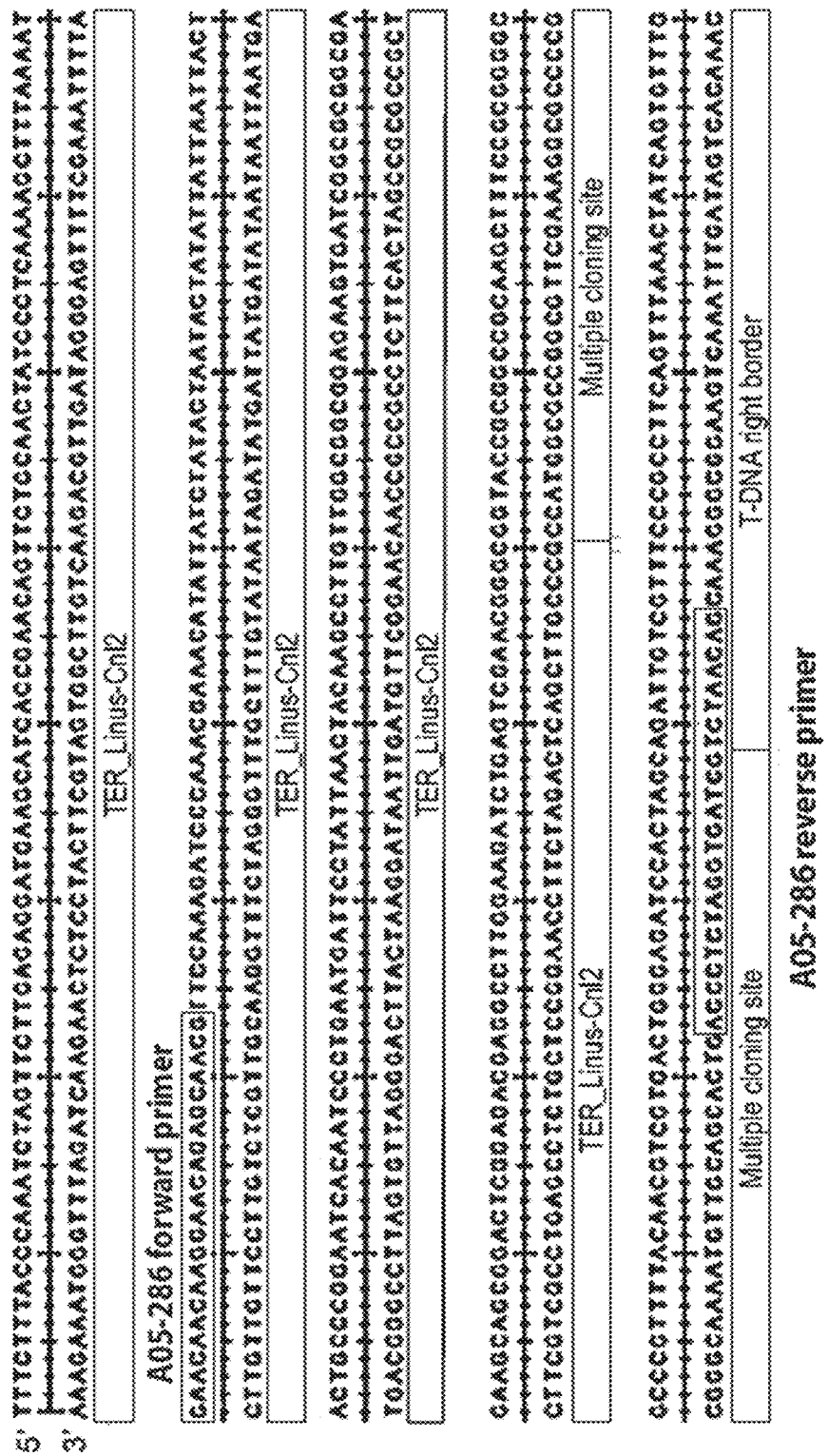
FIG. 2B shows primer locations (boxed) for assay A05-286 on chromosome A05 (SEQ ID NO:25); A05-286 forward primer (SEQ ID NO:3) and A05-286 reverse primer (SEQ ID NO:4). See Example 1.

Assay A02-282 was designed to detect the T-DNA insert on chromosome A02, and assay A05-286 was designed to detect the T-DNA insert on chromosome A05. The primer sequences, locations, and product sizes are shown in Table 2, FIG. 2A, and FIG. 2B.

TABLE 2

Primer sequences for assay A05-286, assay A02-282 and the reference gene HMG

| Sequence Name | Sequence | Product size | Target |
|---|---|---|---|
| A05-286F | GAA CAA CAA GGA ACA GAG CAA CGT (SEQ ID NO: 3) | 286 bp | Junction on Chromosome A05 (SEQ ID NO: 25) |
| A05-286R | GAC AAT CTG CTA GTG GAT CTC CCA (SEQ ID NO: 4) | | |
| A02-282F | CAG ATC TTC CAA GGC CTC GT (SEQ ID NO: 5) | 282 bp | Junction on Chromosome A02 (SEQ ID NO: 24) |
| A02-282R | CGC TCT TAT ACT GCA CTG GTT AG (SEQ ID NO: 6) | | |
| hmg99F | GGT CGT CCT CCT AAG GCG AAA G (SEQ ID NO: 7) | 99 bp | Internal reference gene HMG as control |
| hmg99R | CTT CTT CGG CGG TCG TCC AC (SEQ ID NO: 8) | | |

Figure 3A:
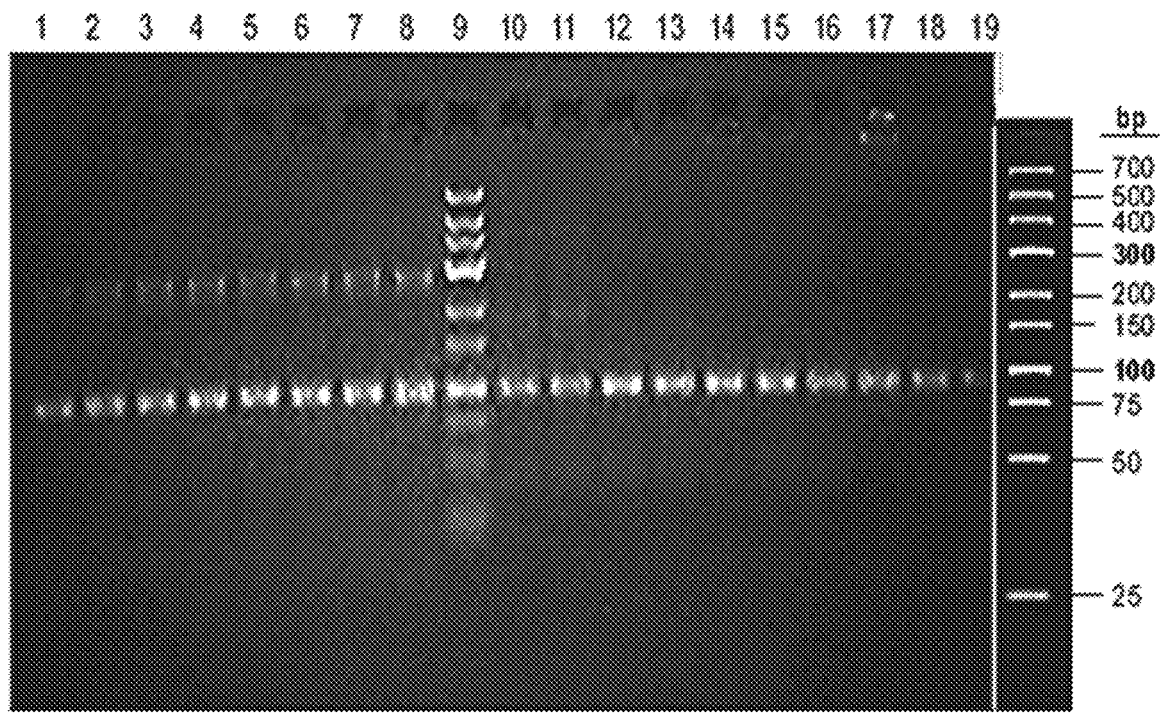
FIG. 3A is a gel image of A02-282 amplicons from DHA canola, non-GMO canola, and eight commercial GMO canola. Band A (top band), the 282-bp amplicon, was unique to DHA canola. Band B (bottom band), the 99-bp amplicon from internal reference gene HMG, was seen in all canola samples. Wells 1-8: Eight different samples containing NS-B50027-4 event; well 9: DNA ladder; well 10: non-GMO canola AV Jade; well 11: non-GMO canola Dwarf Essex Rape; wells 12-19: Bayer GMO canola events AOCS-1 (0306B4), AOCS-2 (0711D3), AOCS-3 (0208A5t), AOCS-4 (0711C2), AOCS-5 (0711B2), AOCS-6 (0306F6), AOCS-7 (0711A3), and AOCS-8 (0306G5), respectively.

Assay A02-282 was tested with a range of samples with various genetic backgrounds. DHA canola NS-B50027-4 vs. other GMO canola and two non-GMO canola (AV Jade and Dwarf Essex Rape), and eight commercial GMO canola lines (FIG. 3A). The results demonstrated that the 282-bp amplicon from assay A02-282 is DHA canola NS-B50027-4 event-specific. None of the eight commercial GMO canola events gave the 282-bp amplification.

Figure 3B:
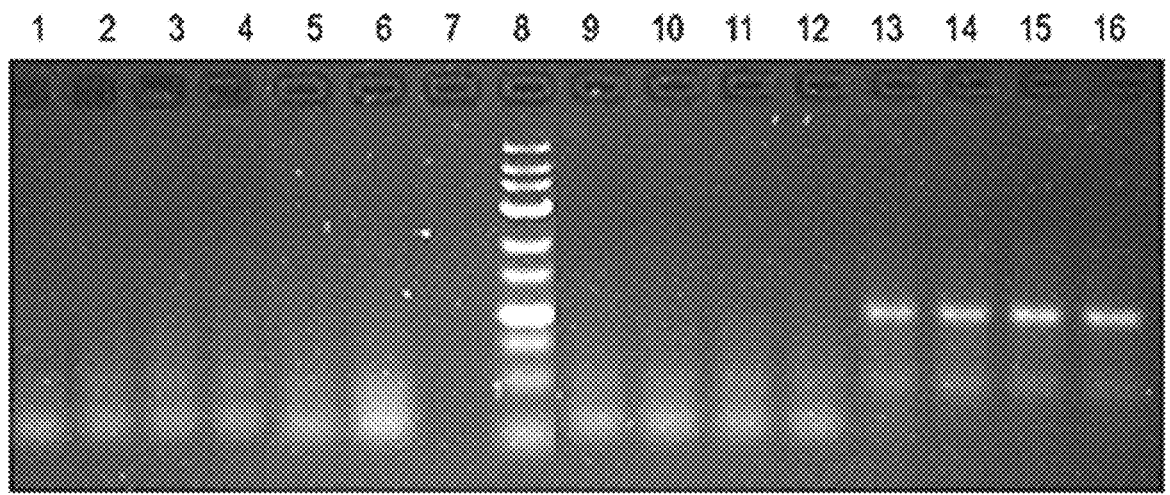
FIG. 3B is a gel image showing no A02-282 amplicons from GMO events in soybean, maize and cotton. Well 1: Soybean event AOCS-9 (see Table A for AOCS identifiers); well 2: soybean event AOCS-10; well 3: maize event AOCS-16; well 4: cotton event AOCS-23; well 5: soybean event AOCS-11; well 6: soybean events mixture; well 7: NTC; well 8: DNA ladder; well 9: maize event AOCS-17; well 10: maize events mixture; well 11: cotton event AOCS-24; well 12: cotton events mixture; well 13: non-transgenic canola sample 1; well 14: non-transgenic canola sample 2; well 15: non-transgenic canola sample 3; and well 16: non-transgenic canola sample 4. The 99-bp amplicons can be seen in non-GMO canola samples, but not in samples from soybean, maize and cotton.
Figure 4A:
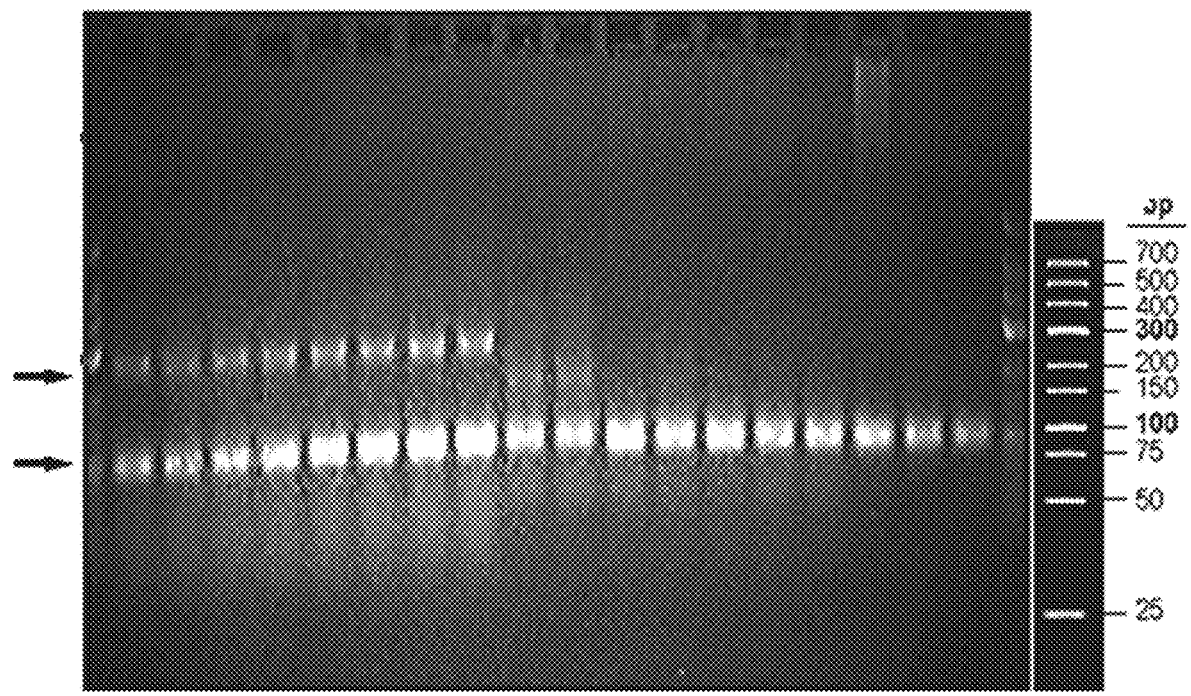
FIG. 4A shows a gel image of A05-286 amplicons from DHA canola NS-B50027-4, non-GMO canola and eight commercial GMO canola. Band A (top arrow), the 286-bp amplicon, was unique to DHA canola. Band B (bottom arrow), the 99-bp amplicon from internal reference gene HMG, was seen in all canola samples. Well 1 and 20 are DNA ladder; wells 2-9: eight different samples containing NS-B50027-4 event; well 10: non-GMO canola AV Jade; well 11: non-GMO canola Dwarf Essex Rape; wells 12-19: Bayer GMO canola events AOCS-1 (0306B4), AOCS-2 (0711D3), AOCS-3 (0208A5), AOCS-4 (0711C2), AOCS-5 (0711B2), AOCS-6 (0306F6), AOCS-7 (0711A3), and AOCS-8 (0306G5), respectively.
Figure 4B:
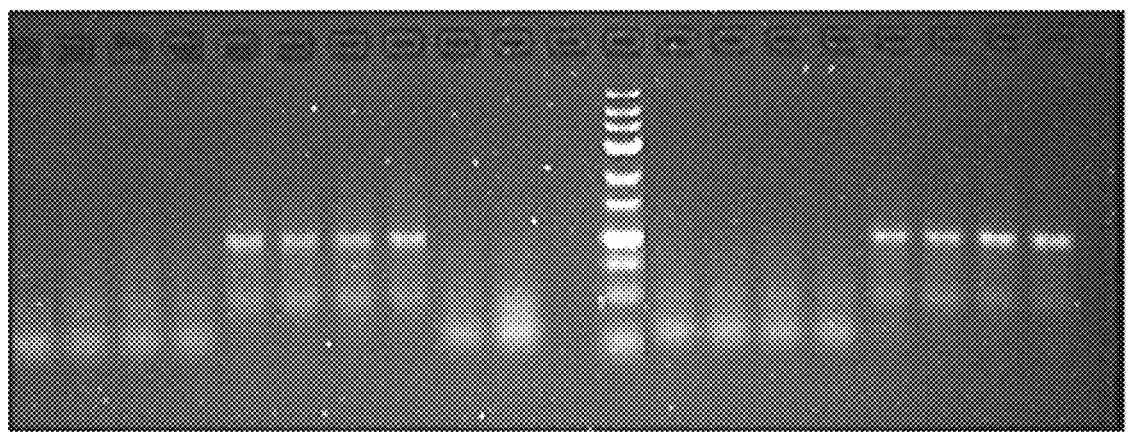
FIG. 4B shows a gel image of A05-286 amplicons from GMO events in soybean, maize and cotton. Well 1: Soybean event AOCS-9 (see Table A for AOCS identifiers); well 2: soybean event AOCS-10; well 3: soybean event AOCS-11; well 4: soybean events mixture; cotton event AOCS-23; well 5: non-transgenic canola sample 1; well 6: non-transgenic canola sample 2; well 7: non-transgenic canola sample 3; and well 8: non-transgenic canola sample 4; well 9: maize event AOCS-16; well 10: maize event AOCS-18; well 11: NTC; well 12: DNA ladder; well 13: maize events mixture; well 14: cotton event AOCS-23; well 15: cotton event AOCS-24; well 16: cotton events mixture; well 17: non-transgenic canola sample 5; well 18: non-transgenic canola sample 6; well 19: non-transgenic canola sample 7; and well 20: non-transgenic canola sample 8. The 99-bp amplicons could be seen in non-GMO canola samples, not in samples from soybean, maize, and cotton.

DHA canola vs. GMO materials from other species: A02-282 assay was also tested with commercial event samples from some other crops including soybean, maize and cotton (FIG. 3B). GMO materials from soybean, maize and cotton were ordered from AOCS (see Table A). The results demonstrated that the A02-282 assay generated the 282-bp amplicon from the DHA canola only, but not from GMO materials from soybean, maize and cotton.

NS-B50027-4 DHA canola vs. non-DHA canola in Nuseed germplasm: To test the consistency of assay A02-282, eleven DHA canola samples, sampled from two different test seed lots (A and B) and twelve non-DHA canola lines from Nuseed breeding germplasm were checked, and the results were listed in Table 3. No inconsistent results were observed.

TABLE 3

A02-282 assay results with samples with different genetic background

| Well | Sample | Category | A02-282 genotype | HMG genotype |
|---|---|---|---|---|
| 1 | A-sample1 | DHA canola | + | + |
| 2 | A-sample2 | DHA canola | + | + |
| 3 | NX0 | Non-DHA canola | − | + |
| 4 | A-sample3 | DHA canola | + | + |
| 5 | A-sample4 | DHA canola | + | + |
| 6 | A-sample5 | DHA canola | + | + |
| 7 | NX1 | Non-DHA canola | Reaction failed | Reaction failed |
| 8 | NX2 | Non-DHA canola | − | + |
| 9 | NX3 | Non-DHA canola | − | + |
| 10 | NX4 | Non-DHA canola | − | + |
| 11 | B-sample1 | DHA canola | + | + |
| 12 | B-sample2 | DHA canola | + | + |
| 13 | NX5 #25 | Non-DHA canola | − | + |
| 14 | NX6 #79 | Non-DHA canola | − | + |
| 15 | NX7 #34 | Non-DHA canola | − | + |
| 16 | DNA ladder | N.A. | N.A. | N.A. |
| 17 | B-sample3 | DHA canola | + | + |
| 18 | B-sample4 | DHA canola | + | + |
| 19 | B-sample5 | DHA canola | + | + |
| 20 | NX8 #87 | Non-DHA canola | − | + |
| 21 | NX9 #43 | Non-DHA canola | − | + |
| 22 | NX10 #96 | Non-DHA canola | − | + |
| 23 | NX11 #50 | Non-DHA canola | − | + |
| 24 | B-sample6 | DHA canola | + | + |

"+" event present;
"−" event absent;
"N.A." not applicable

To test the consistency of assay A05-286, twelve DHA canola samples (randomly sampled from two different NS-B50027-4 test seed lots A and B), and eleven non-DHA canola lines from Nuseed breeding germplasm were checked, and the results were listed in Table 4. All genotype results were as expected.

TABLE 4

A05-286 assay results for samples with different genetic background

| Well | sample | Category | A05-286 genotypes | HMG genotypes |
|---|---|---|---|---|
| 1 | NX1 | Non-DHA canola | − | + |
| 2 | NX2 | Non-DHA canola | − | + |
| 3 | A-sample1 | DHA canola | + | + |
| 4 | A-sample2 | DHA canola | + | + |
| 5 | A-sample3 | DHA canola | + | + |
| 6 | NX3 | Non-DHA canola | − | + |
| 7 | NX4 | Non-DHA canola | − | + |
| 8 | NX5 | Non-DHA canola | − | + |
| 9 | NX6 | Non-DHA canola | − | + |
| 10 | A-sample4 | DHA canola | + | + |
| 11 | A-sample5 | DHA canola | + | + |
| 12 | A-sample6 | DHA canola | + | + |
| 13 | B-sample1 | DHA canola | + | + |
| 14 | NX7 #25 | Non-DHA canola | − | + |
| 15 | DNA ladder | | N.A. | N.A. |
| 16 | B-sample2 | DHA canola | + | + |
| 17 | B-sample3 | DHA canola | + | + |
| 18 | B-sample4 | DHA canola | + | + |
| 19 | NX8 | Non-DHA canola | − | + |
| 20 | NX9 #87 | Non-DHA canola | − | + |
| 21 | NX10 #43 | Non-DHA canola | − | + |
| 22 | NX11 #96 | Non-DHA canola | − | + |
| 23 | B-sample5 | DHA canola | + | + |
| 24 | B-sample6 | DHA canola | + | + |

"+" indicates event present.
"−" indicates event absent.

Validation assays for A02-282 and A-2-286 were obtained. All individuals from the T7 generation containing DHA canola NS-B50027-4 event have the event specific band ("+" indicates event present) (Table 5). All individuals from the non-transgenic population do not have the event specific band. ("−" indicates event absent). FIG. 3A-FIG. 4B. All canola samples showed an HMG band except one sample where the PCR failed. Assay data is shown in Table 5:

TABLE 5

A02-282 and A05-286 assay validation results

| | A02-282 | | | | | | | A05-286 | | | | |
|---|---|---|---|---|---|---|---|---|---|---|---|---|
| Well | Row A | DHA | HMG | Row B | DHA | HMG | Row C | DHA | HMG | Row D | DHA | HMG |
| 1 | blank | N.A | N.A | blank | N.A | N.A | blank | N.A | N.A | blank | N.A | N.A |
| 2 | blank | N.A | N.A | blank | N.A | N.A | blank | N.A | N.A | blank | N.A | N.A |
| 3 | blank | N.A | N.A | blank | N.A | N.A | blank | N.A | N.A | blank | N.A | N.A |
| 4 | 1% DHA | + | + | T7-5 | + | + | 1% DHA | + | + | blank | N.A | N.A |
| 5 | 10% DHA | + | + | T7-6 | + | + | 10% DHA | + | + | T7-3 | + | + |

TABLE 5-continued

A02-282 and A05-286 assay validation results

| | A02-282 | | | | | | A05-286 | | | | |
|---|---|---|---|---|---|---|---|---|---|---|---|
| Well | Row A | DHA | HMG | Row B | DHA | HMG | Row C | DHA | HMG | Row D | DHA | HMG |
| 6 | 50% DHA | + | + | T7-7 | + | + | 50% DHA | + | + | T7-4 | + | + |
| 7 | AV Jade | − | + | 18079-5 | − | + | 18079-1 | − | Failed | T7-5 | + | + |
| 8 | 18079-1 | − | + | 18079-6 | − | + | 18079-2 | − | + | AV Jade | − | + |
| 9 | 18079-2 | − | + | 18079-7 | − | + | 18079-3 | − | + | 18079-8 | − | + |
| 10 | DNA ladder | N.A | N.A | DNA ladder | | | N.A DNA ladder | N.A | N.A | 18079-9 | − | + |
| 11 | 18079-3 | − | + | 18079-8 | − | + | 18079-4 | − | + | 18079-10 | − | + |
| 12 | T7-1 | + | + | T7-8 | + | + | T7-1 | + | + | T7-6 | + | + |
| 13 | T7-2 | + | + | T7-9 | + | + | T7-2 | + | + | T7-7 | + | + |
| 14 | T7-3 | + | + | T7-10 | + | + | 18079-5 | − | + | 18079-11 | − | + |
| 15 | T7-4 | + | + | T7-11 | + | + | 18079-6 | − | + | DNA ladder | N.A | N.A |
| 16 | 18079-4 | − | + | 18079-9 | − | + | 18079-7 | − | + | 18079-12 | − | + |
| 17 | blank | N.A | N.A | blank | N.A | N.A | blank | N.A | N.A | 18079-13 | − | + |
| 18 | blank | N.A | N.A | blank | N.A | N.A | blank | N.A | N.A | blank | N.A | N.A |
| 19 | blank | N.A | N.A | blank | N.A | N.A | blank | N.A | N.A | blank | N.A | N.A |
| 20 | blank | N.A | N.A | blank | N.A | N.A | blank | N.A | N.A | blank | N.A | N.A |
| 21 | blank | N.A | N.A | blank | N.A | N.A | blank | N.A | N.A | blank | N.A | N.A |
| 22 | blank | N.A | N.A | blank | N.A | N.A | blank | N.A | N.A | blank | N.A | N.A |

Event-specific gel-based assays A02-282 and A05-286, targeting the two inserts in DHA canola NS-B50027-4 on chromosome A02 and chromosome A05, respectively, were successfully developed and validated. The assays can be used for adventitious presence testing, trait purity testing, and trait introgression, and to support regulatory requirements and plant stewardship.

Example 2. Taqman Quantitative Detection Method for Nuseed DHA Canola Event NS-B50027-4

DHA Canola NS-B50027-4 (positive control), AV Jade (negative control) and twenty-seven Certified Reference Materials (CRM) from AOCS (Table A, Example 1) were used in developing and validating this assay. All Taqman reagents were obtained from Fisher Scientific Company LLC. Event-specific assay: Designed by Nuseed, Fisher Scientific Customer Design Catalog #4400294. HMG reference gene assay: Designed by Nuseed, Fisher Scientific Customer Design Catalog #4467084. Applied Biosystems™ TaqPath™ ProAmp™ Master Mix Catalog #A30871 (2×10 ml). TaqMan® Copy Number Assays Protocol was obtained from Applied Biosystems. Data was processed using CFX96 Realtime System Bio-Rad C1000 Touch user manual-Bio-Rad and CFX Manager™ Software #1845000-Bio-Rad.

DNA extraction was carried out as in Example 1. Preparation of sample standards followed this protocol:
Prepare 4 ng/l DNA working solutions before making the following standard sample solutions which have different DHA spike DNA concentrations:
50% spike sample: Mix equal volume of DHA positive DNA samples and DHA negative AV Jade DNA samples.
10% spike sample: Dilute 5 times 50% spike samples with DNA from AV Jade to make 10% spike sample.
1% spike sample: Dilute 10 times 10% spike samples with DNA from AV Jade to make 1% spike sample.
0.1% spike sample: Dilute 10 times 1% spike samples with DNA from AV Jade to make 0.1% spike sample.
0.01% spike sample: Dilute 10 times 0.1% spike samples with DNA from AV Jade to make 0.01% spike sample.
0.005% spike sample: Dilute 2 times 0.01% spike samples with DNA from AV Jade to make 0.005% spike sample.

For PCR reaction assembly, all reaction (20 μL/reaction) components were assembled on ice.

TABLE 6

PCR Reaction Components

| Component | Volume (μl) |
|---|---|
| 2× Master mix | 10.0 |
| Internal reference gene HMG assay (20×) | 1.0 |
| Event-specific assay (20×) | 1.0 |
| Template DNA (4 ng/μl) | 5.0 |
| Nuclease-free water | 3.0 |
| Total reaction volume | 20.0 |

PCR cycling profile: CFX96 RealTime System Bio-Rad C1000 Touch was used to run the reaction with the following Taqman PCR profile:

TABLE 7

PCR Reaction Parameters

| Stage | Temperature | Time |
|---|---|---|
| Hold | 95° C. | 10 min |
| Cycle | 95° C. | 15 sec |
| (40 Cycles) | 60° C. | 60 sec |

The obtained data were analyzed using Bio-Rad CFX manager.

Sequences used for a Taqman assay were designed, and canola HMG was used as the internal reference gene for the quantitative detection method. The junction sequences around the T-DNA insertion sites on chromosome A02 and A05 were used for primer and probe design using software Primer3Plus, and details are as follows:

TABLE 8A

Parameters of the primers and probes designed from A02 and A05 insertion sites with Primer3Plus software

A02 downstream insertion site (product size 170 bp)

| Start | Length | Tm (° C.) | GC % | Any | End | TB | HP | 3' Stab |
|---|---|---|---|---|---|---|---|---|
| Left Primer 2: ACAAGGCTTGTAGTTAATAGGAATCA (SEQ ID NO: 15) | | | | | | | | |
| 12 | 26 bp | 58.4 | 34.6 | 30.3 | 0.0 | 7.0 | 43.3 | 2 |
| Internal Oligo 2: TCAGGGATTGTGATTCCGGGCA (SEQ ID NO: 17) | | | | | | | | |
| 39 | 22 bp | 58.0 | 54.5 | 0.0 | 0.0 | | 30.5 | 0 |
| Right Primer 2: ACGATCAACTAATCAGAAGCTCAATT (SEQ ID NO: 16) | | | | | | | | |
| 181 | 26 bp | 59.2 | 34.6 | 0.0 | 0.0 | 14.0 | 0.0 | 2 |

A05 upstream insertion site (product size 120 bp)

| Start | Length | Tm (° C.) | GC % | Any | End | TB | HP | |
|---|---|---|---|---|---|---|---|---|
| Left Primer 5: TCTATCCTTTGGCTAGCGGC (SEQ ID NO: 12) | | | | | | | | |
| 75 | 20 bp | 59.6 | 55.0 | 9.0 | 0.0 | 6.0 | 40.9 | |
| Internal Oligo 5: CAACCGTTGGCTAAGGTAACACTGA (SEQ ID NO: 14) | | | | | | | | |
| 118 | 25 bp | 57.2 | 48.0 | 2.3 | 0.0 | | 33.1 | |
| Right Primer 5: TGACTGGGAGATCCACTAGCA (SEQ ID NO: 13) | | | | | | | | |
| 194 | 21 bp | 60.0 | 52.4 | 0.5 | 0.0 | 5.0 | 41.5 | |

The A02 insert downstream junction sequence used for assay design is shown below, totally 189 bp long. Bases 1-84 is canola genomic sequences shown in italics, and 85-189 are T-DNA sequences (i.e., transgenic construct) shown in normal text:

(SEQ ID NO: 9)
*CTCCGCCGCCAACAAGGCTTGTAGTTAATAGGAATCATTCAGGGATTGT*

*GATTCCGGGCAGTAGTAATTAATAATATAGTATTAGTATACAGAACCTC*

TTATTTAGCTAAAAGATTATGTTCTTAATGTTGATAAGAAGTTTGAGAA

ACAAATATAATTGAGCTTCTGATTAGTTGATCGTAATTGGTC

The A05 insert upstream junction sequence used for assay design is shown below, totally 226 bp long. Bases 1-134 are T-DNA sequences are shown in normal text, and 135-226 are canola genomic sequences are in italics:

(SEQ ID NO: 10)
TTTTCGTCGAGTTGCTGAAACTGGACCCAAGCCAGTGTACGGCGCAGGA

GGTACTTTAAGCTTATAACCCTTTGTCTATCCTTTGGCTAGCGGCTAAT

GTTGATGAACTTTTTTATTCAACCGTTGGCTAAGGTAACACTGATAGTT

*TAAACTGAAGGCGGGAAACGACAATCTGCTAGTGGATCTCCCAGTCACG*

*ACGTTGTAAAACGGGCGCCCCGCGGAAAGC*

Nine TaqMan insert-specific assays targeting the A02 and A05 inserts (Table 8B) were selected and supplied by a commercial supplier (Fisher Thermos):

TABLE 8B

Assay ID and product size.

| Assay number | Assay ID | Chromosome | Product size (bp) |
|---|---|---|---|
| 1 | A05up1_CDFVKVE | A05 | 135 |
| 2 | A05up2_CDGZFFC | A05 | 120 |
| 3 | A05dn1_CDH49Y9 | A05 | 102 |
| 4 | A05dn2_CDKA3J6 | A05 | 119 |
| 5 | A02up1_CDMFW43 | A02 | 106 |
| 6 | A02up2_CDNKRPZ | A02 | 105 |
| 7 | A02up3_CDPRKAX | A02 | 101 |
| 8 | A02dn1_CDRWEVV | A02 | 173 |
| 9 | A02dn2_CDTZ9FT | A02 | 170 |

These nine assays were tested with the same samples and PCR profiling as described herein. Among the nine assays, A02dn2_CDTZ9FT (derived from A02 insert downstream junction sequence and named A02dn2) and A05up2_CDGZFFC (derived from A05 insert upstream junction sequence and named A05up2) (Table 9), plus the assay for internal reference gene HMG ("hmg") showed consistent results and were selected for further analyses.

TABLE 9

Selected Taqman assays targeting the internal reference canola HMG gene and the two DHA insert-specific sites on chromosomes A02 and A05

| Name | Sequence | Product size |
|---|---|---|
| hmg-F | GGTCGTCCTCCTAAGGCGAAAG (SEQ ID NO: 7) | 99 bp |
| hmg-R | CTTCTTCGGCGGTCGTCCAC (SEQ ID NO: 8) | |

TABLE 9-continued

Selected Taqman assays targeting the internal reference canola HMG gene and the two DHA insert-specific sites on chromosomes A02 and A05

| Name | Sequence | Product size |
|---|---|---|
| hmg-P | VIC - CGGAGCCACTCGGTGCCGCAACTT (SEQ ID NO: 11) | |
| A05up2F | TCTATCCTTTGGCTAGCGGC (SEQ ID NO: 12) | 120 bp |
| A05up2R | TGACTGGGAGATCCACTAGCA (SEQ ID NO: 13) | |
| A05up2P | FAM - CAACCGTTGGCTAAGGTAACACTGA (SEQ ID NO: 14) | |
| A02dn2F | ACAAGGCTTGTAGTTAATAGGAATCA (SEQ ID NO: 15) | 170 bp |
| A02dn2R | ACGATCAACTAATCAGAAGCTCAATT (SEQ ID NO: 16) | |
| A02dn2P | FAM - TCAGGGATTGTGATTCCGGGCA (SEQ ID NO: 17) | |

Primer and probe locations of the two Taqman assays targeting two junctions of the two T-DNA inserts are shown in FIG. 5A (chromosome A02) and FIG. 5B (chromosome A05), where primer sequences are highlighted in light gray, and probe sequences in medium gray. Sequences in dark gray indicate the complementary sequences of the reverse primers below it.

Figure 6:
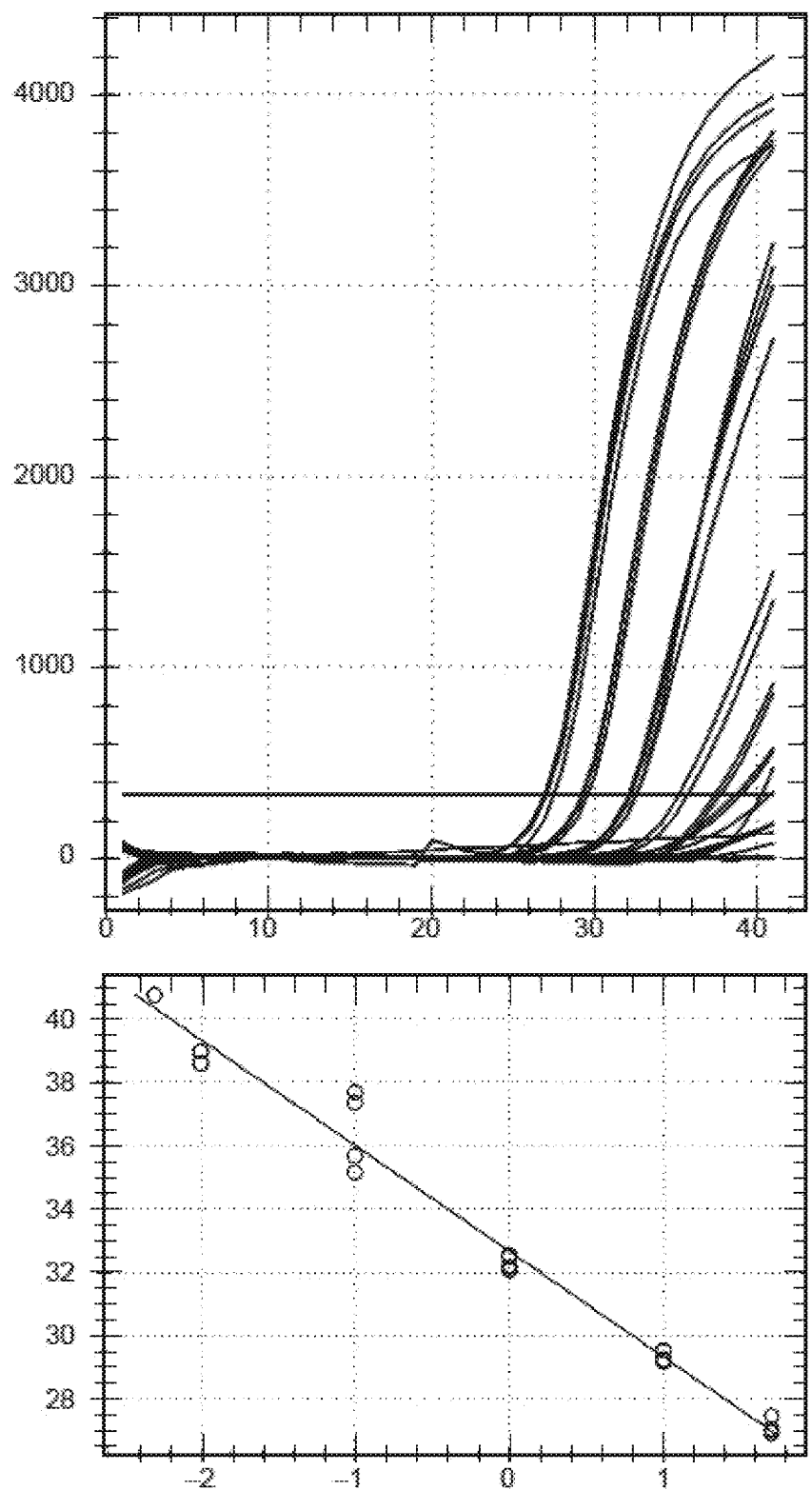
FIG. 6 shows the amplification plot (top panel, RFU per Cycles, Log scale) and standard curve (bottom panel, Cq over Log Starting Quantity) from the A02dn2 event-specific assay. The R square value of the standard curve was 0.981 and the slope of the standard curve was −3.34 for A02dn2.

Results on assay A02dn2, more specifically the amplification plot and standard curve for A02dn2 is shown in FIG. 6. The quantification data from A02dn2 insert specific assay with the standard samples were listed in Table 10. The data show the lowest transgenic level detected in all four replications was 0.01 with A02dn2 insert specific assay for canola NS-500274 DHA event.

TABLE 10

Results from A02dn2 insert specific assay with standard DNA samples and the controls

| Well | Fluor | Target | Content | Sample name | Cq(Ct) |
|---|---|---|---|---|---|
| A09 | FAM | A02dn2 | Std | 50% spike | 26.83 |
| A10 | FAM | A02dn2 | Std | 50% spike | 26.80 |
| A11 | FAM | A02dn2 | Std | 50% spike | 26.95 |
| A12 | FAM | A02dn2 | Std | 50% spike | 27.38 |
| B09 | FAM | A02dn2 | Std | 10% spike | 29.16 |
| B10 | FAM | A02dn2 | Std | 10% spike | 29.17 |
| B11 | FAM | A02dn2 | Std | 10% spike | 29.10 |
| B12 | FAM | A02dn2 | Std | 10% spike | 29.43 |
| C09 | FAM | A02dn2 | Std | 1% spike | 31.99 |
| C10 | FAM | A02dn2 | Std | 1% spike | 32.10 |
| C11 | FAM | A02dn2 | Std | 1% spike | 32.43 |
| C12 | FAM | A02dn2 | Std | 1% spike | 32.41 |
| D09 | FAM | A02dn2 | Std | 0.1% spike | 37.20 |
| D10 | FAM | A02dn2 | Std | 0.1% spike | 35.04 |
| D11 | FAM | A02dn2 | Std | 0.1% spike | 35.54 |
| D12 | FAM | A02dn2 | Std | 0.1% spike | 37.51 |
| E09 | FAM | A02dn2 | Std | 0.01% spike | 38.34 |
| E10 | FAM | A02dn2 | Std | 0.01% spike | 38.72 |
| E11 | FAM | A02dn2 | Std | 0.01% spike | N/A |
| E12 | FAM | A02dn2 | Std | 0.01% spike | 38.34 |
| F09 | FAM | A02dn2 | Std | 0.005% spike | N/A |
| F10 | FAM | A02dn2 | Std | 0.005% spike | N/A |
| F11 | FAM | A02dn2 | Std | 0.005% spike | 40.49 |
| F12 | FAM | A02dn2 | Std | 0.005% spike | N/A |
| G09 | FAM | A02dn2 | Neg Ctrl | AV Jade | N/A |
| G10 | FAM | A02dn2 | Neg Ctrl | AV Jade | N/A |
| G11 | FAM | A02dn2 | Neg Ctrl | AV Jade | N/A |
| G12 | FAM | A02dn2 | Neg Ctrl | AV Jade | N/A |
| H09 | FAM | A02dn2 | NTC | NTC | N/A |
| H10 | FAM | A02dn2 | NTC | NTC | 40.10 |
| H11 | FAM | A02dn2 | NTC | NTC | N/A |
| H12 | FAM | A02dn2 | NTC | NTC | N/A |
| A09 | VIC | HMG | Std | 50% spike | 28.47 |
| A10 | VIC | HMG | Std | 50% spike | 28.09 |
| A11 | VIC | HMG | Std | 50% spike | 28.33 |
| A12 | VIC | HMG | Std | 50% spike | 30.02 |
| B09 | VIC | HMG | Std | 10% spike | 28.62 |
| B10 | VIC | HMG | Std | 10% spike | 28.61 |
| B11 | VIC | HMG | Std | 10% spike | 27.88 |
| B12 | VIC | HMG | Std | 10% spike | 29.02 |
| C09 | VIC | HMG | Std | 1% spike | 28.59 |
| C10 | VIC | HMG | Std | 1% spike | 28.38 |
| C11 | VIC | HMG | Std | 1% spike | 28.56 |
| C12 | VIC | HMG | Std | 1% spike | 28.57 |
| D09 | VIC | HMG | Std | 0.1% spike | 19.43 |
| D10 | VIC | HMG | Std | 0.1% spike | 29.02 |
| D11 | VIC | HMG | Std | 0.1% spike | 28.71 |
| D12 | VIC | HMG | Std | 0.1% spike | 29.14 |
| E09 | VIC | HMG | Std | 0.01% spike | 28.50 |
| E10 | VIC | HMG | Std | 0.01% spike | 28.36 |
| E11 | VIC | HMG | Std | 0.01% spike | 28.74 |
| E12 | VIC | HMG | Std | 0.01% spike | 28.86 |
| F09 | VIC | HMG | Std | 0.005% spike | 28.51 |
| F10 | VIC | HMG | Std | 0.005% spike | 28.30 |
| F11 | VIC | HMG | Std | 0.005% spike | 28.43 |
| F12 | VIC | HMG | Std | 0.005% spike | 28.96 |
| G09 | VIC | HMG | Neg Ctrl | AV Jade | 28.62 |
| G10 | VIC | HMG | Neg Ctrl | AV Jade | 28.28 |
| G11 | VIC | HMG | Neg Ctrl | AV Jade | 28.44 |
| G12 | VIC | HMG | Neg Ctrl | AV Jade | 29.12 |
| H09 | VIC | HMG | NTC | NTC | N/A |
| H10 | VIC | HMG | NTC | NTC | N/A |
| H11 | VIC | HMG | NTC | NTC | N/A |
| H12 | VIC | HMG | NTC | NTC | 40.33 |

Std = standard sample;
Neg Ctrl = negative control;
NTC = no template control;
N/A = Not available The assay A02dn2 was also validated with twenty-seven Certified Reference Materials (CRM) ordered from AOCS. The results are shown in Table 11. The results demonstrated that the assay A02dn2 detected and showed positive results only from the canola materials that contained DHA canola NS-1B50027-4 DHA event. It generated negative results from all twenty-seven commercial transgenic events (Example 1, Table A) including eight canola events, seven maize events, seven soybean events, and five cotton events. The results further demonstrated that assay A02dn2 was event-specific for Nuseed canola NS-1B50027-4 DHA event.

TABLE 11

Results from A02dn2 assay tested with 27 Reference materials

| Well | Fluor | Target | Content | Sample name | Cq(Ct) |
|---|---|---|---|---|---|
| A08 | FAM | A02dn2 | Std | 50% spike | 26.42 |
| B08 | FAM | A02dn2 | Std | 10% spike | 28.54 |
| C08 | FAM | A02dn2 | Std | 1% spike | 30.13 |
| D08 | FAM | A02dn2 | Std | 0.1% spike | 32.13 |
| E08 | FAM | A02dn2 | Std | 0.01% spike | 35.05 |
| F08 | FAM | A02dn2 | Std | 0.005% spike | N/A |

TABLE 11-continued

Results from A02dn2 assay tested with 27 Reference materials

| Well | Fluor | Target | Content | Sample name | Cq(Ct) |
|---|---|---|---|---|---|
| G08 | FAM | A02dn2 | Neg Ctrl | AV Jade | 39.49 |
| H08 | FAM | A02dn2 | NTC | NTC | N/A |
| A09 | FAM | A02dn2 | Unkn | AOCS-1 | 37.16 |
| B09 | FAM | A02dn2 | Unkn | AOCS-2 | 38.16 |
| C09 | FAM | A02dn2 | Unkn | AOCS-3 | 37.28 |
| D09 | FAM | A02dn2 | Unkn | AOCS-4 | 39.75 |
| E09 | FAM | A02dn2 | Unkn | AOCS-5 | 38.19 |
| F09 | FAM | A02dn2 | Unkn | AOCS-6 | 38.95 |
| G09 | FAM | A02dn2 | Unkn | AOCS-7 | 39.12 |
| H09 | FAM | A02dn2 | Unkn | AOCS-8 | 38.66 |
| A10 | FAM | A02dn2 | Unkn | AOCS-9 | N/A |
| B10 | FAM | A02dn2 | Unkn | AOCS-10 | 38.10 |
| C10 | FAM | A02dn2 | Unkn | AOCS-11 | N/A |
| D10 | FAM | A02dn2 | Unkn | AOCS-12 | N/A |
| E10 | FAM | A02dn2 | Unkn | AOCS-13 | 36.22 |
| F10 | FAM | A02dn2 | Unkn | AOCS-14 | 35.40 |
| G10 | FAM | A02dn2 | Unkn | AOCS-15 | 36.15 |
| H10 | FAM | A02dn2 | Unkn | AOCS-16 | 36.53 |
| A11 | FAM | A02dn2 | Unkn | AOCS-17 | 35.14 |
| B11 | FAM | A02dn2 | Unkn | AOCS-18 | 35.19 |
| C11 | FAM | A02dn2 | Unkn | AOCS-19 | 35.27 |
| D11 | FAM | A02dn2 | Unkn | AOCS-20 | 36.04 |
| E11 | FAM | A02dn2 | Unkn | AOCS-21 | N/A |
| F11 | FAM | A02dn2 | Unkn | AOCS-22 | N/A |
| G11 | FAM | A02dn2 | Unkn | AOCS-23 | 36.01 |
| H11 | FAM | A02dn2 | Unkn | AOCS-24 | 36.04 |
| A12 | FAM | A02dn2 | Unkn | AOCS-25 | 36.38 |
| B12 | FAM | A02dn2 | Unkn | AOCS-26 | 36.04 |
| C12 | FAM | A02dn2 | Unkn | AOCS-27 | 38.17 |

Unkn = unknown

Regarding the results of the A05up2 assay, the amplification plot and standard curve for A05up2 are shown in FIG. 7, and data presented in Table 12:

TABLE 12

Assay A05up2 results on the standard DNA samples and controls

| Well | Fluor | Target | Content | Sample name | Cq (Ct) |
|---|---|---|---|---|---|
| A01 | FAM | A05up2 | Std | 50% spike | 26.31 |
| A02 | FAM | A05up2 | Std | 50% spike | 26.45 |
| A03 | FAM | A05up2 | Std | 50% spike | 26.37 |
| A04 | FAM | A05up2 | Std | 50% spike | 26.27 |
| B01 | FAM | A05up2 | Std | 10% spike | 28.64 |
| B02 | FAM | A05up2 | Std | 10% spike | 28.51 |
| B03 | FAM | A05up2 | Std | 10% spike | 28.44 |
| B04 | FAM | A05up2 | Std | 10% spike | 28.28 |
| C01 | FAM | A05up2 | Std | 1% spike | 31.16 |
| C02 | FAM | A05up2 | Std | 1% spike | 31.19 |
| C03 | FAM | A05up2 | Std | 1% spike | 31.64 |
| C04 | FAM | A05up2 | Std | 1% spike | 31.44 |
| D01 | FAM | A05up2 | Std | 0.1% spike | 35.04 |
| D02 | FAM | A05up2 | Std | 0.1% spike | 34.52 |
| D03 | FAM | A05up2 | Std | 0.1% spike | 36.19 |
| D04 | FAM | A05up2 | Std | 0.1% spike | 35.03 |
| E01 | FAM | A05up2 | Std | 0.01% spike | 39.28 |
| E02 | FAM | A05up2 | Std | 0.01% spike | 37.92 |
| E03 | FAM | A05up2 | Std | 0.01% spike | N/A |
| E04 | FAM | A05up2 | Std | 0.01% spike | 37.87 |
| F01 | FAM | A05up2 | Std | 0.005% spike | N/A |
| F02 | FAM | A05up2 | Std | 0.005% spike | N/A |
| F03 | FAM | A05up2 | Std | 0.005% spike | N/A |
| F04 | FAM | A05up2 | Std | 0.005% spike | 40.10 |
| G01 | FAM | A05up2 | Neg Ctrl | AV Jade | N/A |
| G02 | FAM | A05up2 | Neg Ctrl | AV Jade | N/A |
| G03 | FAM | A05up2 | Neg Ctrl | AV Jade | N/A |
| G04 | FAM | A05up2 | Neg Ctrl | AV Jade | N/A |
| H01 | FAM | A05up2 | NTC | NTC | N/A |
| H02 | FAM | A05up2 | NTC | NTC | N/A |
| H03 | FAM | A05up2 | NTC | NTC | N/A |
| H04 | FAM | A05up2 | NTC | NTC | N/A |
| A01 | VIC | HMG | Std | 50% spike | 28.71 |

TABLE 12-continued

Assay A05up2 results on the standard DNA samples and controls

| Well | Fluor | Target | Content | Sample name | Cq (Ct) |
|---|---|---|---|---|---|
| A02 | VIC | HMG | Std | 50% spike | 28.55 |
| A03 | VIC | HMG | Std | 50% spike | 28.21 |
| A04 | VIC | HMG | Std | 50% spike | 28.22 |
| B01 | VIC | HMG | Std | 10% spike | 28.74 |
| B02 | VIC | HMG | Std | 10% spike | 27.93 |
| B03 | VIC | HMG | Std | 10% spike | 28.28 |
| B04 | VIC | HMG | Std | 10% spike | 28.19 |
| C01 | VIC | HMG | Std | 1% spike | 28.40 |
| C02 | VIC | HMG | Std | 1% spike | 28.27 |
| C03 | VIC | HMG | Std | 1% spike | 28.04 |
| C04 | VIC | HMG | Std | 1% spike | 28.36 |
| D01 | VIC | HMG | Std | 0.1% spike | 29.37 |
| D02 | VIC | HMG | Std | 0.1% spike | 28.22 |
| D03 | VIC | HMG | Std | 0.1% spike | 28.32 |
| D04 | VIC | HMG | Std | 0.1% spike | 28.40 |
| E01 | VIC | HMG | Std | 0.01% spike | 30.05 |
| E02 | VIC | HMG | Std | 0.01% spike | 28.26 |
| E03 | VIC | HMG | Std | 0.01% spike | 28.37 |
| E04 | VIC | HMG | Std | 0.01% spike | 26.91 |
| F01 | VIC | HMG | Std | 0.005% spike | 29.76 |
| F02 | VIC | HMG | Std | 0.005% spike | 28.17 |
| F03 | VIC | HMG | Std | 0.005% spike | 27.99 |
| F04 | VIC | HMG | Std | 0.005% spike | 28.22 |
| G01 | VIC | HMG | Neg Ctrl | AV Jade | 29.49 |
| G02 | VIC | HMG | Neg Ctrl | AV Jade | 28.19 |
| G03 | VIC | HMG | Neg Ctrl | AV Jade | 28.36 |
| G04 | VIC | HMG | Neg Ctrl | AV Jade | 28.25 |
| H01 | VIC | HMG | NTC | NTC | N/A |
| H02 | VIC | HMG | NTC | NTC | N/A |
| H03 | VIC | HMG | NTC | NTC | N/A |
| H04 | VIC | HMG | NTC | NTC | N/A |

The assay A05up2 was also validated with 27 Certified Reference Materials (CRM, from AOCS, Example 1, Table A). The results are shown in Table 13:

TABLE 13

Results from A05up2 assay on the 27 Reference materials from AOCS

| Well | Fluor | Target | Content | Sample Name | Cq(Ct) |
|---|---|---|---|---|---|
| A01 | FAM | A05up2 | Std | 50% spike | 27.18 |
| B01 | FAM | A05up2 | Std | 10% spike | 30.74 |
| C01 | FAM | A05up2 | Std | 1% spike | 32.63 |
| D01 | FAM | A05up2 | Std | 0.1% spike | 35.77 |
| E01 | FAM | A05up2 | Std | 0.01% spike | 37.57 |
| F01 | FAM | A05up2 | Std | 0.005% spike | N/A |
| G01 | FAM | A05up2 | Neg Ctrl | AV Jade | 37.98 |
| H01 | FAM | A05up2 | NTC | NTC | N/A |
| B02 | FAM | A05up2 | Unkn | AOCS-1 | 37.17 |
| C02 | FAM | A05up2 | Unkn | AOCS-2 | 39.14 |
| D02 | FAM | A05up2 | Unkn | AOCS-3 | 40.5 |
| E02 | FAM | A05up2 | Unkn | AOCS-4 | 38.85 |
| F02 | FAM | A05up2 | Unkn | AOCS-5 | N/A |
| G02 | FAM | A05up2 | Unkn | AOCS-6 | N/A |
| H02 | FAM | A05up2 | Unkn | AOCS-7 | 40.5 |
| A03 | FAM | A05up2 | Unkn | AOCS-8 | 39.16 |
| B03 | FAM | A05up2 | Unkn | AOCS-9 | 38.56 |
| C03 | FAM | A05up2 | Unkn | AOCS-10 | 40.36 |
| D03 | FAM | A05up2 | Unkn | AOCS-11 | 37.25 |
| E03 | FAM | A05up2 | Unkn | AOCS-12 | 39.14 |
| F03 | FAM | A05up2 | Unkn | AOCS-13 | 37.38 |
| G03 | FAM | A05up2 | Unkn | AOCS-14 | 38.16 |
| H03 | FAM | A05up2 | Unkn | AOCS-15 | 40.36 |
| A04 | FAM | A05up2 | Unkn | AOCS-16 | 40.41 |
| B04 | FAM | A05up2 | Unkn | AOCS-17 | 37.13 |
| C04 | FAM | A05up2 | Unkn | AOCS-18 | 39.69 |
| D04 | FAM | A05up2 | Unkn | AOCS-19 | 38.96 |
| E04 | FAM | A05up2 | Unkn | AOCS-20 | 39.16 |
| F04 | FAM | A05up2 | Unkn | AOCS-21 | 40.41 |
| G04 | FAM | A05up2 | Unkn | AOCS-22 | N/A |
| H04 | FAM | A05up2 | Unkn | AOCS-23 | N/A |
| A05 | FAM | A05up3 | Unkn | AOCS-24 | N/A |

TABLE 13-continued

Results from A05up2 assay on the 27 Reference materials from AOCS

| Well | Fluor | Target | Content | Sample Name | Cq(Ct) |
|---|---|---|---|---|---|
| B05 | FAM | A05up4 | Unkn | AOCS-25 | N/A |
| C05 | FAM | A05up5 | Unkn | AOCS-26 | N/A |
| D05 | FAM | A05up6 | Unkn | AOCS-27 | 40.36 |

The results demonstrated the assay A05up2 can quantitatively detect the DHA canola DNA only from the canola materials that contained canola NS-B50027-4 DHA event. It generated negative results from all twenty-seven commercial transgenic events including eight canola events, seven maize events, seven soybean events, and five cotton events. The results further demonstrated that the assay A05up2 was event specific for Nuseed DHA canola NS-B50027-4 event.

An event specific assay set containing two assays, A02dn2 and A05up2, targeting the two inserts of DHA canola NS-B50027-4 event, was developed and validated. A Taqman assay targeting the internal reference canola HMG gene was also developed and served as internal control. These quantitative Taqman assays can be used for adventitious presence testing, low level presence testing, trait purity testing, trait introgression, and to support regulatory submissions and elite event plant stewardship.

Example 3. Gel Electrophoresis-Based A02-258 and A05-200 Assays for Qualitative Detection of the Transgenic Event in DHA Canola NS-B50027-4

This example provides a qualitative detection method developed to determine the presence of DHA Canola (Event NS-B50027-4) in oilseeds DNA sample. As shown herein, the assays can be used for adventitious presence testing, trait purity testing, and trait introgression, and to support DHA Canola NS-B50027-4 regulatory submission and commercialization.

Event-specific gel-based assays A02-258 and A05-200, targeting the two inserts in DHA canola NS-B50027-4 on chromosome A02 and chromosome A05, respectively, have been successfully developed. The HMG reference gene PCR profile was designed as reference gene to confirm the PCR ability of DNA sample.

The Limit of Detection (LOD) of the two event-specific assays is determined at least 0.05% NS-B50027-4 DNA to total DNA, or less than 50 genome copies.

DNAs were extracted from the seeds using CTAB DNA extraction method as described in Example 1.

Samples with different DHA canola DNA spikes were prepared according to the protocol as described below:

Prepare 20 ng/µl DNA solutions from DHA canola NS-B50027-4 DNA and negative control AV Jade before making up the following spiked samples.

| List of spiked samples: | | |
|---|---|---|
| 1. | 50% spike sample: | Mix equal volume of the DHA canola DNA solution (20 ng/µL) and the negative control AV Jade DNA solution (20 ng/µL). |
| 2. | 10% spike sample: | Dilute 5 times of the 50% spike sample with DNA solutions from the AV Jade (20ng/µL) to make up the 10% spike sample. |
| 3. | 1% spike sample: | Dilute 10 times of the 10% spike sample with DNA from AV Jade (20 ng/µL) to make up the 1% spike sample. |
| 4. | 0.1% spike sample: | Dilute 10 times of the 1% spike sample with DNA from AV Jade (20 ng/µL) to make up the 0.1% spike sample. |
| 5. | 0.05% spike sample: | Dilute 2 times of the 0.1% spike sample with DNA from AV Jade (20 ng/µL) to make up the 0.05% spike sample. |
| 6. | 0.025% spike sample: | Dilute 2 times of the 0.05% spike sample with DNA from AV Jade (20 ng/µL) to make up the 0.025% spike sample. |

Six DHA canola NS-B50027-4 spike levels were made as described below, the genome copies number of reference gene HMG and DHA canola is listed in Table 14.

TABLE 14

Six spike-level samples with corresponding reference gene genome copy number, and the copy number for NS-B50027-4

| | | | | | | |
|---|---|---|---|---|---|---|
| DHA canola dilution series | 50% | 10% | 1% | 0.1% | 0.05% | 0.025% |
| Total amount of DNA in reaction (ng) | 100 | 100 | 100 | 100 | 100 | 100 |
| Target taxon HMG copies | 86957 | 86957 | 86957 | 86957 | 86957 | 86957 |
| GM % (NS-B50027-4) | 50 | 10 | 1 | 0.1 | 0.05 | 0.025 |
| NS-B50027-4 oilseed rape GM copies | 43478 | 8695 | 869 | 87 | 43.4 | 21.7 |

PCR was conducted as follows. For PCR assembly: Assemble all reaction (25 µL/reaction) components (New England BioLabs (NEB) Inc., Catalog Log #M0480L) on ice, as illustrated in Table 15.

TABLE 15

PCR reaction assembly

| Components | Volume (µL) |
|---|---|
| 5× OneTaq Standard Reaction Buffer (NEB) | 5.0 |
| 10 mM of each dNTPs | 0.5 |
| 2.5 µM event specific assay mixture (forward and reverse primers mixture) or Internal Reference Gene (HMG) forward and reverse primers mixture | 2.0 |
| OneTaq DNA Polymerase (5 units/µL) (NEB) | 0.2 |
| Template DNA (20 ng/µL) | 5.0 |
| Nuclease-free water | 12.3 |
| Total reaction | 25.0 |

For PCR cycling profile: PCR was used for amplification with the following profile parameters, as described in Table 16.

TABLE 16

PCR cycling profile

| Stage | | Temperature | Time | Cycles |
|---|---|---|---|---|
| 1 | Initial denaturation | 94° C. | 60 sec | 1 |
| 2 | Denaturation | 94° C. | 30 sec | 35 |
| 3 | Annealing | 56° C. | 20 sec | |
| 4 | Elongation | 68° C. | 80 sec | |
| 5 | Final extension | 68° C. | 5 min | 1 |
| 6 | | 10° C. | forever | |

The canola HMG gene is used as the internal reference gene for this qualitative detection method. The Thermo Scientific™ GeneRuler™ Low Range DNA Ladder (ready-to-use) containing a mix of ten chromatography-purified individual DNA fragments (in base pairs: 700, 500, 400, 300, 200, 150, 100, 75, 50, 25) is used as a reference guide. See FIG. 1.

Agarose gel electrophoresis was conducted according to this protocol: For each sample, 10 μL PCR products, 3 μL H₂O and 1 μL loading dye (6x; Thermo Fisher Scientific #R1161) were mixed before loading, and 6 μL DNA Ladder was used. A 2% agarose gel was run at 100 Volts for 60 min. An image of the gel was captured using the Life Technology Image system.

Figure 8:
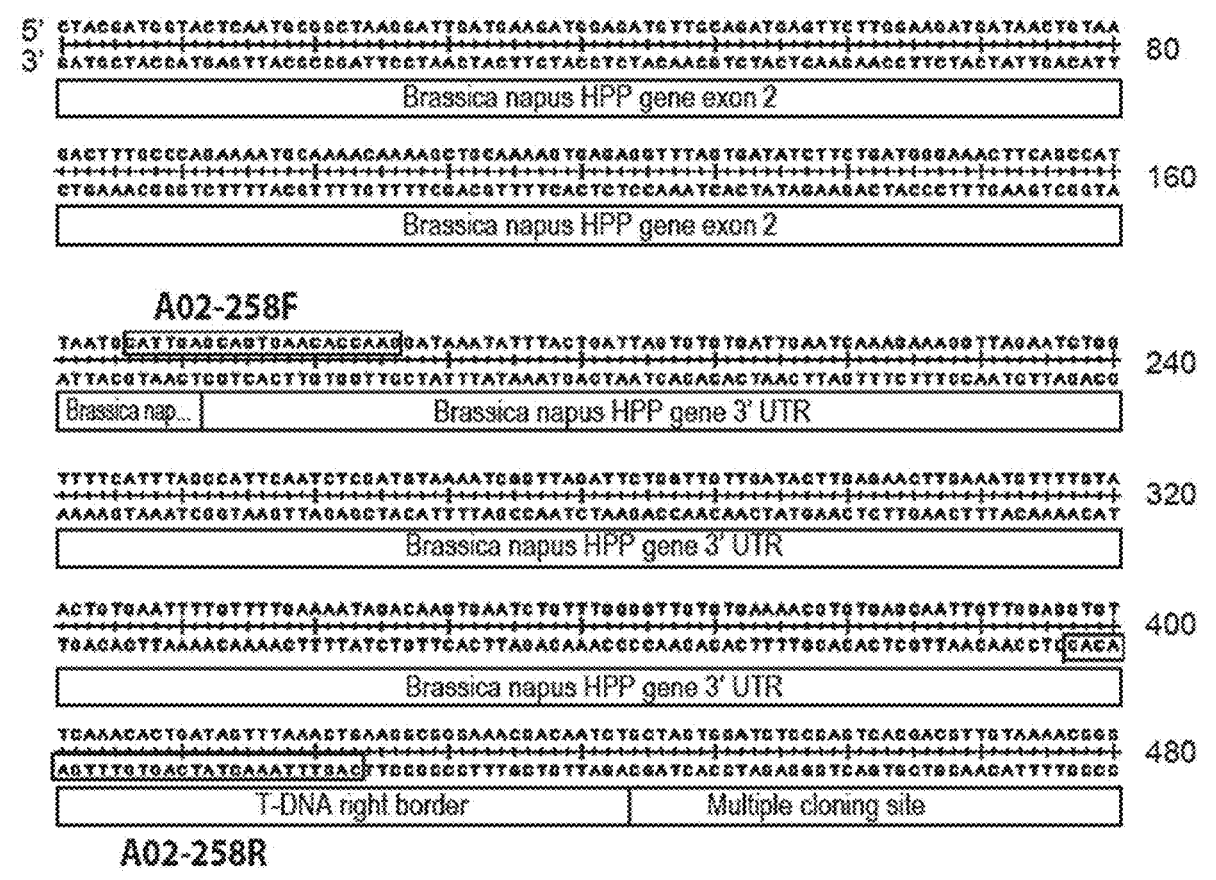
Figure 9:
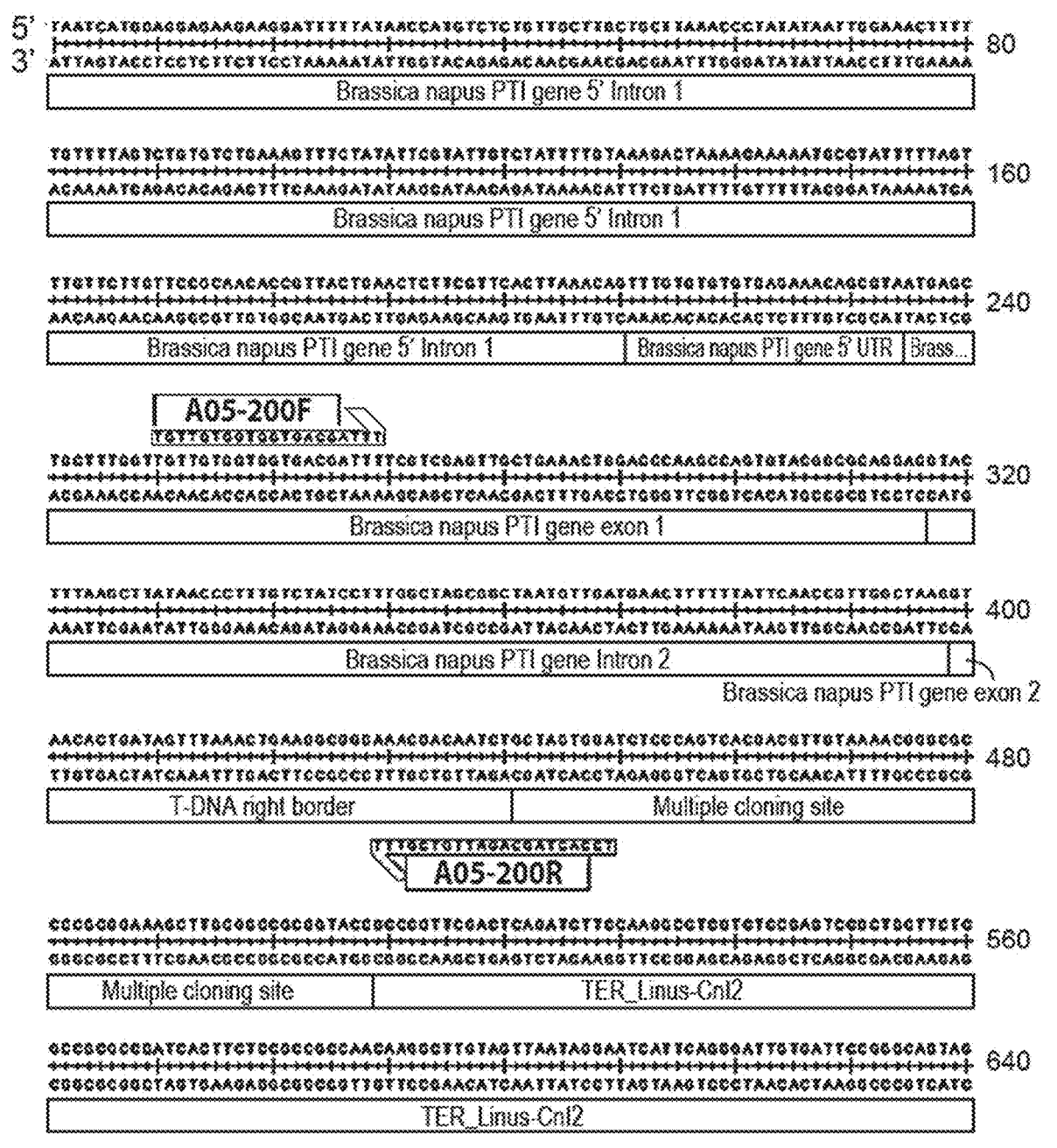

Three primer pairs were employed for this qualitative detection method. The amplicon size for HMG is 206 bp. Assay A02-258 was designed to detect the junction between T-DNA insert and genomic DNA on chromosome A02, and assay A05-200 was designed to detect the junction between T-DNA insert and genomic DNA on chromosome A05. The primer sequences, locations, and product sizes are shown in Table 17, FIG. 8 and FIG. 9. The *Brassica* HMG gene was used as the reference gene for the internal control recommended by Chinese National Standard (MARA 2031-9-2013).

TABLE 17

Primer sequences for assay A05-200, assay A02-258, and HMG

| Name | Sequence | Product size | Target |
|---|---|---|---|
| A05-200F | TGTTGTGGTGGTGACGATTT (SEQ ID NO: 18) | 200 bp | Junction on Chromosome A05 (SEQ ID NO: 27) |
| A05-200R | TCCACTAGCAGATTGTCGTTT (SEQ ID NO: 19) | | |
| A02-258F | CATTGAGCAGTGAACACCAAG (SEQ ID NO: 20) | 258 bp | Junction on Chromosome A02 (SEQ ID NO: 26) |
| A02-258R | CAGTTTAAACTATCAGTGTTTGAACAC (SEQ ID NO: 21) | | |
| Hmg206F | TCCTTCCGTTTCCTCGCC (SEQ ID NO: 22) | 206 bp | Internal reference gene HMG as control |
| Hmg206R | TTCCACGCCCTCTCCGCT (SEQ ID NO: 23) | | |

Samples of 100 ng of genomic DNA template, as provided herein, were subjected to event-specific qualitative PCR (Assay A02-258 for junction in chromosome A02, Assay A05-200 for junction in chromosome A05 and Assay HMG for Reference Gene):

Event NS-50027-4 as positive sample for Assay A02-258 and Assay A05-200;

Receptor canola AV Jade as positive sample for Reference Gene Assay HMG; and

Six different GM spike level samples (Table 14)

Assays A02-258 and A05-200 were tested along with AV Jade, NTC (no template control) and six different DHA canola NS-B50027-4 spike levels (see FIG. 10 and FIG. 11), respectively. In addition, the results from fifteen replicates showed both assays can consistently detect the expected amplicons at least 0.05% spike level (see FIG. 12 and FIG. 13). There was no amplicon from all reactions from AV Jade (a negative control) for event specific assay A02-258 and assay A05-200.

The sample layout of the gel images for FIG. 10-FIG. 13 are described in Tables 18-21, respectively.

TABLE 18

Figure 10:
FIG. 10 is a gel image for assay A02-258 on six different DHA GMO-canola NS-B50027-4 spike samples. The 258-bp amplicon was present in all six different DHA canola NS-B50027-4 spike samples. The 206-bp amplicon generated from the internal reference canola HMG gene was present in AV Jade and HMG-206 spike sample.

Sample layout for assay A02-258 with different DHA GMO-canola NS-spike samples and HMG-206 reference gene as depicted in FIG. 10

| Well | Assay | Sample |
|---|---|---|
| 1 | DNA ladder | DNA ladder |
| 2 | A02-258 | AV Jade |
| 3 | A02-258 | NTC |
| 4 | A02-258 | 100% DHA canola |
| 5 | A02-258 | 50% spike |
| 6 | A02-258 | 10% spike |
| 7 | A02-258 | 1% spike |
| 8 | A02-258 | 0.1% spike |
| 9 | A02-258 | 0.05% spike |
| 10 | A02-258 | 0.025% spike |
| 11 | HMG206 | AV Jade |
| 12 | HMG206 | 0.05% spike |
| 13 | HMG206 | NTC |
| 14 | DNA ladder | DNA ladder |

NTC = no template control

TABLE 19

Figure 11:
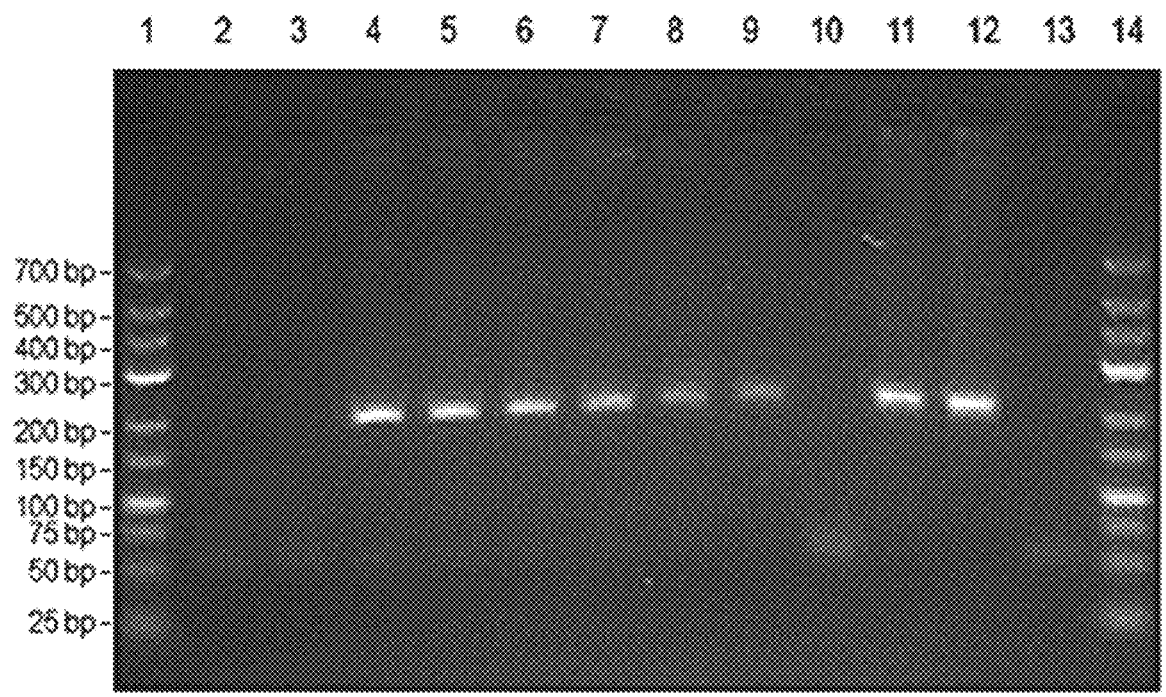
FIG. 11 is a gel image for assay A05-200 on six different DHA GMO-canola NS-B50027-4 spike samples. The 200-bp amplicon was present in all six different DHA GMO-canola NS-B50027-4 spike samples. The 206-bp amplicon generated from the internal reference canola HMG gene was present in AV Jade and HMG-206 spike sample.

Sample layout for assay A05-200 with different DHA GMO-canola NS-B50027-4 spike samples and HMG-206 reference gene as depicted in FIG. 11

| Well | Assay | Sample |
|---|---|---|
| 1 | DNA ladder | DNA ladder |
| 2 | A05-200 | AV Jade |
| 3 | A05-200 | NTC |
| 4 | A05-200 | 100% DHA canola |
| 5 | A05-200 | 50% spike |
| 6 | A05-200 | 10% spike |
| 7 | A05-200 | 1% spike |
| 8 | A05-200 | 0.1% spike |
| 9 | A05-200 | 0.05% spike |
| 10 | A05-200 | 0.025% spike |
| 11 | HMG206 | AV Jade |
| 12 | HMG206 | 0.05% spike |
| 13 | HMG206 | NTC |
| 14 | DNA ladder | DNA ladder |

NTC = no template control

TABLE 20

Figure 12:
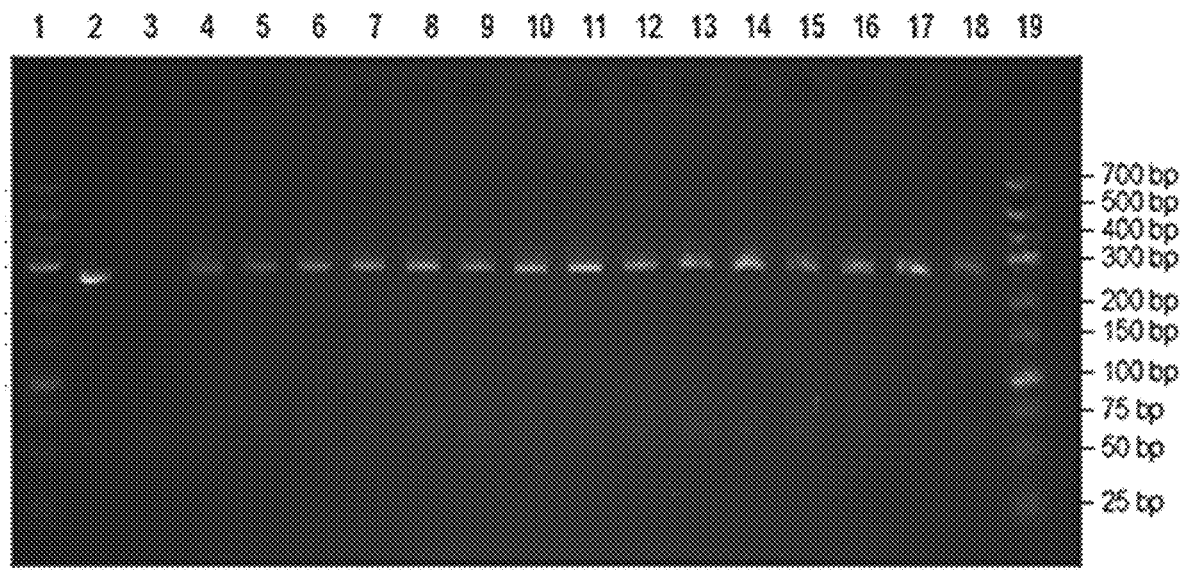
FIG. 12 is a gel image for assay A02-258 showing the 258-bp amplicon was consistently detectable in fifteen replicates of event positive 0.05% spike samples.

Sample layout for assay A02-258 with 15 replicates of event positive 0.05% spike sample as depicted in FIG. 12

| Well | Assay | Sample |
|---|---|---|
| 1 | DNA ladder | DNA ladder |
| 2 | A02-258 | Event Positive 0.1% |
| 3 | A02-258 | AV Jade (control) |
| 4 | A02-258 | Event positive 0.05% |
| 5 | A02-258 | Event positive 0.05% |
| 6 | A02-258 | Event positive 0.05% |
| 7 | A02-258 | Event positive 0.05% |
| 8 | A02-258 | Event positive 0.05% |
| 9 | A02-258 | Event positive 0.05% |
| 10 | A02-258 | Event positive 0.05% |
| 11 | A02-258 | Event positive 0.05% |
| 12 | A02-258 | Event positive 0.05% |
| 13 | A02-258 | Event positive 0.05% |
| 14 | A02-258 | Event positive 0.05% |
| 15 | A02-258 | Event positive 0.05% |
| 16 | A02-258 | Event positive 0.05% |
| 17 | A02-258 | Event positive 0.05% |
| 18 | A02-258 | Event positive 0.05% |
| 19 | DNA ladder | DNA ladder |

TABLE 21

Figure 13:
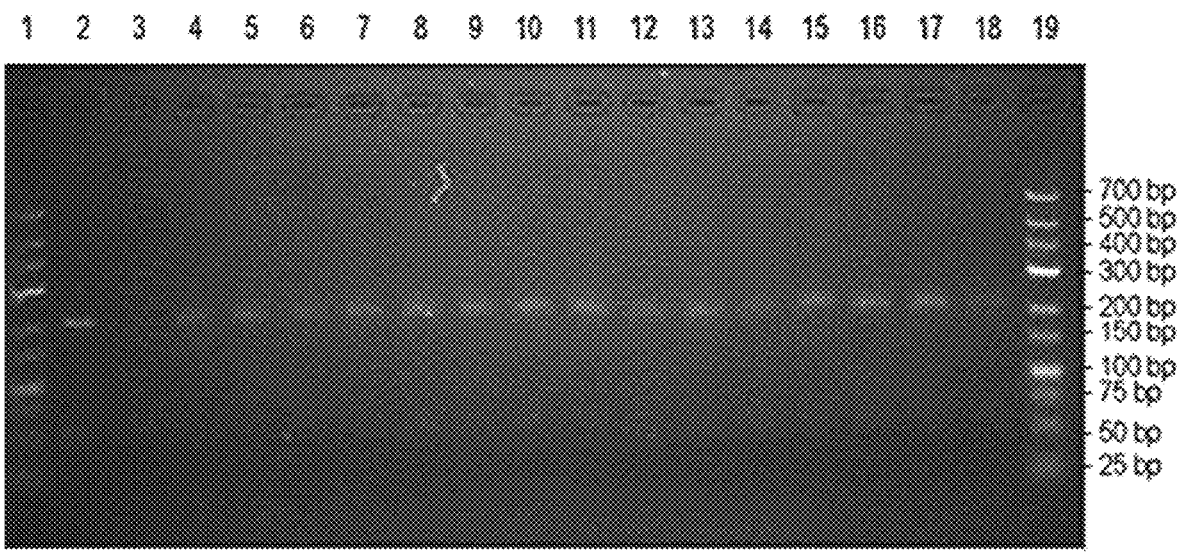
FIG. 13 is a gel image showing for assay A05-200 showing the 200-bp amplicon was consistently detectable in fifteen replicates of event positive 0.05% spike samples.

Sample layout for assay A05-200 with 15 replicates of event positive 0.05% spike sample as depicted in FIG. 13

| Lane | Assay | Sample |
|---|---|---|
| 1 | DNA ladder | DNA ladder |
| 2 | A05-200 | Event Positive 0.1% |
| 3 | A05-200 | AV Jade (control) |
| 4 | A05-200 | Event positive 0.05% |
| 5 | A05-200 | Event positive 0.05% |
| 6 | A05-200 | Event positive 0.05% |
| 7 | A05-200 | Event positive 0.05% |
| 8 | A05-200 | Event positive 0.05% |
| 9 | A05-200 | Event positive 0.05% |
| 10 | A05-200 | Event positive 0.05% |
| 11 | A05-200 | Event positive 0.05% |
| 12 | A05-200 | Event positive 0.05% |
| 13 | A05-200 | Event positive 0.05% |
| 14 | A05-200 | Event positive 0.05% |
| 15 | A05-200 | Event positive 0.05% |
| 16 | A05-200 | Event positive 0.05% |
| 17 | A05-200 | Event positive 0.05% |
| 18 | A05-200 | Event positive 0.05% |
| 19 | DNA ladder | DNA ladder |

The two event specific assays A02-258 and A05-200 were tested with NS-B50027-4 event line DNA at six different spike levels and sensitivity (%) was calculated based on fifteen replicates. All samples containing event NS-B50027-4 DNA from 50% to 0.05% (0.05% equals 43.4 genome copies for NS-B50027-4, see Table 14) showed the expected amplicons consistently from both A02-258 and A05-200 assays. The Limit of Detection (LOD) is at least 0.05% NS-B50027-4 DNA to total DNA or less than 50 genome copies. No amplicon was detected from AV Jade (a negative control) for event-specific assay A02-258 and assay A05-200.

Event-specific gel-based assays A02-258 and A05-200, targeting the two inserts in DHA canola NS-B50027-4 on chromosome A02 and chromosome A05, respectively, have been successfully developed. The assays may be used for adventitious presence testing, trait purity testing, and trait introgression, and to support Nuseed DHA Canola NS-B50027-4 regulatory submission and commercialization.

The specificity of the event-specific A02-258 and A05-200 assays, as discussed above, was further validated by testing twenty-five commercially available GM events (including seven canola events, seven soybean events, seven maize events and four cotton events) from AOCS and seven different non-GM conventional oilseeds varieties. The validation data showed that the assays can detect positive results only from DHA samples. All CRM materials and conventional oilseeds varieties showed negative results for Event NS-B50027-4.

To carry out the validation assays, DNA were extracted from seeds using CTAB DNA extraction as described in Example 1.

Samples of 100 ng genomic DNA template, as described herein, were subjected to event-specific qualitative PCR (assay A02-258 for junction in chromosome A02, assay A05-200 for junction in chromosome A05 and assay HMG for Reference Gene):

Event NS-50027-4 as positive sample for Assay A02-258 and Assay A05-200;

Receptor canola AV Jade as positive sample for Reference Gene Assay HMG;

Non-GM conventional canola varieties selected from Nuseed germplasm pool: NX0026, NX0331, NX0953, NX0980, NX1012, NX1302, NX1306;

Certified Non-Modified Reference Materials (Leaf DNA) purchased from American Oil Chemists' Society (AOCS): Canola 0306-B4, Cotton 0306-A4;

Certified GM Reference Materials (Leaf DNA or seeds powder) purchased from AOCS:

Seven Canola Events: Topas19/2, T45, Rf2, Rf1, Ms8, Ms1, Rf3;

Seven Soybean Events: MON89788, MON87769, MON87708, MON87705, MON87701, FG72, A5547-127;

Seven Maize Events: GA21, MON89034, MIR604, MON88017, MON87427, MON87460, T25;

Four Cotton Events: MON15985-7, MON531, MON1445, GHB614;

The parameters for PCR assembly, PCR cycling profile and primers, as used herein, were identical with those described in Tables 15, 16, and 17, respectively For each sample, 10 μL PCR products, 3 μL $H_2O$, and 1 μL loading dye (6x; Thermo Fisher Scientific #R1161) were mixed before loading, and 6 μL DNA Ladder was used. A 2% agarose gel was run at 100 Volts for 60 minutes. The gel was then photographed using a Life Technology Image system.

Assay A02-258, assay A05-200 and HMG were validated with six different commercial canola GMO events ordered from AOCS. The results showed assay A02-258 (see FIG. 13) and assay A05-200 (see FIG. 14) did not have any amplicons from six commercial canola events. The control gene assay HMG amplified the expected amplicons from these six commercial canola events as expected. The results demonstrated that assay A02-258 and assay A05-200 developed at Nuseed were event-specific for canola. The sample layout for FIG. 14 and FIG. 15 are described in Tables 22 and 23, respectively.

TABLE 22

Figure 14:
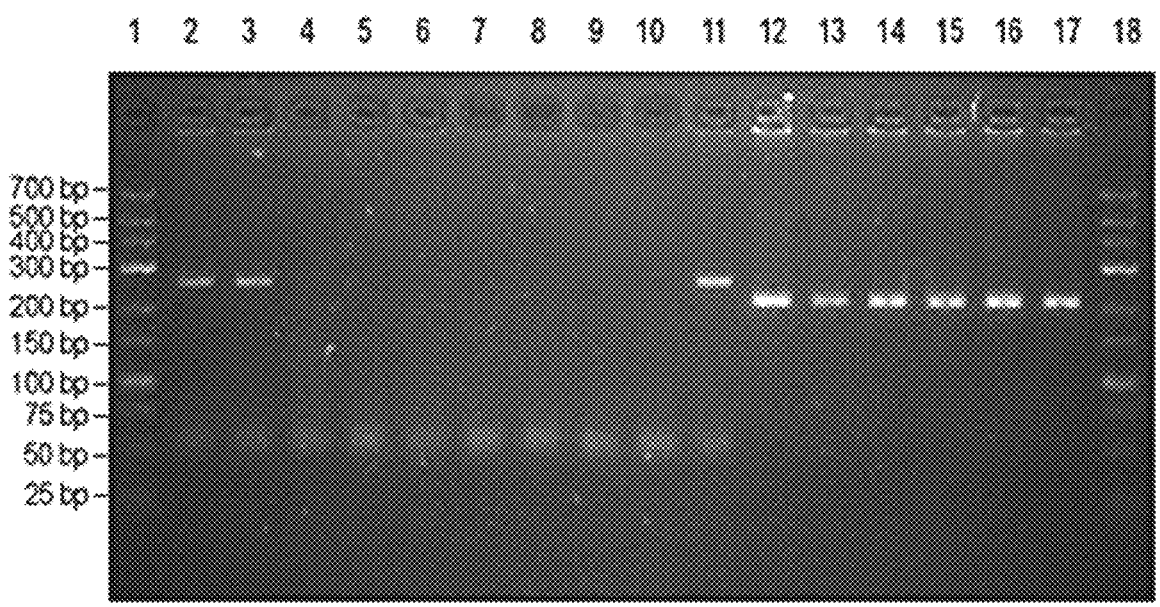
FIG. 14 is a gel image from assay A02-258 plus HMG 206 with six CRM canola events. While the 206-bp amplicon was amplified in six of the commercial canola events, the 258-bp amplicon was not detected.
Figure 15:
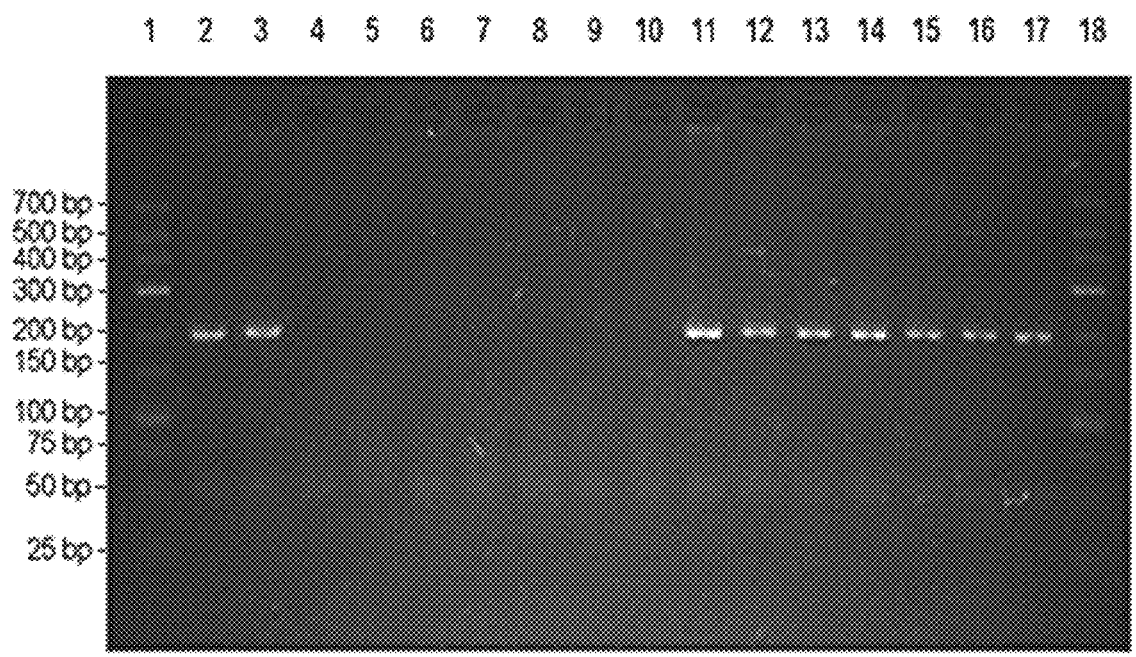
FIG. 15 is a gel image from assay A05-200 plus HMG 206 with six CRM canola events. The 206-bp amplicon was amplified as expectedly in six of the commercial canola events, the 258-bp amplicon however did not.

Sample layout for validation of assay A02-258 plus HMG 206 and six CRM canola events as illustrated in FIG. 14

| Well | Assay | Sample |
|---|---|---|
| 1 | DNA ladder | DNA ladder |
| 2 | A02-258 | DHA Positive |

TABLE 22-continued

Sample layout for validation of assay A02-258 plus HMG 206 and six CRM canola events as illustrated in FIG. 14

| Well | Assay | Sample |
|---|---|---|
| 3 | A02-258 | DHA Positive |
| 4 | A02-258 | AV Jade (control) |
| 5 | A02-258 | Canola event Topas19/2 |
| 6 | A02-258 | Canola event T45 |
| 7 | A02-258 | Canola event Rf2 |
| 8 | A02-258 | Canola event Rf1 |
| 9 | A02-258 | Canola event Ms8 |
| 10 | A02-258 | Canola event Ms1 |
| 11 | A02-258 | DHA Positive |
| 12 | HMG206 | Canola event Topas19/2 |
| 13 | HMG206 | Canola event T45 |
| 14 | HMG206 | Canola event Rf2 |
| 15 | HMG206 | Canola event Rf1 |
| 16 | HMG206 | Canola event Ms8 |
| 17 | HMG206 | Canola event Ms1 |
| 18 | DNA ladder | DNA ladder |

TABLE 23

Sample layout for validation of assay A05-200 plus HMG 206 with six CRM canola events as illustrated in FIG. 15

| Well | Assay | Sample |
|---|---|---|
| 1 | DNA ladder | DNA ladder |
| 2 | A05-200 | DHA Positive |
| 3 | A05-200 | DHA Positive |
| 4 | A05-200 | AV Jade (DHA negative) |
| 5 | A05-200 | Canola event Topas19/2 |
| 6 | A05-200 | Canola event T45 |
| 7 | A05-200 | Canola event Rf2 |
| 8 | A05-200 | Canola event Rf1 |
| 9 | A05-200 | Canola event Ms8 |
| 10 | A05-200 | Canola event Ms1 |
| 11 | A05-200 | DHA Positive |
| 12 | HMG206 | Canola event Topas19/2 |
| 13 | HMG206 | Canola event T45 |
| 14 | HMG206 | Canola event Rf2 |
| 15 | HMG206 | Canola event Rf1 |
| 16 | HMG206 | Canola event Ms8 |
| 17 | HMG206 | Canola event Ms1 |
| 18 | DNA ladder | DNA ladder |

Assay A02-258, assay A05-200 and 5G8 were further validated with all twenty-five different commercial GMO events ordered from AOCS. The results showed assay A02-258 and assay A05-200 did not have any amplicons from all these events, including in seven canola events, seven soybean events, seven maize events, and four cotton events. The DHA canola-positive controls amplified the expected amplicons in the same experiment (see FIG. 16A and FIG. 16B for assay A02-258, and FIG. 17A and FIG. 17B for assay A05-200). The results demonstrated that assay A02-258 and assay A05-200 developed at Nuseed were event-specific for only canola NS-500274 event. The sample layout for FIG. 16A-FIG. 17B are described below in Tables 24A, 24B3, 25A, and 25B3, respectively.

TABLE 24A

Figure 16A:
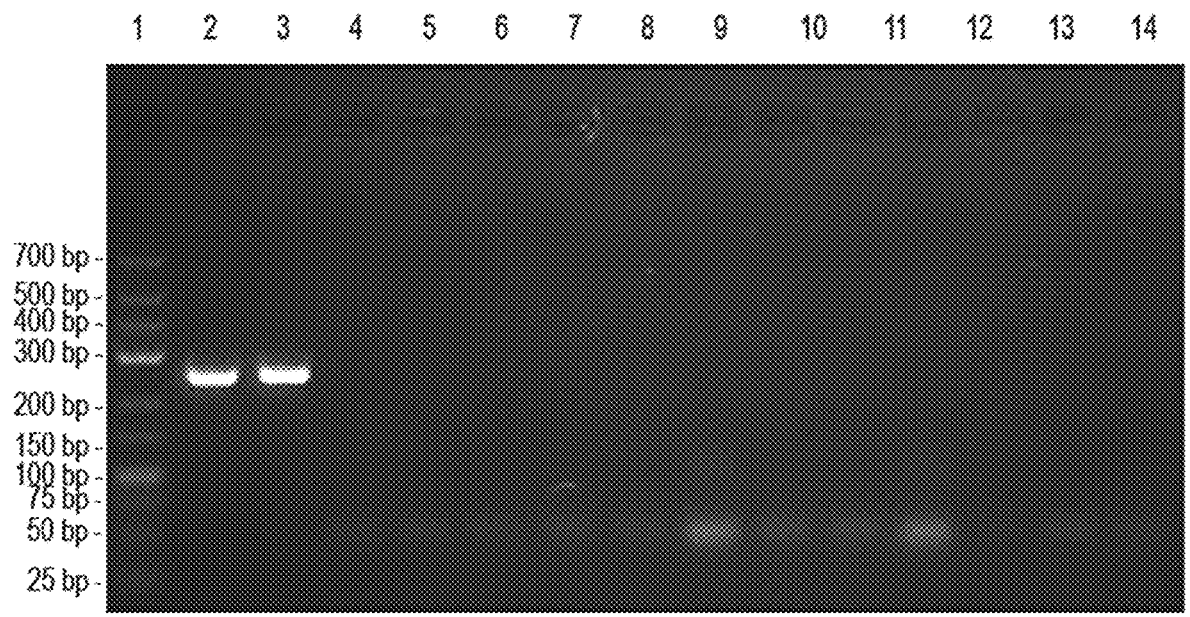
FIGS. 16A and 16B are gel images from assay A02-258 with twenty-five different commercial GMO events ordered from AOCS. The 258-bp amplicon was absent in all of the commercial GMO events tested including canola events, seven soybean events, seven maize events, and four cotton events.
Figure 16B:
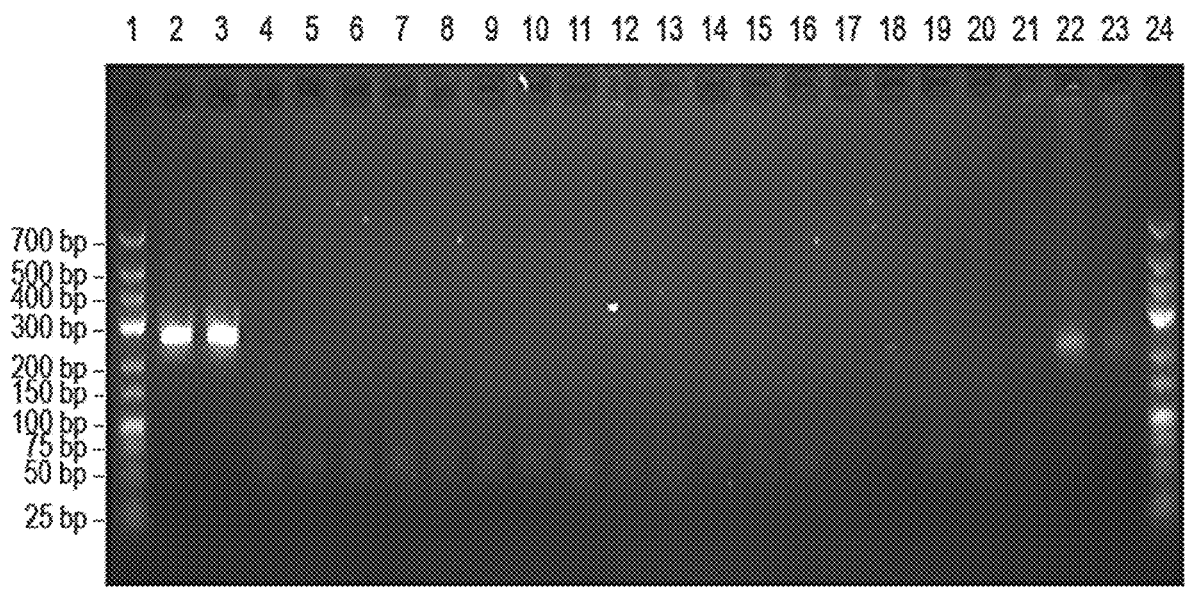

Sample layout for validation of assay A02-258 with 25 Certified GM Reference Materials as illustrated in FIG. 16A

| Well | Assay | Sample |
|---|---|---|
| 1 | DNA ladder | DNA ladder |
| 2 | A02-258 | Event Positive |
| 3 | A02-258 | Event Positive |

TABLE 24A-continued

Sample layout for validation of assay A02-258 with 25 Certified GM Reference Materials as illustrated in FIG. 16A

| Well | Assay | Sample |
|---|---|---|
| 4 | A02-258 | AV Jade (control) |
| 5 | A02-258 | Non-GMO canola 0306-B4 |
| 6 | A02-258 | Canola event Topas19/2 |
| 7 | A02-258 | Canola event T45 |
| 8 | A02-258 | Canola event Rf2 |
| 9 | A02-258 | Canola event Rf1 |
| 10 | A02-258 | Canola event Ms8 |
| 11 | A02-258 | Canola event Ms1 |
| 12 | A02-258 | Canola event Rf3 |
| 13 | A02-258 | Soybean event MON89788 |
| 14 | A02-258 | Soybean event MON87769 |

TABLE 24B

Sample layout for validation of assay A02-258 with 25 Certified GM Reference Materials as illustrated in FIG. 16

| Well | Assay | Sample |
|---|---|---|
| 1 | DNA ladder | DNA ladder |
| 2 | A02-258 | Event Positive |
| 3 | A02-258 | Event Positive |
| 4 | A02-258 | AV Jade (control) |
| 5 | A02-258 | Soybean event MON87708 |
| 6 | A02-258 | Soybean event MON87705 |
| 7 | A02-258 | Soybean event MON87701 |
| 8 | A02-258 | Soybean event FG72 |
| 9 | A02-258 | Soybean event A5547-127 |
| 10 | A02-258 | Maize event GA21 |
| 11 | A02-258 | Maize event MON89034 |
| 12 | A02-258 | Maize event MIR604 |
| 13 | A02-258 | Maize event MON88017 |
| 14 | A02-258 | Maize event MON87427 |
| 15 | A02-258 | Maize event MON 87460 |
| 16 | A02-258 | Maize event T25 |
| 17 | A02-258 | Cotton event MON15985-7 |
| 18 | A02-258 | Cotton event MON531 |
| 19 | A02-258 | Cotton event MON1445 |
| 20 | A02-258 | Non-GMO cotton 0306-A4 |
| 21 | A02-258 | Cotton event GHB614 |
| 22 | HMG206 | Event Positive |
| 23 | HMG206 | Event Negative |
| 24 | DNA ladder | DNA ladder |

TABLE 25A

Figure 17A:
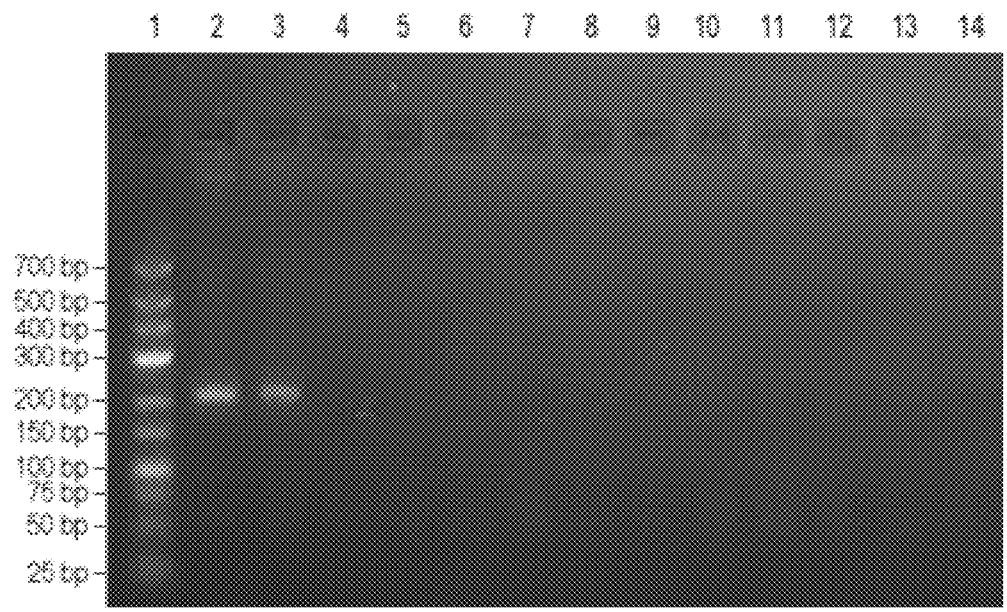
FIGS. 17A and 17B are gel images from assay A05-200 with twenty-five different commercial GMO events ordered from AOCS. The 200-bp amplicon was absent in all of the commercial GMO events tested including canola events, seven soybean events, seven maize events, and four cotton events.

Sample layout for validation of assay A05-200 with 25 Certified GM Reference Materials as illustrated in FIG. 17A

| Well | Assay | Sample |
|---|---|---|
| 1 | DNA ladder | DNA ladder |
| 2 | A05-200 | Event Positive |
| 3 | A05-200 | Event Positive |
| 4 | A05-200 | AV Jade (DHA negative) |
| 5 | A05-200 | Non-GMO canola 0306-B4 |
| 6 | A05-200 | Canola event Topas19/2 |
| 7 | A05-200 | Canola event T45 |
| 8 | A05-200 | Canola event Rf2 |
| 9 | A05-200 | Canola event Rf1 |
| 10 | A05-200 | Canola event Ms8 |
| 11 | A05-200 | Canola event Ms1 |
| 12 | A05-200 | Canola event Rf3 |
| 13 | A05-200 | Soybean event MON89788 |
| 14 | A05-200 | Soybean event MON87769 |

TABLE 25B

Figure 17B:
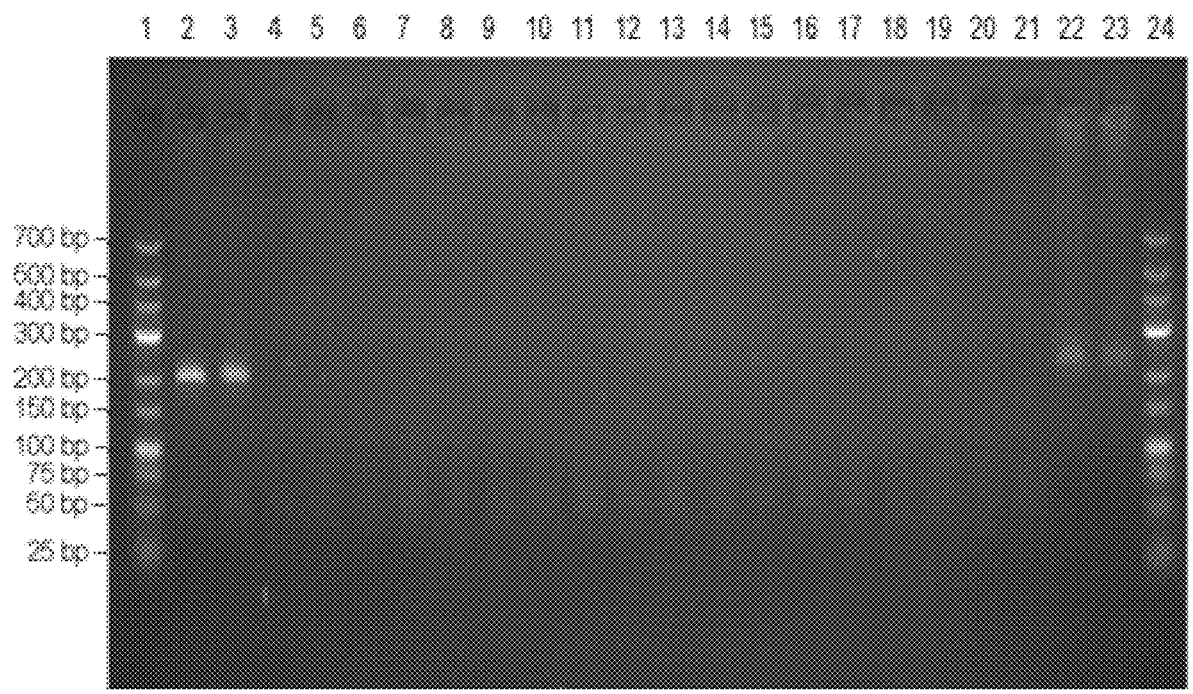

Sample layout for validation of assay A05-200 with 25 Certified GM Reference Materials as illustrated in FIG. 17B

| Well | Assay | Sample |
|---|---|---|
| 1 | DNA ladder | DNA ladder |
| 2 | A05-200 | Event Positive |
| 3 | A05-200 | Event Positive |
| 4 | A05-200 | AV Jade (DHA negative) |
| 5 | A05-200 | Soybean event MON87708 |
| 6 | A05-200 | Soybean event MON87705 |
| 7 | A05-200 | Soybean event MON87701 |
| 8 | A05-200 | Soybean event FG72 |
| 9 | A05-200 | Soybean event A5547-127 |
| 10 | A05-200 | Maize event GA21 |
| 11 | A05-200 | Maize event MON89034 |
| 12 | A05-200 | Maize event MIR604 |
| 13 | A05-200 | Maize event MON88017 |
| 14 | A05-200 | Maize event MON87427 |
| 15 | A05-200 | Maize event MON 87460 |
| 16 | A05-200 | Maize event T25 |
| 17 | A05-200 | Cotton event MON15985-7 |
| 18 | A05-200 | Cotton event MON531 |
| 19 | A05-200 | Cotton event MON1445 |
| 20 | A05-200 | Non-Modified cotton 0306-A4 |
| 21 | A05-200 | Cotton event GHB614 |
| 22 | HMG206 | Event Positive |
| 23 | HMG206 | Event Negative |
| 24 | DNA ladder | DNA ladder |

Assay A02-258 and assay A05-200 were further validated with seven non-GM conventional canola varieties selected from Nuseed germplasm pool with various genetic backgrounds. The results showed that both assays did not amplify any amplicon from these seven non-GM conventional canola varieties (see FIG. 18 for assay A02-258 and FIG. 19 for assay A05-200). Sample layout of FIG. 18 and FIG. 19 are described in Tables 26 and 27, respectively.

TABLE 26

Figure 18:
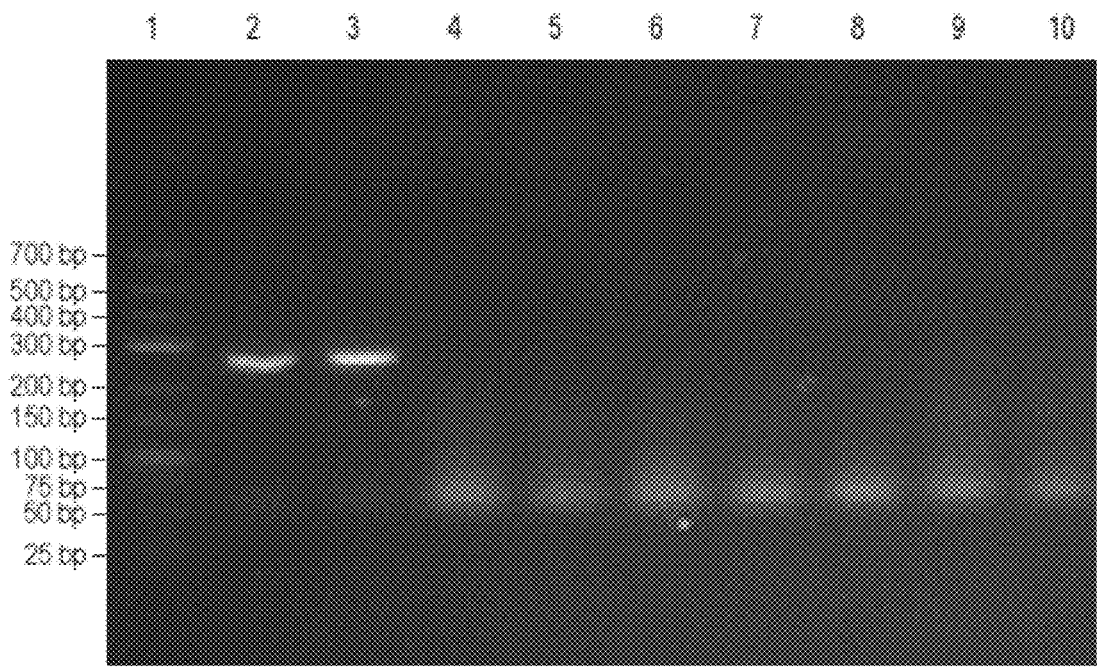
FIG. 18 is a gel image from assay A02-258 tested with seven non-GM conventional canola varieties selected from Nuseed germplasm pool with different genetic backgrounds. Assay A02-258 failed to amplify any amplicon from these seven non-GM conventional canola varieties.
Figure 19:
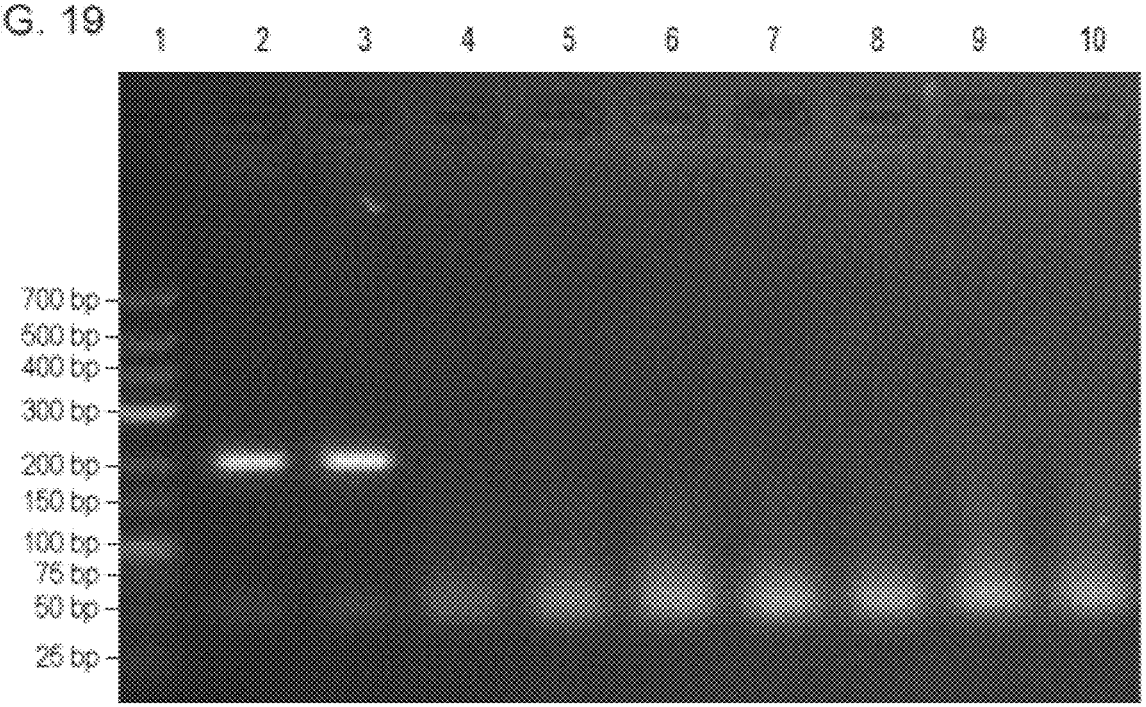
FIG. 19 is a gel image from assay A05-200 tested with seven non-GM conventional canola varieties selected from Nuseed germplasm pool with various genetic backgrounds. Assay A05-200 failed to amplify any amplicon from these seven non-GM conventional canola varieties

Sample layout for validation of assay A02-258 with 7 non-GM conventional canola varieties as illustrated in FIG. 18

| Well | Assay | Sample | Well | Assay | Sample |
|---|---|---|---|---|---|
| 1 | DNA ladder | DNA ladder | 6 | A02-258 | NX0953 |
| 2 | A02-258 | Event Positive | 7 | A02-258 | NX0980 |
| 3 | A02-258 | Event Positive | 8 | A02-258 | NX1012 |
| 4 | A02-258 | NX0026 | 9 | A02-258 | NX1302 |
| 5 | A02-258 | NX0331 | 10 | A02-258 | NX1306 |

TABLE 27

Sample layout for validation of assay A05-200 with 7 non-GM conventional canola varieties as illustrated in FIG. 19

| Well | Assay | Sample | Well | Assay | Sample |
|---|---|---|---|---|---|
| 1 | DNA ladder | DNA ladder | 6 | A05-200 | NX0953 |
| 2 | A05-200 | Event Positive | 7 | A05-200 | NX0980 |
| 3 | A05-200 | Event Positive | 8 | A05-200 | NX1012 |
| 4 | A05-200 | NX0026 | 9 | A05-200 | NX1302 |
| 5 | A05-200 | NX0331 | 10 | A05-200 | NX1306 |

The specificity of these assays was validated from testing twenty-five commercially available GM events (including seven canola events, seven soybean events, seven maize events and four cotton events) from AOCS and 8 different non-GM conventional oilseeds varieties (one from AOCS and seven from Nuseed germplasm pool). Accordingly, the event-specific gel-based assays, A02-258 and A05-200, targeting the two inserts in DHA canola NS-B50027-4 on chromosome A02 and chromosome A05, respectively, were successfully developed and validated. The assays can be used for adventitious presence testing, trait purity testing, and trait introgression, and to support regulatory submission, stewardship, and commercialization.

Example 4. Event-Specific Method for the Quantification of Oilseed Rape NS-B50027-4 Using Real-Time PCR System To determine the relative content of event NS-B50027-4 DNA to total oilseed rape (*Brassica napus*) DNA in a sample, another event-specific real-time quantitative TaqMan® PCR assay was developed. The PCR assay was optimized for use in CFX96 RealTime System Bio-Rad C1000 Touch and the data were analyzed using Bio-Rad CFX manager.

For specific detection of event NS-B50027-4 DNA, two fragments, 120 bp and 170 bp, targeting two insertions on chromosome A05 and A02, respectively, were amplified. The specific fragment of the region that spans the 3' insert-to-plant junction in *B. napus* event NS-B50027-4 was amplified using two specific primers. PCR products were measured during each cycle (real-time) by means of a target-specific oligonucleotide probe labeled with fluorescent dyes FAM™ (6-carboxy-fluorescein, Sigma Aldrich) as a reporter dye at its 5' end and TAMRA™ (carboxytetramethyl-rhodamine, Sigma Aldrich) as a quencher dye at its 3' end. The 5'-nuclease activity of the Taq DNA polymerase was exploited, which resulted in the specific cleavage of the probe, leading to increased fluorescence, which was then monitored.

For relative quantification of event NS-B50027-4 DNA, a *B. napus* specific reference system amplified a 99 bp fragment of HMG endogenous gene (HMGs are nonhistone chromatin-associated proteins), using a pair of HMG gene-specific primers and an HMG gene-specific probe labeled with HEX™ (hexachlorofluorescein, Sigma Aldrich) and TAMRA™

DHA Canola NS-B50027-4 was used as a positive control. AV Jade was used as a negative control. In addition, twenty-seven Certified Reference Materials (CRM) from American Oil Chemists' Society (AOCS) (see Example 1, Table A) were used to validate the assays in the assay development.

Cetyl trimethylammonium bromide (CTAB) DNA extraction method from oilseed rape was previously validated by the EURL GMFF (European Union Reference Laboratory for Genetically Modified Food and Feed). All DNA samples used in subsequent PCR experiments for this Example were extracted using CTAB DNA extraction method, as described above in Example 1.

The standard curves comprised a number of five different GM spike levels: S1 to S5. The first standard curve point S1 was derived from a sample containing the GM 5% of the event: NS-B50027-4. Standard curve points, S2 to S5, were obtained by serial dilution of the 5% GM standard S1. The dilution scheme and the corresponding total genomic DNA content in PCR is described in Table 28:

TABLE 28

Copy number values of the standard curve samples

| Sample code | S1: 5% GM spike | S2: 1% GM spike | S3: 0.5% GM spike | S4: 0.05% GM spike | S5: 0.01% GM spike |
|---|---|---|---|---|---|
| Total amount of DNA in reaction (ng) | 100 | 100 | 100 | 100 | 100 |
| Target taxon HMG copies | 86957 | 86957 | 86957 | 86957 | 86957 |
| GM % (NS-B50027-4) | 5 | 1 | 0.5 | 0.05 | 0.01 |
| NS-B50027-4 oilseed rape GM copies | 4347 | 869 | 434 | 43.4 | 8.7 |

The calibration sample concentrations were used for calculation. The data were analyzed using Bio-Rad CFX manager.

All Taqman reagents were from Fisher Scientific Company LLC. The event-specific assay was designed by Nuseed (Fisher Scientific Customer Design Catalog #4400294). The MG reference gene assay was designed by Nuseed (Fisher Scientific Customer Design Catalog #4467084). The Applied Biosystems™ TaPath™ ProAmp™ Master Mix was from Catalog #A30871 (2×10 ml). All reagents were thawed and stored on ice upon thawing. Each reagent was thoroughly mix before use. To allow for consistency and minimize cross-contamination, PCR was prepared consisting of all components of the PCR, except DNA template, in sufficient quantities for all reactions (including those for standard DNA solutions) to be performed. All reagents were added in the order listed below for both reaction mixes.

PCR reaction assembly for the A02Dn2 and A05Up2 event specific assays and HMG reference gene system was conducted as follows:

TABLE 29

PCR component assembly

| Component | Volume (μl) | Final concentration |
|---|---|---|
| 2x Master mix | 10.0 | 1x |
| Event-specific assay mix (20X) and HMG assay mix (20X) containing forward primer, reverse primer and probe | 1.0 | 1x |
| Forward primer (18 μM) in assay mix | 1.0 | 900 nM |
| Reverse primer (18 μM) in assay mix | 1.0 | 900 nM |
| Probe ((5 μM) in assay mix | 1.0 | 250 nM |
| Template DNA (20 ng/μl) | 5.0 | 5 ng/μl |
| Nuclease-free water | 4.0 | |
| Total reaction volume | 20.0 | |

For PCR cycling profile: CFX96 RealTime System Bio-Rad C1000 Touch was used to run the reaction with the following Taqman PCR profile, similar to the illustrated profile of Table 7, in Example 2.

Two types of quantitation were performed in this method: one for the A02dn2 assay and the other for A05up2 assay. HMG endogenous gene was used as reference gene Three sets of primers (A05up2F (SEQ ID NO:12) and A05up2R (SEQ ID NO:13); A02dn2F (SEQ ID NO:15), and A02dn2R (SEQ ID NO:16); and hmg-F (SEQ ID NO:7) and hmg-R (SEQ ID NO:8) probes A05up2P (SEQ ID NO:14), A02dn2P (SEQ ID NO:17), and hmg-P (SEQ ID NO:11), as provided in Example 2, Table 9, were used in the quantitative assays.

Canola HMG was used as the reference gene for the quantitative detection method. The junction sequences around the T-DNA insertion sites on chromosome A02 and A05 were used for primer and probe design using software Primer3Plus.

The A02 insert downstream junction sequence (totaling 189 bp long (SEQ ID NO:9)) and the A05 insert upstream junction sequence (totaling 226 bp long (SEQ ID NO:10)) used for assay design are described in Example 2. The primer and probe locations of Taqman assays targeting two junctions of the two T-DNA inserts, as used herein, are shown in FIG. 5A (chromosome A02) and FIG. 5B (chromosome A05). The primer sequences are highlighted in light gray, probe sequences are highlighted in medium gray. Sequences in dark gray indicate the complementary sequences of reverse primers below it.

The following equipment was used in this procedure: CFX96 RealTime System Bio-Rad C1000 Touch, Bio-Rad CFX manager, Eppendorf twin.tec PCR plate 96, Thermo Scientific Legend Micro17 Centrifuge and Qubit4 fluorometer from Invitrogen.

The following major reagents, buffers and solutions were used: Applied Biosystems™ TaqPath™ ProAmp™ Master Mix Catalog #A30871; A02dn2 event-specific assay mix (20X) from Fisher Scientific Company LLC; A05up2 event-specific assay mix (20X) from Fisher Scientific Company LLC; HMG reference gene assay mix (20X) from Fisher Scientific Company LLC; CTAB Extraction Buffer (1% CTAB, 0.7 M NaCl, 50 mM Tris-HCl pH 8.0, and 20 mM EDTA pH 8.0); CTAB DNA precipitation buffer (1% CTAB, 50 mM Tris-HCl pH 8.0, 10 mM EDTA pH 8.0); DNase-free RNase and 100% ethanol.

All standard curves for two event-specific assays (assay A02Dn2 and assay A05Up2) were generated with five different GM spike levels –5%, 1%, 0.5%, 0.05% and 0.01% (see FIG. 20 and FIG. 21, respectively). The standard curves for HMG was generated from five different total DNA amount in each reaction-100 ng, 50ng, 5ng, 2.5ng and 0.25ng/per reaction (see FIG. 22). According to current EU method acceptance criteria, the average value of the slope of the standard curve should be within the range of –3.1 to –3.6, and the R square ($R^2$) should be ≥0.98. The data depicted in FIG. 22 show compliance with these criteria.

As indicated in Table 30, the average slope of the standard curve for A02dn2 was –3.3475, and the average slope of the standard curve for A05up2 was –3.3438, respectively, for the event NS-B50027-4. The average slope of the standard curve for HMG assay was –3.3905. The average $R^2$ coefficients from two event-specific assays for the NS-B50027-4 were 0.989 and 0.988, respectively. The average $R^2$ coefficients for HMG was 0.9875. Therefore, all values were within the EU acceptance criteria.

TABLE 30

Summary of the slope, PCR efficiency and R-squared ($R^2$) values obtained from duplicate runs

| Run | A02Dn2 Slope | A02Dn2 PCR efficiency | A02Dn2 R-squared ($R_2$) | A05Up2 Slope | A05Up2 PCR efficiency | A05Up2 R-squared ($R_2$) | HMG Slope | HMG PCR efficiency | HMG R-squared ($R_2$) |
|---|---|---|---|---|---|---|---|---|---|
| A | −3.187 | 106 | 0.986 | −3.323 | 99.9 | 0.989 | −3.491 | 93.4 | 0.988 |
| B | −3.178 | 106.4 | 0.989 | −3.278 | 101.8 | 0.983 | −3.479 | 93.6 | 0.988 |
| C | −3.194 | 105.6 | 0.985 | −3.453 | 94.8 | 0.994 | −3.279 | 99.3 | 0.983 |
| D | −3.596 | 89.7 | 0.998 | −3.254 | 102.9 | 0.982 | −3.465 | 94.3 | 0.981 |
| E | −3.34 | 99.3 | 0.981 | −3.28 | 99.7 | 0.984 | −3.254 | 101.3 | 0.997 |
| F | −3.59 | 89.7 | 0.997 | −3.475 | 94 | 0.996 | −3.375 | 99.9 | 0.988 |
| Mean | −3.3475 | 99.45 | 0.9893 | −3.3438 | 98.85 | 0.988 | −3.3905 | 96.9 | 0.9875 |

The data presented in Table 31 and Table 32, below, show precision and trueness for five GM-levels tested with A02dn2 and A05Up2, respectively. Sixteen GM content values from sixteen replicates for each GM-level were used for RSD (Relative Standard Deviation) and bias calculation. Both parameters were established as being within the EU acceptance criteria (trueness≤25%, RSD≤25% across the entire dynamic range). The LOD (limit of detection) and LOQ (limit of quantification) were determined based on the sixty replicates with 0.05% and 0.01% GM spike level. For 0.05% GM spike level, it can be detected and quantified in all sixty replicates (100%). For 0.01% GM spike level, it can be detected and quantified in fifty-nine out of sixty replicates (98.3%). Accordingly, the LOD for A02dn2 and A05Up2 assays was 0.01% and LOQ was 0.05%. Both LOD and LOQ parameters were established as being within the EU acceptance criteria.

TABLE 31

Precision and trueness for the five GM-levels tested with A02Dn2

| A02Dn2 assay Target GM spike level % | Measured GM levels % | Precision (RSD %) | Bias % (trueness) of the target GM level |
|---|---|---|---|
| 5% GM spike | 0.04653 | 8.69136 | −6.931 |
| 1% GM spike | 1.01052 | 9.04368 | 5.179 |
| 0.5% GM spike | 0.522 | 16.30737 | 4.468 |
| 0.05% GM spike | 0.0510 | 11.4469 | 12.262 |
| 0.01% GM spike | 0.0110 | 18.8051 | 10.0000 |
| Mean | | 12.8588 | 7.768 |

TABLE 32

Precision and trueness for the five GM-levels tested with A05Up2

| A05Up2 assay Target GM spike level % | Measured GM levels % | Precision (RSD %) | Bias % (trueness) of the target GM level |
|---|---|---|---|
| 5% GM spike | 0.05347 | 9.844 | 6.933 |
| 1% GM spike | 1.01044 | 20.089 | 4.374 |
| 0.5% GM spike | 0.00515 | 11.686 | 2.911 |
| 0.05% GM spike | 0.00048 | 9.771 | −4.004 |
| 0.01% GM spike | 0.0110 | 20.50144 | 10.0000 |
| Mean | | 13.5131 | 11.052 |

Results on A02Dn2 assay, more specifically, the amplification plot and standard curves of Runs A, B, C and D with A02Dn2 event-specific assay using different GM spike DNA samples are shown in FIG. 20. In addition, the quantification data from A02dn2 insert specific assay, including the quantification endpoint results, with the standard, unknown and control samples, are provided in Table 33 and Table 34, respectively.

TABLE 33

Quantification Cq results-Raw data from assay A02dn2

| Well | Fluor | Target | Content | Sample | Cq Mean | Cq Std. Dev | Starting Quantity (SQ) |
|---|---|---|---|---|---|---|---|
| A01 | FAM | A02Dn2 | Std-1 | 5% | 26.48 | 0.087 | 0.05000 |
| A02 | FAM | A02Dn2 | Std-1 | 5% | 26.48 | 0.087 | 0.05000 |
| A03 | FAM | A02Dn2 | Std-1 | 5% | 26.48 | 0.087 | 0.05000 |
| A04 | FAM | A02Dn2 | Std-1 | 5% | 26.48 | 0.087 | 0.05000 |
| A05 | FAM | A02Dn2 | Unkn | 5% | 26.37 | 0.000 | 0.04435 |
| A06 | FAM | A02Dn2 | Unkn | 5% | 26.44 | 0.000 | 0.04219 |
| A07 | FAM | A02Dn2 | Unkn | 5% | 26.39 | 0.000 | 0.04351 |
| A08 | FAM | A02Dn2 | Unkn | 5% | 26.30 | 0.000 | 0.04650 |
| A09 | FAM | A02Dn2 | Unkn | 5% | 26.37 | 0.000 | 0.04417 |
| A10 | FAM | A02Dn2 | Unkn | 5% | 26.36 | 0.000 | 0.04466 |
| A11 | FAM | A02Dn2 | Unkn | 5% | 26.44 | 0.000 | 0.04192 |
| A12 | FAM | A02Dn2 | Unkn | 5% | 26.61 | 0.000 | 0.03725 |
| A01 | FAM | A02Dn2 | Unkn | 5% | 25.07 | 0.049 | 0.05000 |
| A02 | FAM | A02Dn2 | Unkn | 5% | 25.07 | 0.049 | 0.05000 |
| A03 | FAM | A02Dn2 | Unkn | 5% | 25.07 | 0.049 | 0.05000 |
| A04 | FAM | A02Dn2 | Unkn | 5% | 25.07 | 0.049 | 0.05000 |
| B01 | FAM | A02Dn2 | Std-2 | 1% | 28.33 | 0.075 | 0.01000 |
| B02 | FAM | A02Dn2 | Std-2 | 1% | 28.33 | 0.075 | 0.01000 |
| B03 | FAM | A02Dn2 | Std-2 | 1% | 28.33 | 0.075 | 0.01000 |
| B04 | FAM | A02Dn2 | Std-2 | 1% | 28.33 | 0.075 | 0.01000 |
| B05 | FAM | A02Dn2 | Unkn | 1% | 28.10 | 0.000 | 0.01259 |
| B06 | FAM | A02Dn2 | Unkn | 1% | 28.27 | 0.000 | 0.01120 |
| B07 | FAM | A02Dn2 | Unkn | 1% | 28.18 | 0.000 | 0.01196 |
| B08 | FAM | A02Dn2 | Unkn | 1% | 28.23 | 0.000 | 0.01151 |
| B09 | FAM | A02Dn2 | Unkn | 1% | 28.24 | 0.000 | 0.01138 |
| B10 | FAM | A02Dn2 | Unkn | 1% | 28.31 | 0.000 | 0.01084 |
| B11 | FAM | A02Dn2 | Unkn | 1% | 28.45 | 0.000 | 0.00980 |
| B12 | FAM | A02Dn2 | Unkn | 1% | 28.57 | 0.000 | 0.00902 |
| B01 | FAM | A02Dn2 | Unkn | 1% | 27.68 | 0.207 | 0.01000 |
| B02 | FAM | A02Dn2 | Unkn | 1% | 27.68 | 0.207 | 0.01000 |
| B03 | FAM | A02Dn2 | Unkn | 1% | 27.68 | 0.207 | 0.01000 |
| B04 | FAM | A02Dn2 | Unkn | 1% | 27.68 | 0.207 | 0.01000 |
| C01 | FAM | A02Dn2 | Std-3 | 0.5% | 29.16 | 0.317 | 0.0050000 |
| C02 | FAM | A02Dn2 | Std-3 | 0.5% | 29.16 | 0.317 | 0.0050000 |
| C03 | FAM | A02Dn2 | Std-3 | 0.5% | 29.16 | 0.317 | 0.0050000 |
| C04 | FAM | A02Dn2 | Std-3 | 0.5% | 29.16 | 0.317 | 0.0050000 |
| C05 | FAM | A02Dn2 | Unkn | 0.5% | 29.38 | 0.000 | 0.0050064 |
| C06 | FAM | A02Dn2 | Unkn | 0.5% | 29.47 | 0.000 | 0.0046746 |
| C07 | FAM | A02Dn2 | Unkn | 0.5% | 27.23 | 0.000 | 0.0043643 |
| C08 | FAM | A02Dn2 | Unkn | 0.5% | 28.73 | 0.000 | 0.0080038 |
| C09 | FAM | A02Dn2 | Unkn | 0.5% | 29.07 | 0.000 | 0.0062590 |
| C10 | FAM | A02Dn2 | Unkn | 0.5% | 29.20 | 0.000 | 0.0056882 |
| C11 | FAM | A02Dn2 | Unkn | 0.5% | 29.43 | 0.000 | 0.0048110 |
| C12 | FAM | A02Dn2 | Unkn | 0.5% | 29.45 | 0.000 | 0.0047668 |
| C01 | FAM | A02Dn2 | Unkn | 0.5% | 28.62 | 0.095 | 0.00500 |
| C02 | FAM | A02Dn2 | Unkn | 0.5% | 28.62 | 0.095 | 0.00500 |
| C03 | FAM | A02Dn2 | Unkn | 0.5% | 28.62 | 0.095 | 0.00500 |
| C04 | FAM | A02Dn2 | Unkn | 0.5% | 28.62 | 0.095 | 0.00500 |
| D01 | FAM | A02Dn2 | Std-4 | 0.05% | 32.27 | 0.288 | 0.00050 |
| D02 | FAM | A02Dn2 | Std-4 | 0.05% | 32.27 | 0.288 | 0.00050 |
| D03 | FAM | A02Dn2 | Std-4 | 0.05% | 32.27 | 0.288 | 0.00050 |
| D04 | FAM | A02Dn2 | Std-4 | 0.05% | 32.27 | 0.288 | 0.00050 |
| D05 | FAM | A02Dn2 | Unkn | 0.05% | 32.77 | 0.000 | 0.00043 |
| D06 | FAM | A02Dn2 | Unkn | 0.05% | 32.48 | 0.000 | 0.00053 |

TABLE 33-continued

Quantification Cq results-Raw data from assay A02dn2

| Well | Fluor | Target | Content | Sample | Cq | Cq Mean | Cq Std. Dev | Starting Quantity (SQ) |
|---|---|---|---|---|---|---|---|---|
| D07 | FAM | A02Dn2 | Unkn | 0.05% | 32.33 | | 0.000 | 0.00059 |
| D08 | FAM | A02Dn2 | Unkn | 0.05% | 32.40 | | 0.000 | 0.00056 |
| D09 | FAM | A02Dn2 | Unkn | 0.05% | 32.53 | | 0.000 | 0.00051 |
| D10 | FAM | A02Dn2 | Unkn | 0.05% | 32.29 | | 0.000 | 0.00061 |
| D11 | FAM | A02Dn2 | Unkn | 0.05% | 32.73 | | 0.000 | 0.00044 |
| D12 | FAM | A02Dn2 | Unkn | 0.05% | 32.77 | | 0.000 | 0.00043 |
| D01 | FAM | A02Dn2 | Unkn | 0.05% | 32.14 | 0.124 | | 0.00050 |
| D02 | FAM | A02Dn2 | Unkn | 0.05% | 32.14 | 0.124 | | 0.00050 |
| D03 | FAM | A02Dn2 | Unkn | 0.05% | 32.14 | 0.124 | | 0.00050 |
| D04 | FAM | A02Dn2 | Unkn | 0.05% | 32.14 | 0.124 | | 0.00050 |
| A05 | FAM | A02Dn2 | Unkn | 0.01% | 36.64 | | 0.000 | 0.00013 |
| A06 | FAM | A02Dn2 | Unkn | 0.01% | 36.88 | | 0.000 | 0.00011 |
| A07 | FAM | A02Dn2 | Unkn | 0.01% | 37.34 | | 0.000 | 0.00008 |
| A08 | FAM | A02Dn2 | Unkn | 0.01% | 36.65 | | 0.000 | 0.00013 |
| B05 | FAM | A02Dn2 | Unkn | 0.01% | 35.38 | | 0.000 | 0.00011 |
| B06 | FAM | A02Dn2 | Unkn | 0.01% | 37.02 | | 0.000 | 0.00010 |
| B07 | FAM | A02Dn2 | Unkn | 0.01% | 36.20 | | 0.000 | 0.00013 |
| B08 | FAM | A02Dn2 | Unkn | 0.01% | 36.74 | | 0.000 | 0.00012 |
| C05 | FAM | A02Dn2 | Unkn | 0.01% | 37.03 | | 0.000 | 0.00010 |
| C06 | FAM | A02Dn2 | Unkn | 0.01% | 37.06 | | 0.000 | 0.00010 |
| C07 | FAM | A02Dn2 | Unkn | 0.01% | 37.00 | | 0.000 | 0.00010 |
| C08 | FAM | A02Dn2 | Unkn | 0.01% | 36.94 | | 0.000 | 0.00010 |
| D05 | FAM | A02Dn2 | Unkn | 0.01% | 36.39 | | 0.000 | 0.00015 |
| D06 | FAM | A02Dn2 | Unkn | 0.01% | 37.20 | | 0.000 | 0.00009 |
| D07 | FAM | A02Dn2 | Unkn | 0.01% | 36.49 | | 0.000 | 0.00014 |
| D08 | FAM | A02Dn2 | Unkn | 0.01% | 36.49 | | 0.000 | 0.00014 |
| E05 | FAM | A02Dn2 | Unkn | 0.01% | 36.56 | | 0.000 | 0.00014 |
| E06 | FAM | A02Dn2 | Unkn | 0.01% | 36.70 | | 0.000 | 0.00012 |
| E07 | FAM | A02Dn2 | Unkn | 0.01% | 37.07 | | 0.000 | 0.00010 |
| E08 | FAM | A02Dn2 | Unkn | 0.01% | 37.15 | | 0.000 | 0.00009 |
| F01 | FAM | A02Dn2 | Neg Ctrl | AV Jade | 39.86 | | 0.000 | 0.00000 |
| F02 | FAM | A02Dn2 | Neg Ctrl | AV Jade | 0.00 | | 0.000 | |
| F03 | FAM | A02Dn2 | Neg Ctrl | AV Jade | 39.72 | | 0.000 | 0.00000 |
| F04 | FAM | A02Dn2 | Neg Ctrl | AV Jade | 0.00 | | 0.000 | |
| G01 | FAM | A02Dn2 | NTC | NTC | 0.00 | | 0.000 | |
| G02 | FAM | A02Dn2 | NTC | NTC | 0.00 | | 0.000 | |
| G03 | FAM | A02Dn2 | NTC | NTC | 0.00 | | 0.000 | |
| G04 | FAM | A02Dn2 | NTC | NTC | 0.00 | | 0.000 | |
| H09 | FAM | A02Dn2 | Unkn | NTC | 0.00 | | 0.000 | |
| H10 | FAM | A02Dn2 | Unkn | NTC | 0.00 | | 0.000 | |
| H11 | FAM | A02Dn2 | Unkn | NTC | 0.00 | | 0.000 | |
| H12 | FAM | A02Dn2 | Unkn | NTC | 0.00 | | 0.000 | |

Std = Standard; Unkn = Unknown; Neg Ctrl = Negative Control; NTC = No Template Control

TABLE 34

Quantification endpoint results from A02Dn2

| Well | Fluor | Target | Content | Sample | End RFU | Call |
|---|---|---|---|---|---|---|
| A01 | FAM | A02Dn2 | Std-1 | 5% | 5219.33 | (+) Positive |
| A02 | FAM | A02Dn2 | Std-1 | 5% | 5280.07 | (+) Positive |
| A03 | FAM | A02Dn2 | Std-1 | 5% | 5469.80 | (+) Positive |
| A04 | FAM | A02Dn2 | Std-1 | 5% | 5470.10 | (+) Positive |
| A05 | FAM | A02Dn2 | Unkn | 5% | 5707.73 | (+) Positive |
| A06 | FAM | A02Dn2 | Unkn | 5% | 5353.81 | (+) Positive |
| A07 | FAM | A02Dn2 | Unkn | 5% | 5537.41 | (+) Positive |
| A08 | FAM | A02Dn2 | Unkn | 5% | 5684.18 | (+) Positive |
| A09 | FAM | A02Dn2 | Unkn | 5% | 5683.21 | (+) Positive |
| A10 | FAM | A02Dn2 | Unkn | 5% | 5602.37 | (+) Positive |
| A11 | FAM | A02Dn2 | Unkn | 5% | 5682.00 | (+) Positive |
| A12 | FAM | A02Dn2 | Unkn | 5% | 5360.75 | (+) Positive |
| B01 | FAM | A02Dn2 | Std-2 | 1% | 5162.86 | (+) Positive |
| B02 | FAM | A02Dn2 | Std-2 | 1% | 5380.40 | (+) Positive |
| B03 | FAM | A02Dn2 | Std-2 | 1% | 5277.12 | (+) Positive |
| B04 | FAM | A02Dn2 | Std-2 | 1% | 5374.85 | (+) Positive |
| B05 | FAM | A02Dn2 | Unkn | 1% | 5465.50 | (+) Positive |
| B06 | FAM | A02Dn2 | Unkn | 1% | 5356.57 | (+) Positive |
| B07 | FAM | A02Dn2 | Unkn | 1% | 5405.85 | (+) Positive |
| B08 | FAM | A02Dn2 | Unkn | 1% | 5551.61 | (+) Positive |
| B09 | FAM | A02Dn2 | Unkn | 1% | 5575.64 | (+) Positive |
| B10 | FAM | A02Dn2 | Unkn | 1% | 5559.72 | (+) Positive |
| B11 | FAM | A02Dn2 | Unkn | 1% | 5582.38 | (+) Positive |
| B12 | FAM | A02Dn2 | Unkn | 1% | 5328.60 | (+) Positive |
| C01 | FAM | A02Dn2 | Std-3 | 0.5% | 5032.21 | (+) Positive |
| C02 | FAM | A02Dn2 | Std-3 | 0.5% | 5646.87 | (+) Positive |
| C03 | FAM | A02Dn2 | Std-3 | 0.5% | 5370.98 | (+) Positive |
| C04 | FAM | A02Dn2 | Std-3 | 0.5% | 5316.61 | (+) Positive |
| C05 | FAM | A02Dn2 | Unkn | 0.5% | 5233.61 | (+) Positive |
| C06 | FAM | A02Dn2 | Unkn | 0.5% | 5255.56 | (+) Positive |
| C07 | FAM | A02Dn2 | Unkn | 0.5% | 5655.98 | (+) Positive |
| C08 | FAM | A02Dn2 | Unkn | 0.5% | 5676.26 | (+) Positive |
| C09 | FAM | A02Dn2 | Unkn | 0.5% | 5517.06 | (+) Positive |
| C10 | FAM | A02Dn2 | Unkn | 0.5% | 5314.73 | (+) Positive |
| C11 | FAM | A02Dn2 | Unkn | 0.5% | 5367.68 | (+) Positive |
| C12 | FAM | A02Dn2 | Unkn | 0.5% | 5333.90 | (+) Positive |
| D01 | FAM | A02Dn2 | Std-4 | 0.05% | 4261.66 | (+) Positive |
| D02 | FAM | A02Dn2 | Std-4 | 0.05% | 4439.37 | (+) Positive |
| D03 | FAM | A02Dn2 | Std-4 | 0.05% | 4759.59 | (+) Positive |
| D04 | FAM | A02Dn2 | Std-4 | 0.05% | 4360.87 | (+) Positive |
| D05 | FAM | A02Dn2 | Unkn | 0.05% | 4275.04 | (+) Positive |
| D06 | FAM | A02Dn2 | Unkn | 0.05% | 4429.87 | (+) Positive |
| D07 | FAM | A02Dn2 | Unkn | 0.05% | 4538.26 | (+) Positive |
| D08 | FAM | A02Dn2 | Unkn | 0.05% | 4502.55 | (+) Positive |
| D09 | FAM | A02Dn2 | Unkn | 0.05% | 4568.84 | (+) Positive |
| D10 | FAM | A02Dn2 | Unkn | 0.05% | 4462.56 | (+) Positive |
| D11 | FAM | A02Dn2 | Unkn | 0.05% | 4306.42 | (+) Positive |
| D12 | FAM | A02Dn2 | Unkn | 0.05% | 4369.32 | (+) Positive |
| E01 | FAM | A02Dn2 | Std-5 | 0.01% | 2805.34 | (+) Positive |
| E02 | FAM | A02Dn2 | Std-5 | 0.01% | 3085.78 | (+) Positive |
| E03 | FAM | A02Dn2 | Std-5 | 0.01% | 2924.08 | (+) Positive |
| E04 | FAM | A02Dn2 | Std-5 | 0.01% | 2787.59 | (+) Positive |
| E05 | FAM | A02Dn2 | Unkn | NTC | -2.92 | |
| E06 | FAM | A02Dn2 | Unkn | NTC | -3.74 | |
| E07 | FAM | A02Dn2 | Unkn | NTC | -2.59 | |
| E08 | FAM | A02Dn2 | Unkn | NTC | -2.08 | |
| F01 | FAM | A02Dn2 | Neg Ctrl | AV Jade | -14.61 | |
| F02 | FAM | A02Dn2 | Neg Ctrl | AV Jade | -2.62 | |
| F03 | FAM | A02Dn2 | Neg Ctrl | AV Jade | 7.83 | |
| F04 | FAM | A02Dn2 | Neg Ctrl | AV Jade | -0.05 | |
| F05 | FAM | A02Dn2 | Neg Ctrl | AV Jade | -3.68 | |
| F06 | FAM | A02Dn2 | Neg Ctrl | AV Jade | -4.31 | |
| F07 | FAM | A02Dn2 | Neg Ctrl | AV Jade | -3.17 | |
| F08 | FAM | A02Dn2 | Neg Ctrl | AV Jade | -1.26 | |

Std = Standard; Unkn = Unknown; Neg Ctrl = Negative Control; NTC = No Template Control Results on A05Up2 assay, more specifically, the amplification plot and standard curves of Runs A, B, C and D with A05Up2 event specific assay using different GM spike DNA samples, are shown in FIG. 21. The quantification data from A05Up2 insert specific assay, including the quantification endpoint results, with the standard, unknown and control samples, are provided in Tables 35 and 36, respectively.

TABLE 35

Quantification Cq results-Raw data from assay A05Up2

| Well | Fluor | Target | Content | Sample | Cq | Cq Mean | Cq Std. Dev | Starting Quantity (SQ) |
|---|---|---|---|---|---|---|---|---|
| F01 | FAM | A05up2 | Neg Ctrl | NTC | | 0.00 | 0.000 | |
| F02 | FAM | A05up2 | Neg Ctrl | NTC | | 0.00 | 0.000 | |
| F03 | FAM | A05up2 | Neg Ctrl | NTC | | 0.00 | 0.000 | |
| F04 | FAM | A05up2 | Neg Ctrl | NTC | 40.19 | 40.19 | 0.000 | 0.00000 |
| G01 | FAM | A05up2 | NTC | NTC | 38.93 | 38.93 | 0.000 | |
| G02 | FAM | A05up2 | NTC | NTC | | 0.00 | 0.000 | |
| G03 | FAM | A05up2 | NTC | NTC | | 0.00 | 0.000 | |
| G04 | FAM | A05up2 | NTC | NTC | | 0.00 | 0.000 | |
| E05 | FAM | A05up2 | Neg Ctrl | AV Jade | | 0.00 | 0.000 | |
| E06 | FAM | A05up2 | Neg Ctrl | AV Jade | | 0.00 | 0.000 | |
| E07 | FAM | A05up2 | Neg Ctrl | AV Jade | | 0.00 | 0.000 | |
| E08 | FAM | A05up2 | Neg Ctrl | AV Jade | | 0.00 | 0.000 | |

TABLE 35-continued

Quantification Cq results-Raw data from assay A05Up2

| Well | Fluor | Target | Content | Sample | Cq | Cq Mean | Cq Std. Dev | Starting Quantity (SQ) |
|---|---|---|---|---|---|---|---|---|
| F05 | FAM | A05up2 | Neg Ctrl | AV Jade |  | 0.00 | 0.000 |  |
| F06 | FAM | A05up2 | Neg Ctrl | AV Jade |  | 0.00 | 0.000 |  |
| F07 | FAM | A05up2 | Neg Ctrl | AV Jade |  | 0.00 | 0.000 |  |
| F08 | FAM | A05up2 | Neg Ctrl | AV Jade |  | 0.00 | 0.000 |  |
| A01 | FAM | A05up2 | Std-1 | 5% | 24.81 | 25.03 | 0.184 | 0.05000 |
| A02 | FAM | A05up2 | Std-1 | 5% | 25.24 | 25.03 | 0.184 | 0.05000 |
| A03 | FAM | A05up2 | Std-1 | 5% | 25.10 | 25.03 | 0.184 | 0.05000 |
| A04 | FAM | A05up2 | Std-1 | 5% | 24.97 | 25.03 | 0.184 | 0.05000 |
| A05 | FAM | A05up2 | Unkn | 5% | 24.99 | 24.99 | 0.000 | 0.05422 |
| A06 | FAM | A05up2 | Unkn | 5% | 24.76 | 24.76 | 0.000 | 0.06289 |
| A07 | FAM | A05up2 | Unkn | 5% | 24.77 | 24.77 | 0.000 | 0.06264 |
| A08 | FAM | A05up2 | Unkn | 5% | 24.83 | 24.83 | 0.000 | 0.06011 |
| A09 | FAM | A05up2 | Unkn | 5% | 25.06 | 25.06 | 0.000 | 0.05173 |
| A10 | FAM | A05up2 | Unkn | 5% | 24.78 | 24.78 | 0.000 | 0.06221 |
| A11 | FAM | A05up2 | Unkn | 5% | 25.02 | 25.02 | 0.000 | 0.05290 |
| A12 | FAM | A05up2 | Unkn | 5% | 25.14 | 25.14 | 0.000 | 0.04877 |
| A01 | FAM | A05up2 | Unkn | 5% | 25.47 | 25.47 | 0.000 | 0.05000 |
| A02 | FAM | A05up2 | Unkn | 5% | 25.51 | 25.51 | 0.000 | 0.05000 |
| A03 | FAM | A05up2 | Unkn | 5% | 25.44 | 25.44 | 0.000 | 0.05000 |
| A04 | FAM | A05up2 | Unkn | 5% | 25.50 | 25.50 | 0.000 | 0.05000 |
| B01 | FAM | A05up2 | Std-2 | 1% | 27.86 | 27.67 | 0.214 | 0.01000 |
| B02 | FAM | A05up2 | Std-2 | 1% | 27.37 | 27.67 | 0.214 | 0.01000 |
| B03 | FAM | A05up2 | Std-2 | 1% | 27.72 | 27.67 | 0.214 | 0.01000 |
| B04 | FAM | A05up2 | Std-2 | 1% | 27.75 | 27.67 | 0.214 | 0.01000 |
| B05 | FAM | A05up2 | Unkn | 1% | 27.63 | 27.63 | 0.000 | 0.00932 |
| B06 | FAM | A05up2 | Unkn | 1% | 26.66 | 26.66 | 0.000 | 0.01770 |
| B07 | FAM | A05up2 | Unkn | 1% | 27.71 | 27.71 | 0.000 | 0.00880 |
| B08 | FAM | A05up2 | Unkn | 1% | 27.42 | 27.42 | 0.000 | 0.01068 |
| B09 | FAM | A05up2 | Unkn | 1% | 27.26 | 27.26 | 0.000 | 0.01194 |
| B10 | FAM | A05up2 | Unkn | 1% | 27.68 | 27.68 | 0.000 | 0.00900 |
| B11 | FAM | A05up2 | Unkn | 1% | 27.40 | 27.40 | 0.000 | 0.01087 |
| B12 | FAM | A05up2 | Unkn | 1% | 27.73 | 27.73 | 0.000 | 0.00867 |
| B01 | FAM | A05up2 | Unkn | 1% | 26.37 | 26.37 | 0.000 | 0.01000 |
| B02 | FAM | A05up2 | Unkn | 1% | 26.10 | 26.10 | 0.000 | 0.01000 |
| B03 | FAM | A05up2 | Unkn | 1% | 22.80 | 22.80 | 0.000 | 0.01000 |
| B04 | FAM | A05up2 | Unkn | 1% | 26.10 | 26.10 | 0.000 | 0.01000 |
| C01 | FAM | A05up2 | Std-3 | 0.5% | 28.71 | 28.56 | 0.103 | 0.00500 |
| C02 | FAM | A05up2 | Std-3 | 0.5% | 28.56 | 28.56 | 0.103 | 0.00500 |
| C03 | FAM | A05up2 | Std-3 | 0.5% | 28.47 | 28.56 | 0.103 | 0.00500 |
| C04 | FAM | A05up2 | Std-3 | 0.5% | 28.51 | 28.56 | 0.103 | 0.00500 |
| C05 | FAM | A05up2 | Unkn | 0.5% | 28.61 | 28.61 | 0.000 | 0.00485 |
| C06 | FAM | A05up2 | Unkn | 0.5% | 28.08 | 28.08 | 0.000 | 0.00688 |
| C07 | FAM | A05up2 | Unkn | 0.5% | 28.57 | 28.57 | 0.000 | 0.00498 |
| C08 | FAM | A05up2 | Unkn | 0.5% | 28.31 | 28.31 | 0.000 | 0.00591 |
| C09 | FAM | A05up2 | Unkn | 0.5% | 28.59 | 28.59 | 0.000 | 0.00491 |
| C10 | FAM | A05up2 | Unkn | 0.5% | 28.45 | 28.45 | 0.000 | 0.00538 |
| C11 | FAM | A05up2 | Unkn | 0.5% | 28.44 | 28.44 | 0.000 | 0.00544 |
| C12 | FAM | A05up2 | Unkn | 0.5% | 28.90 | 28.90 | 0.000 | 0.00398 |
| C01 | FAM | A05up2 | Unkn | 0.5% | 28.33 | 28.33 | 0.000 | 0.00500 |
| C02 | FAM | A05up2 | Unkn | 0.5% | 28.26 | 28.26 | 0.000 | 0.00500 |
| C03 | FAM | A05up2 | Unkn | 0.5% | 28.17 | 28.17 | 0.000 | 0.00500 |
| C04 | FAM | A05up2 | Unkn | 0.5% | 28.30 | 28.30 | 0.000 | 0.00500 |
| D01 | FAM | A05up2 | Std-4 | 0.05% | 32.05 | 31.87 | 0.468 | 0.00050 |
| D02 | FAM | A05up2 | Std-4 | 0.05% | 31.80 | 31.87 | 0.468 | 0.00050 |
| D03 | FAM | A05up2 | Std-4 | 0.05% | 32.37 | 31.87 | 0.468 | 0.00050 |
| D04 | FAM | A05up2 | Std-4 | 0.05% | 31.26 | 31.87 | 0.468 | 0.00050 |
| D05 | FAM | A05up2 | Unkn | 0.05% | 32.19 | 32.19 | 0.000 | 0.00044 |
| D06 | FAM | A05up2 | Unkn | 0.05% | 32.17 | 32.17 | 0.000 | 0.00045 |
| D07 | FAM | A05up2 | Unkn | 0.05% | 32.14 | 32.14 | 0.000 | 0.00046 |
| D08 | FAM | A05up2 | Unkn | 0.05% | 32.34 | 32.34 | 0.000 | 0.00040 |
| D09 | FAM | A05up2 | Unkn | 0.05% | 31.79 | 31.79 | 0.000 | 0.00058 |
| D10 | FAM | A05up2 | Unkn | 0.05% | 32.07 | 32.07 | 0.000 | 0.00048 |
| D11 | FAM | A05up2 | Unkn | 0.05% | 32.45 | 32.45 | 0.000 | 0.00037 |
| D12 | FAM | A05up2 | Unkn | 0.05% | 32.06 | 32.06 | 0.000 | 0.00049 |
| D01 | FAM | A05up2 | Unkn | 0.05% | 29.38 | 29.38 | 0.000 | 0.00050 |
| D02 | FAM | A05up2 | Unkn | 0.05% | 29.18 | 29.18 | 0.000 | 0.00050 |
| D03 | FAM | A05up2 | Unkn | 0.05% | 28.99 | 28.99 | 0.000 | 0.00050 |
| D04 | FAM | A05up2 | Unkn | 0.05% | 29.23 | 29.23 | 0.000 | 0.00050 |
| A05 | FAM | A05up2 | Unkn | 0.01% | 35.00 | 35.00 | 0.000 | 0.00008 |
| A06 | FAM | A05up2 | Unkn | 0.01% | 35.30 | 35.30 | 0.000 | 0.00007 |
| A07 | FAM | A05up2 | Unkn | 0.01% | 35.16 | 35.16 | 0.000 | 0.00007 |
| A08 | FAM | A05up2 | Unkn | 0.01% | 35.43 | 35.43 | 0.000 | 0.00009 |
| B05 | FAM | A05up2 | Unkn | 0.01% | 34.66 | 34.66 | 0.000 | 0.00010 |
| B06 | FAM | A05up2 | Unkn | 0.01% | 34.79 | 34.79 | 0.000 | 0.00009 |
| B07 | FAM | A05up2 | Unkn | 0.01% | 34.39 | 34.39 | 0.000 | 0.00012 |
| B08 | FAM | A05up2 | Unkn | 0.01% | 35.56 | 35.56 | 0.000 | 0.00013 |
| C05 | FAM | A05up2 | Unkn | 0.01% | 34.62 | 34.62 | 0.000 | 0.00011 |
| C06 | FAM | A05up2 | Unkn | 0.01% | 33.76 | 33.76 | 0.000 | 0.00013 |
| C07 | FAM | A05up2 | Unkn | 0.01% | 35.28 | 35.28 | 0.000 | 0.00007 |
| C08 | FAM | A05up2 | Unkn | 0.01% | 35.49 | 35.49 | 0.000 | 0.00013 |
| D05 | FAM | A05up2 | Unkn | 0.01% | 36.03 | 36.03 | 0.000 | 0.00011 |
| D06 | FAM | A05up2 | Unkn | 0.01% | 34.43 | 34.43 | 0.000 | 0.00012 |
| D07 | FAM | A05up2 | Unkn | 0.01% | 35.35 | 35.35 | 0.000 | 0.00013 |
| D08 | FAM | A05up2 | Unkn | 0.01% | 34.38 | 34.38 | 0.000 | 0.00013 |
| E01 | FAM | A05up2 | Std-5 | 0.01% | 35.56 | 35.02 | 0.417 | 0.00010 |
| E02 | FAM | A05up2 | Std-5 | 0.01% | 35.09 | 35.02 | 0.417 | 0.00010 |
| E03 | FAM | A05up2 | Std-5 | 0.01% | 34.56 | 35.02 | 0.417 | 0.00010 |
| E04 | FAM | A05up2 | Std-5 | 0.01% | 34.88 | 35.02 | 0.417 | 0.00010 |
| E05 | FAM | A05up2 | Unkn | 0.01% | 35.18 | 35.18 | 0.000 | 0.00007 |
| E06 | FAM | A05up2 | Unkn | 0.01% | 34.23 | 34.23 | 0.000 | 0.00014 |
| E07 | FAM | A05up2 | Unkn | 0.01% | 34.17 | 34.17 | 0.000 | 0.00013 |
| E08 | FAM | A05up2 | Unkn | 0.01% | 33.95 | 33.95 | 0.000 | 0.00013 |

TABLE 36

Quantification endpoint results from A05Up2

| Well | Fluor | Target | Content | Sample | End RFU | Call |
|---|---|---|---|---|---|---|
| A01 | FAM | A05up2 | Std-1 | 5% | 3936.61 | (+) Positive |
| A02 | FAM | A05up2 | Std-1 | 5% | 3991.98 | (+) Positive |
| A03 | FAM | A05up2 | Std-1 | 5% | 3642.37 | (+) Positive |
| A04 | FAM | A05up2 | Std-1 | 5% | 4126.48 | (+) Positive |
| A05 | FAM | A05up2 | Unkn | 5% | 4253.44 | (+) Positive |
| A06 | FAM | A05up2 | Unkn | 5% | 3925.93 | (+) Positive |
| A07 | FAM | A05up2 | Unkn | 5% | 4140.09 | (+) Positive |
| A08 | FAM | A05up2 | Unkn | 5% | 3957.86 | (+) Positive |
| A09 | FAM | A05up2 | Unkn | 5% | 4144.58 | (+) Positive |
| A10 | FAM | A05up2 | Unkn | 5% | 4267.10 | (+) Positive |
| A11 | FAM | A05up2 | Unkn | 5% | 4155.58 | (+) Positive |
| A12 | FAM | A05up2 | Unkn | 5% | 4006.67 | (+) Positive |
| B01 | FAM | A05up2 | Std-2 | 1% | 3758.04 | (+) Positive |
| B02 | FAM | A05up2 | Std-2 | 1% | 4028.61 | (+) Positive |
| B03 | FAM | A05up2 | Std-2 | 1% | 3919.63 | (+) Positive |
| B04 | FAM | A05up2 | Std-2 | 1% | 3692.02 | (+) Positive |
| B05 | FAM | A05up2 | Unkn | 1% | 3829.51 | (+) Positive |
| B06 | FAM | A05up2 | Unkn | 1% | 4016.99 | (+) Positive |
| B07 | FAM | A05up2 | Unkn | 1% | 3914.45 | (+) Positive |
| B08 | FAM | A05up2 | Unkn | 1% | 3945.53 | (+) Positive |
| B09 | FAM | A05up2 | Unkn | 1% | 4133.17 | (+) Positive |
| B10 | FAM | A05up2 | Unkn | 1% | 4030.71 | (+) Positive |
| B11 | FAM | A05up2 | Unkn | 1% | 4028.03 | (+) Positive |
| B12 | FAM | A05up2 | Unkn | 1% | 4021.45 | (+) Positive |
| C02 | FAM | A05up2 | Std-3 | 0.5% | 4043.07 | (+) Positive |
| C03 | FAM | A05up2 | Std-3 | 0.5% | 3924.83 | (+) Positive |
| C04 | FAM | A05up2 | Std-3 | 0.5% | 3802.13 | (+) Positive |
| C05 | FAM | A05up2 | Unkn | 0.5% | 3797.15 | (+) Positive |
| C06 | FAM | A05up2 | Unkn | 0.5% | 3987.02 | (+) Positive |
| C07 | FAM | A05up2 | Unkn | 0.5% | 3929.07 | (+) Positive |
| C08 | FAM | A05up2 | Unkn | 0.5% | 4020.64 | (+) Positive |
| C09 | FAM | A05up2 | Unkn | 0.5% | 3747.90 | (+) Positive |
| C10 | FAM | A05up2 | Unkn | 0.5% | 4017.08 | (+) Positive |
| C11 | FAM | A05up2 | Unkn | 0.5% | 4095.53 | (+) Positive |
| C12 | FAM | A05up2 | Unkn | 0.5% | 3826.06 | (+) Positive |
| D01 | FAM | A05up2 | Std-4 | 0.05% | 2941.46 | (+) Positive |
| D02 | FAM | A05up2 | Std-4 | 0.05% | 3155.37 | (+) Positive |
| D03 | FAM | A05up2 | Std-4 | 0.05% | 2872.07 | (+) Positive |
| D05 | FAM | A05up2 | Unkn | 0.05% | 3019.58 | (+) Positive |
| D06 | FAM | A05up2 | Unkn | 0.05% | 3029.01 | (+) Positive |
| D07 | FAM | A05up2 | Unkn | 0.05% | 3086.62 | (+) Positive |
| D08 | FAM | A05up2 | Unkn | 0.05% | 2841.71 | (+) Positive |
| D09 | FAM | A05up2 | Unkn | 0.05% | 3229.85 | (+) Positive |
| D10 | FAM | A05up2 | Unkn | 0.05% | 3170.62 | (+) Positive |
| D11 | FAM | A05up2 | Unkn | 0.05% | 3007.79 | (+) Positive |
| D12 | FAM | A05up2 | Unkn | 0.05% | 3285.98 | (+) Positive |

TABLE 36-continued

Quantification endpoint results from A05Up2

| Well | Fluor | Target | Content | Sample | End RFU | Call |
|---|---|---|---|---|---|---|
| E01 | FAM | A05up2 | Std-5 | 0.01% | 2223.89 | (+) Positive |
| E02 | FAM | A05up2 | Std-5 | 0.01% | 1947.03 | (+) Positive |
| E03 | FAM | A05up2 | Std-5 | 0.01% | 2185.70 | (+) Positive |
| E04 | FAM | A05up2 | Std-5 | 0.01% | 1979.83 | (+) Positive |
| E05 | FAM | A05up2 | Neg Ctrl | AV Jade | −3.13 | |
| E06 | FAM | A05up2 | Neg Ctrl | AV Jade | −1.95 | |
| E07 | FAM | A05up2 | Neg Ctrl | AV Jade | −3.27 | |
| E08 | FAM | A05up2 | Neg Ctrl | AV Jade | −2.97 | |
| F01 | FAM | A05up2 | Neg Ctrl | NTC | 15.77 | |
| F02 | FAM | A05up2 | Neg Ctrl | NTC | 57.86 | |
| F03 | FAM | A05up2 | Neg Ctrl | NTC | 63.71 | |
| F04 | FAM | A05up2 | Neg Ctrl | NTC | 232.51 | |
| F05 | FAM | A05up2 | Neg Ctrl | AV Jade | −1.25 | |
| F06 | FAM | A05up2 | Neg Ctrl | AV Jade | −4.07 | |
| F07 | FAM | A05up2 | Neg Ctrl | AV Jade | −1.11 | |
| F08 | FAM | A05up2 | Neg Ctrl | AV Jade | −2.17 | |

Std = Standard; Unkn = Unknown; Neg Ctrl = Negative Control; NTC = No Template Control Table 37 and Table 38 reported the tested results from Ae2Dn2 and A 5Up2 with twenty-seven reference materials from AOCS, respectively. The results demonstrated two assays can detect the DHA positive results only from the canola materials that contains canola NS-1B50027-4 DHA event. It generated negative results from all twenty-seven AOCS materials (one regular non-GM canola, seven canola events, seven maize events, seven soybean events, one regular non-GM cotton, and four GM cotton events). The data demonstrated the specificity of the two assays for the event NS-1B50027-4.

TABLE 37

Results from A02dn2 assay tested with 27 Reference materials from AOCS

| Well | Fluor | Target | Content | Sample | End RFU | Call |
|---|---|---|---|---|---|---|
| A01 | FAM | A02Dn2 | Std-1 | 5% | 5030.21 | (+) Positive |
| A02 | FAM | A02Dn2 | Std-1 | 5% | 5213.67 | (+) Positive |
| A03 | FAM | A02Dn2 | Std-1 | 5% | 5342.89 | (+) Positive |
| A04 | FAM | A02Dn2 | Std-1 | 5% | 5213.29 | (+) Positive |
| A09 | FAM | A02Dn2 | Unkn | AOCS-S1 | 626.60 | |
| A10 | FAM | A02Dn2 | Unkn | AOCS-S2 | 792.80 | |
| A11 | FAM | A02Dn2 | Unkn | AOCS-S3 | 222.95 | |
| A12 | FAM | A02Dn2 | Unkn | AOCS-S4 | 663.18 | |
| B01 | FAM | A02Dn2 | Std-2 | 1% | 5335.65 | (+) Positive |
| B02 | FAM | A02Dn2 | Std-2 | 1% | 5355.73 | (+) Positive |
| B03 | FAM | A02Dn2 | Std-2 | 1% | 5171.06 | (+) Positive |
| B04 | FAM | A02Dn2 | Std-2 | 1% | 5406.99 | (+) Positive |
| B09 | FAM | A02Dn2 | Unkn | AOCS-S5 | 1296.79 | |
| B10 | FAM | A02Dn2 | Unkn | AOCS-S6 | 578.10 | |
| B11 | FAM | A02Dn2 | Unkn | AOCS-S7 | −0.83 | |
| B12 | FAM | A02Dn2 | Unkn | AOCS-S8 | 796.00 | |
| C01 | FAM | A02Dn2 | Std-3 | 0.5% | 5376.35 | (+) Positive |
| C02 | FAM | A02Dn2 | Std-3 | 0.5% | 5419.13 | (+) Positive |
| C03 | FAM | A02Dn2 | Std-3 | 0.5% | 5437.75 | (+) Positive |
| C04 | FAM | A02Dn2 | Std-3 | 0.5% | 5135.10 | (+) Positive |
| C09 | FAM | A02Dn2 | Unkn | AOCS-S9 | 329.25 | |
| C10 | FAM | A02Dn2 | Unkn | AOCS-S10 | 1096.04 | |
| C11 | FAM | A02Dn2 | Unkn | AOCS-S11 | 246.10 | |
| C12 | FAM | A02Dn2 | Unkn | AOCS-S12 | 707.63 | |
| D01 | FAM | A02Dn2 | Std-4 | 0.05% | 4167.95 | (+) Positive |
| D02 | FAM | A02Dn2 | Std-4 | 0.05% | 4356.11 | (+) Positive |
| D03 | FAM | A02Dn2 | Std-4 | 0.05% | 4153.12 | (+) Positive |
| D04 | FAM | A02Dn2 | Std-4 | 0.05% | 4286.66 | (+) Positive |
| D09 | FAM | A02Dn2 | Unkn | AOCS-S13 | 1273.47 | |
| D10 | FAM | A02Dn2 | Unkn | AOCS-S14 | 853.09 | |
| D11 | FAM | A02Dn2 | Unkn | AOCS-S15 | 0.49 | |
| D12 | FAM | A02Dn2 | Unkn | AOCS-S16 | 293.96 | |
| E01 | FAM | A02Dn2 | Std-5 | 0.01% | 2549.72 | (+) Positive |
| E02 | FAM | A02Dn2 | Std-5 | 0.01% | 2766.77 | (+) Positive |
| E03 | FAM | A02Dn2 | Std-5 | 0.01% | 2524.80 | (+) Positive |
| E04 | FAM | A02Dn2 | Std-5 | 0.01% | 2834.62 | (+) Positive |
| E09 | FAM | A02Dn2 | Unkn | AOCS-S17 | 1224.08 | |
| E10 | FAM | A02Dn2 | Unkn | AOCS-S18 | 1185.69 | |
| E11 | FAM | A02Dn2 | Unkn | AOCS-S19 | 828.69 | |
| E12 | FAM | A02Dn2 | Unkn | AOCS-S20 | 885.38 | |
| F01 | FAM | A02Dn2 | Neg Ctrl | AV Jade | 289.44 | |
| F02 | FAM | A02Dn2 | Neg Ctrl | AV Jade | −2.50 | |
| F03 | FAM | A02Dn2 | Neg Ctrl | AV Jade | 325.30 | |
| F04 | FAM | A02Dn2 | Neg Ctrl | AV Jade | −2.65 | |
| F09 | FAM | A02Dn2 | Unkn | AOCS-S21 | −0.68 | |
| F10 | FAM | A02Dn2 | Unkn | AOCS-S22 | 798.27 | |
| F11 | FAM | A02Dn2 | Unkn | AOCS-S23 | 436.95 | |
| F12 | FAM | A02Dn2 | Unkn | AOCS-S24 | 437.00 | |
| G01 | FAM | A02Dn2 | NTC | NTC | −3.49 | |
| G02 | FAM | A02Dn2 | NTC | NTC | −4.10 | |
| G03 | FAM | A02Dn2 | NTC | NTC | −2.60 | |
| G04 | FAM | A02Dn2 | NTC | NTC | −2.42 | |
| G09 | FAM | A02Dn2 | Unkn | AOCS-S25 | 340.56 | |
| G10 | FAM | A02Dn2 | Unkn | AOCS-S26 | 1101.64 | |
| G11 | FAM | A02Dn2 | Unkn | AOCS-S27 | 27.80 | |
| G12 | FAM | A02Dn2 | Unkn | AV Jade | −4.26 | |
| H09 | FAM | A02Dn2 | Unkn | NTC | −3.69 | |
| H10 | FAM | A02Dn2 | Unkn | NTC | −2.11 | |
| H11 | FAM | A02Dn2 | Unkn | NTC | −4.07 | |
| H12 | FAM | A02Dn2 | Unkn | NTC | −2.67 | |

Std = Standard; Unkn = Unknown; Neg Ctrl = Negative Control; NTC = No Template Control

TABLE 38

Results from A05up2 assay tested with 27 Reference materials from AOCS

| Well | Fluor | Assay | Content | Sample | End RFU | Call |
|---|---|---|---|---|---|---|
| A01 | FAM | A05Up2 | Std | 5% | 4043.64 | (+) Positive |
| A02 | FAM | A05Up2 | Std | 5% | 4269.35 | (+) Positive |
| A03 | FAM | A05Up2 | Std | 5% | 4339.56 | (+) Positive |
| A04 | FAM | A05Up2 | Std | 5% | 4433.77 | (+) Positive |
| A09 | FAM | A05Up2 | Unkn | AOCS-S1 | 4.68 | |
| A10 | FAM | A05Up2 | Unkn | AOCS-S2 | 20.88 | |
| A11 | FAM | A05Up2 | Unkn | AOCS-S3 | 20.47 | |
| A12 | FAM | A05Up2 | Unkn | AOCS-S4 | −24.55 | |
| B01 | FAM | A05Up2 | Std | 1% | 4361.68 | (+) Positive |
| B02 | FAM | A05Up2 | Std | 1% | 4410.84 | (+) Positive |
| B03 | FAM | A05Up2 | Std | 1% | 4611.71 | (+) Positive |
| B04 | FAM | A05Up2 | Std | 1% | 4467.86 | (+) Positive |
| B09 | FAM | A05Up2 | Unkn | AOCS-S5 | 28.81 | |
| B10 | FAM | A05Up2 | Unkn | AOCS-S6 | 106.96 | |
| B11 | FAM | A05Up2 | Unkn | AOCS-S7 | −4.41 | |
| B12 | FAM | A05Up2 | Unkn | AOCS-S8 | −1.81 | |
| C01 | FAM | A05Up2 | Std | 0.5% | 4246.57 | (+) Positive |
| C02 | FAM | A05Up2 | Std | 0.5% | 4250.34 | (+) Positive |
| C03 | FAM | A05Up2 | Std | 0.5% | 4387.30 | (+) Positive |
| C04 | FAM | A05Up2 | Std | 0.5% | 4198.63 | (+) Positive |
| C09 | FAM | A05Up2 | Unkn | AOCS-S9 | −1.60 | |
| C10 | FAM | A05Up2 | Unkn | AOCS-S10 | 46.36 | |
| C11 | FAM | A05Up2 | Unkn | AOCS-S11 | 0.15 | |
| C12 | FAM | A05Up2 | Unkn | AOCS-S12 | −3.12 | |
| D01 | FAM | A05Up2 | Std | 0.05% | 4037.75 | (+) Positive |
| D02 | FAM | A05Up2 | Std | 0.05% | 4190.77 | (+) Positive |
| D03 | FAM | A05Up2 | Std | 0.05% | 4252.24 | (+) Positive |
| D04 | FAM | A05Up2 | Std | 0.05% | 4066.26 | (+) Positive |
| D09 | FAM | A05Up2 | Unkn | AOCS-S13 | 1.55 | |
| D10 | FAM | A05Up2 | Unkn | AOCS-S14 | 5.55 | |
| D11 | FAM | A05Up2 | Unkn | AOCS-S15 | 3.31 | |
| D12 | FAM | A05Up2 | Unkn | AOCS-S16 | −2.72 | |
| E01 | FAM | A05Up2 | Std | 0.01% | 3297.99 | (+) Positive |
| E02 | FAM | A05Up2 | Std | 0.01% | 3717.55 | (+) Positive |
| E03 | FAM | A05Up2 | Std | 0.01% | 3438.54 | (+) Positive |
| E04 | FAM | A05Up2 | Std | 0.01% | 3296.74 | (+) Positive |
| E09 | FAM | A05Up2 | Unkn | AOCS-S17 | 31.35 | |

TABLE 38-continued

Results from A05up2 assay tested with 27 Reference materials from AOCS

| Well | Fluor | Assay | Content | Sample | End RFU | Call |
|---|---|---|---|---|---|---|
| E10 | FAM | A05Up2 | Unkn | AOCS-S18 | 444.94 | |
| E11 | FAM | A05Up2 | Unkn | AOCS-S19 | 1.80 | |
| E12 | FAM | A05Up2 | Unkn | AOCS-S20 | −1.47 | |
| F09 | FAM | A05Up2 | Unkn | AOCS-S21 | 28.18 | |
| F10 | FAM | A05Up2 | Unkn | AOCS-S22 | 56.39 | |
| F11 | FAM | A05Up2 | Unkn | AOCS-S23 | 2.12 | |
| F12 | FAM | A05Up2 | Unkn | AOCS-S24 | −2.83 | |
| G01 | FAM | A05Up2 | Neg Ctrl | AV Jade | −4.99 | |
| G02 | FAM | A05Up2 | Neg Ctrl | AV Jade | −2.17 | |
| G03 | FAM | A05Up2 | Neg Ctrl | AV Jade | −4.91 | |
| G04 | FAM | A05Up2 | Neg Ctrl | AV Jade | −3.89 | |
| G09 | FAM | A05Up2 | Unkn | AOCS-S25 | −2.89 | |
| G10 | FAM | A05Up2 | Unkn | AOCS-S26 | −2.39 | |
| G11 | FAM | A05Up2 | Unkn | AOCS-S27 | −0.19 | |
| G12 | FAM | A05Up2 | Unkn | AV Jade | 0.19 | |
| H01 | FAM | A05Up2 | NTC | NTC | −2.46 | |
| H02 | FAM | A05Up2 | NTC | NTC | −0.41 | |
| H03 | FAM | A05Up2 | NTC | NTC | 11.47 | |
| H04 | FAM | A05Up2 | NTC | NTC | 1.89 | |
| H09 | FAM | A05Up2 | Unkn | NTC | 13.89 | |
| H10 | FAM | A05Up2 | Unkn | NTC | 96.79 | |
| H11 | FAM | A05Up2 | Unkn | NTC | 4.05 | |
| H12 | FAM | A05Up2 | Unkn | NTC | −1.59 | |

Std = Standard; Unkn = Unknown; Neg Ctrl = Negative Control; NTC = No Template Control Assays A02dn2 and A05up2, targeting the two inserts of DHA canola NS-B50027-4 event, respectively, have been tested with different DHA GM spike levels and validated with commercially available GMO events. The lowest level (LOD) can be detected is 0.01% GM DNA spike which is less than ten copy DHA DNA in the reaction. The lowest level (LOQ) quantified was 0.05% DNA spike, which was less than fifty copy DHA canola NS-B50027-4 DNA in the reaction. All other technical parameters such as RSD, bias, R2, slope from these assays were established within the EU acceptance criteria in accordance to the EU-requirements of the relevant EU legislation.

Example 6. Gel Electrophoresis-Based A05-216 Qualitative Event-Specific Assay for Detection of the Transgenic Event in DHA Canola NS-B50027-4

DNA were extracted from seeds using CTAB DNA extraction method briefly described below:

Step 1: Grind 3000 seeds per sample completely and transfer powder to 50 mL Falcon tubes. Clean grinder thoroughly between samples to prevent cross contamination Step 2: Add 30 mL of 1× CTAB Extraction Buffer (1% CTAB, 50 mM Tris-HCl pH 8.0, and 10 mM EDTA pH 8.0) and mix thoroughly by shaking and inverting the tube several times.

Step 3: Incubate the samples in 55-60° C. (57.5° C. optimal) water bath for 1 hr. Mix the samples every 10 min by lightly inverting the tubes. After the incubation, let the samples cool down to room temperature.

Step 4: Centrifuge the samples for 2 min at 3000 g. Carefully remove as much as possible the top layer, which is oil, using pipet. The light brown middle layer contains DNA. Centrifuge the samples again for 10 min at 3000 g.

Step 5: For each sample, transfer 900 uL of the middle layer to a 2 mL centrifuge tube, add 900 μL chloroform under a fume hood. Mix the samples vigorously for 5 min. Centrifuge the samples for 5 min at 13000 g.

Step 6: Transfer 750 μL of the supernatant to a new 2.0 mL centrifuge tube, add 750 μL 1X CTAB Buffer and mix by inverting the tubes 10-15 times. Then let the samples rest at room temperature on bench for 5 min. Proceed to centrifuge the samples at 13000 g for 7 min. Discard the supernatant.

Step 7: Add 250 μL 1M NaCl solution containing RNase A (final concentration 20 pg/mL) to each sample and mix by inverting 5-10 times. Incubate samples in 50° C. for 1 hr. Gently invert the tubes every 10 min during incubation.

Step 8: Let the samples cool down to room temperature. Then, add 500 ul −20° C. 100% ethanol. Invert the tubes gently for about 5 min to precipitate DNA. Centrifuge the samples at 13000 g for 5 min and discard the supernatant. Wash the DNA pellet with 500 μL 70% Ethanol at room temperature for at least 30 min.

Step 9: Centrifuge the tubes at 13000 g for 5 min and discard the supernatant. Dry the sample tubes under the fume hood for about 30-60 min. Do not over dry DNA pellet. Add 100 μL of $H_2O$ to each sample and suspend the DNA by pipetting. Add 1 uL DNase-free RNase A (10 mg/mL) to the DNA solution and incubate at 50° C. water bath or oven for 60 min. Let the samples sit at room temperature for about 30 min before checking the DNA quantity, e.g., with Qubit4 fluorometer from Invitrogen.

Store the DNA samples at 4° C. for temporary storage up to a week or at −20° C. for long term storage.

For an event-specific PCR method, samples were prepared with different NS-B50027-4 DNA level spikes. Sample 20 ng/μl DNA solutions from DHA canola NS-B50027-4 DNA and negative control AV Jade were prepared before making up the following spike samples, as provided in Table 39. Six DHA canola NS-B50027-4 spike levels were made as described below, the genome copies number of reference gene HMG and DHA canola is listed in Table 40.

TABLE 39

Concentrations of spike samples

| | | |
|---|---|---|
| 1. | 50% spike sample: | Mix equal volume of the DHA canola DNA solution (20 ng/μL) and the negative control AV Jade DNA solution (20 ng/μL). |
| 2. | 10% spike sample: | Dilute 5 times of the 50% spike sample with DNA solutions from the AV Jade (20 ng/μL) to make up the 10% spike sample. |
| 3. | 1% spike sample: | Dilute 10 times of the 10% spike sample with DNA from AV Jade (20 ng/μL) to make up the 1% spike sample. |
| 4. | 0.1% spike sample: | Dilute 10 times of the 1% spike sample with DNA from AV Jade (20 ng/μL) to make up the 0.1% spike sample. |
| 5. | 0.05% spike sample: | Dilute 2 times of the 0.1% spike sample with DNA from AV Jade (20 ng/μL) to make up the 0.05% spike sample. |
| 6. | 0.025% spike sample: | Dilute 2 times of the 0.05% spike sample with DNA from AV Jade (20 ng/μL) to make up the 0.025% spike sample. |

TABLE 40

Six spike level samples with corresponding reference gene genome copy number, and the copy number for NS-B50027-4

| DHA canola dilution series | 50% | 10% | 1% | 0.1% | 0.05% | 0.025% |
|---|---|---|---|---|---|---|
| Total amount of DNA (ng) | 100 | 100 | 100 | 100 | 100 | 100 |

TABLE 40-continued

Six spike level samples with corresponding reference gene genome copy number, and the copy number for NS-B50027-4

| Target taxon HMG copies | 86957 | 86957 | 86957 | 86957 | 86957 | 86957 |
|---|---|---|---|---|---|---|
| GM % (NS-B50027-4) | 50 | 10 | 1 | 0.1 | 0.05 | 0.025 |
| NS-B50027-4 oilseed rape GM copies | 43478 | 8695 | 869 | 87 | 43.4 | 21.7 |

For the PCR assay, all reaction (25 μL/reaction) components (Cat Log #:M0480L) were assembled on ice as illustrated in Table 41.

TABLE 41

PCR reaction assembly

| Components | Volume (μL) |
|---|---|
| 5X OneTaq Standard Reaction Buffer (NEB) | 5.0 |
| 10 mM of each dNTPs | 0.5 |
| 2.5 μM event specific assay mixture (forward and reverse primers mixture) or Internal Reference Gene (HMG) forward and reverse primers mixture* | 2.0 |
| OneTaq DNA Polymerase (5 units/μL) (NEB) | 0.2 |
| Template DNA (20 ng/μL)** | 5.0 |
| Nuclease-free water | 12.3 |
| Total reaction | 25.0 |

*This applies to three separate experiments with:
(1) Forward and reverse primers mixture for detecting the A02 insert;
(2) Forward and reverse primers mixture for detecting the A05 insert; and
(3) Forward and reverse primers mixture for detecting the endogenous HMG gene.
**Ne positive control, negative control, and non-template control in each of the three experiments.

PCR Cycling Profile:

PCR was used for amplification with the profile parameters shown in Table 42:

TABLE 42

PCR cycling profile

| | Stage | Temperature | Time | Cycles |
|---|---|---|---|---|
| 1 | Initial denaturation | 94° C. | 60 sec | 1 |
| 2 | Denaturation | 94° C. | 30 sec | |
| 3 | Annealing | 58° C. | 30 sec | 35 |
| 4 | Elongation | 72° C. | 30 sec | |
| 5 | Final extension | 72° C. | 5 min | 1 |
| 6 | | 10° C. | Forever | |

Reference gene and DNA ladders were prepared as follows. Internal reference gene: Canola HMG is used as the internal reference gene for this qualitative detection method. Primer sequences are provided in Table 43, below. The amplicon size for HMG is 206 bp.

GeneRuler low range DNA ladder: Thermo Scientific™ GeneRuler™ Low Range DNA Ladder, ready-to-use, contains a mix of ten chromatography-purified individual DNA fragments (in base pairs): 700, 500, 400, 300, 200, 150, 100, 75, 50, and 25 (FIG. 1).

PCR products are resolved through agarose gel electrophoresis and analyzed with the Life Technology Image System. For each PCR reaction, 10 μL PCR products is mixed with 3 μL H$_2$O and 1 μL loading dye (6x; Thermo Fisher Scientific Cat. Log #R1161) and run on a 2% agarose gel (gel size 14 cm long and 12 cm wide) at 100 Volts for 60 minutes. DNA ladder (6 μl per lane) is run on proper number of lanes to enable PCR amplicon sizes to be identified. Gel image is captured with the Life Technology Image system.

Chemicals and equipment that are needed for DNA extraction: CTAB, NaCl, Tris-HCl, EDTA, DNase-free RNase, Ethanol, Grinder, Centrifuge, Tubes, etc.

For primers designed across the junctions of insertions in DHA canola: The qualitative event-specific assay (A05-216) was designed to detect the junction between T-DNA insert and genomic DNA on Chromosome A05. The qualitative event-specific assay (A02-258) was designed to detect the junction between T-DNA insert and genomic DNA on Chromosome A02, see WO/2020/055763. The primer sequences, locations, and product sizes are shown in Table 43, FIG. 23, Primers designed across the junctions of insertions in DHA canola and FIG. 8. The Brassica HMG gene was used as the reference gene for the internal control recommended by Chinese National Standard (MARA 2031-9-2013). Primer sequences and the expected amplicon sizes are listed in the following table. The primer pair A02-258F and A02-258R is used to detect the insert or junction on chromosome A02, and the amplicon size is 258 bp. The primer pair A05-216F and A05-216R is used to detect the insert or junction on chromosome A05, and the amplicon size is 216 bp. The primer pair Hmg206F and Hmg206R is used to detect the endogenous HMG gene (internal reference gene HMG as control), and the amplicon size is 206 bp.

TABLE 43

Primer sequences for assay A05-216 and the reference gene HMG

| Primer Name | Primer Sequence | Amplicon Size |
|---|---|---|
| A05-216F | AGATTGTCGTTTCCCGCCTTC (SEQ ID NO: 28) | 216 bp |
| A05-216R | GCTGCCTTGCCGCTTCTAA (SEQ ID NO: 29) | |
| A02-258F | CATTGAGCAGTGAACACCAAG (SEQ ID NO: 20) | 258 bp |
| A02-258R | CAGTTTAAACTATCAGTGTTTGAACAC (SEQ ID NO: 21) | |
| Hmg206F | TCCTTCCGTTTCCTCGCC (SEQ ID NO: 22) | 206 bp |
| Hmg206R | TTCCACGCCCTCTCCGCT (SEQ ID NO: 23) | |

A hundred nanogram (ng) genomic DNA template of the following samples were subject to event-specific qualitative PCR (Assay A05-216 for junction in chromosome A05 and Assay HMG for Reference Gene):

Event NS-50027-4 as positive control for event-specific Assay (A05-216);

Canola AV Jade as negative control for event-specific Assay (A05-216) and positive control for Reference Gene Assay HMG;

Seven Non-GM conventional canola varieties selected from Nuseed germplasm pool: NX0026, NX0331, NX0953, NX0980, NX1012, NX1302, NX1306;

Two Certified Non-Modified Reference Materials (Leaf DNA) purchased from American Oil Chemists' Society (AOCS): Canola 0306-B4, Cotton 0306-A4;

Twenty-Five Certified GM Reference Materials (Leaf DNA or seeds powder) purchased from AOCS:

Seven Canola Events: Topas19/2, T45, Rf2, Rf1, Ms8, Ms1, Rf3;

Seven Soybean Events: MON89788, MON87769, MON87708, MON87705, MON87701, FG72, A5547-127;

Seven Maize Events: GA21, MON89034, MIR604, MON88017, MON87427, MON87460, T25; and Four Cotton Events: MON15985-7, MON531, MON1445, GHB614.

The results from the qualitative event-specific assay with six different DHA canola NS-B50027-4 spike levels.

Figure 25:
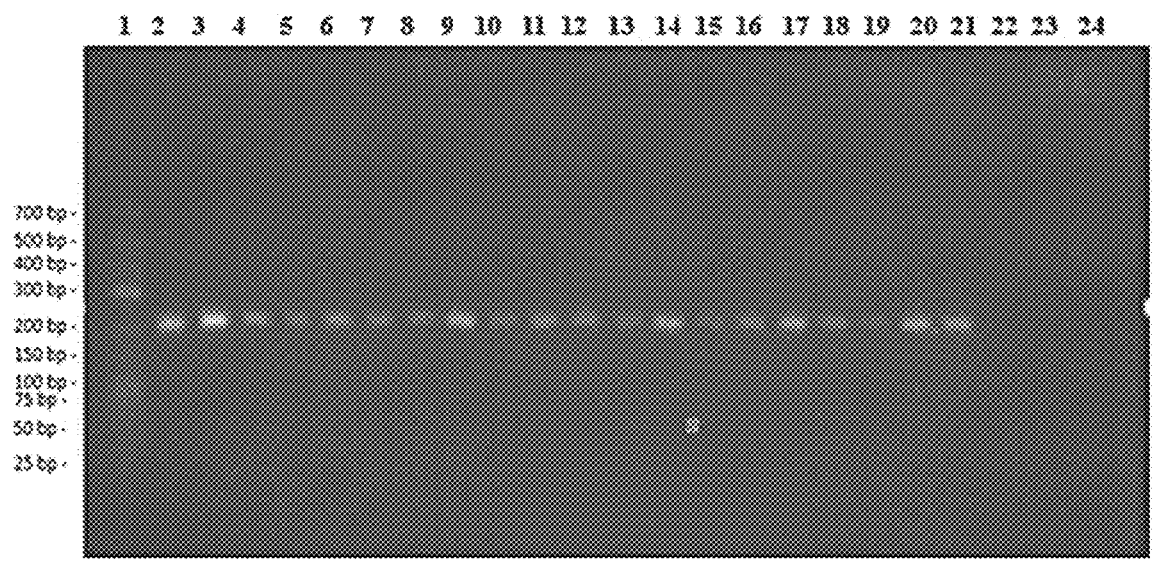
FIG. 25 is a gel image from a qualitative event-specific assay (A05-216) for a 216-bp amplicon of sixteen replicates of event positive 0.05% spike samples.

The qualitative event-specific assay (A05-216) was tested with AV Jade, NTC, six different DHA canola NS-B50027-4 spike levels, and 8 conventional Nuseed canola lines (FIG. 24). The results from 16 replicates showed the assay can consistently detect the expected amplicons at least 0.05% spike level (FIG. 25). Gel lanes for FIG. 24 and FIG. 25 from the assays are provided in Table 44 and Table 45.

TABLE 44

Gel lanes showing the amplicons from assay A05-216 with different omega3 DNA spike and 8 canola lines, as depicted FIG. 24

| Lane | Assay | Sample | Lane | Assay | Sample |
|---|---|---|---|---|---|
| 1 | DNA ladder | DNA ladder | 12 | A05-216 | 0.025% spike |
| 2 | A05-216 | AV Jade (neg control) | 13 | A05-216 | NX0026 |
| 3 | A05-216 | NTC | 14 | A05-216 | NX0331 |
| 4 | A05-216 | 50% DHA spike | 15 | A05-216 | NX0953 |
| 5 | A05-216 | 50% DHA spike | 16 | A05-216 | NX0980 |
| 6 | A05-216 | 10% spike | 17 | A05-216 | NX1012 |
| 7 | A05-216 | 1% spike | 18 | A05-216 | NX1302 |
| 8 | A05-216 | 0.1% spike | 19 | A05-216 | NX1306 |
| 9 | A05-216 | 0.05% spike | 20 | A05-216 | Canola 0306-B4 |
| 10 | A05-216 | 0.05% spike | 21 | A05-216 | 100% DHA |
| 11 | A05-216 | 0.05% spike | 22 | DNA ladder | DNA ladder |

TABLE 45

Gel lanes showing the amplicons from assay A05-216 with 16 replicates of event positive 0.05% spike sample, as depicted in FIG. 25

| Lane | Assay | Sample | Lane | Assay | Sample |
|---|---|---|---|---|---|
| 1 | DNA ladder | DNA ladder | 13 | A05-216 | Event positive 0.05% |
| 2 | A05-216 | Event Positive 0.1% | 14 | A05-216 | Event positive 0.05% |
| 3 | A05-216 | Event Positive 0.1% | 15 | A05-216 | Event positive 0.05% |
| 4 | A05-216 | Event positive 0.05% | 16 | A05-216 | Event positive 0.05% |
| 5 | A05-216 | Event positive 0.05% | 17 | A05-216 | Event positive 0.05% |
| 6 | A05-216 | Event positive 0.05% | 18 | A05-216 | Event positive 0.05% |
| 7 | A05-216 | Event positive 0.05% | 19 | A05-216 | Event positive 0.05% |
| 8 | A05-216 | Event positive 0.05% | 20 | A05-216 | Event positive 0.1% |
| 9 | A05-216 | Event positive 0.05% | 21 | A05-216 | Event positive 0.1% |
| 10 | A05-216 | Event positive 0.05% | 22 | A05-216 | Event positive 0.025% |
| 11 | A05-216 | Event positive 0.05% | 23 | A05-216 | AV Jade (DHA negative) |
| 12 | A05-216 | Event positive 0.05% | 24 | A05-216 | NTC |

Specificity of the qualitative event-specific Assay and Reference Gene Assay HMG in various events among same species (Canola) was tested as follows. The qualitative event-specific Assay (A05-216) and reference gene assay HMG206 were tested with six different commercial canola GMO events ordered from AOCS. The results showed assay A05-216 (FIG. 26) did not have any amplicons from six commercial canola events. The reference gene assay HMG206 amplified the expected amplicons from the six commercial canola events as expected. The results demonstrated the assay A05-216 developed is specific for NS-50027-4 event in canola.

TABLE 46

Figure 26:
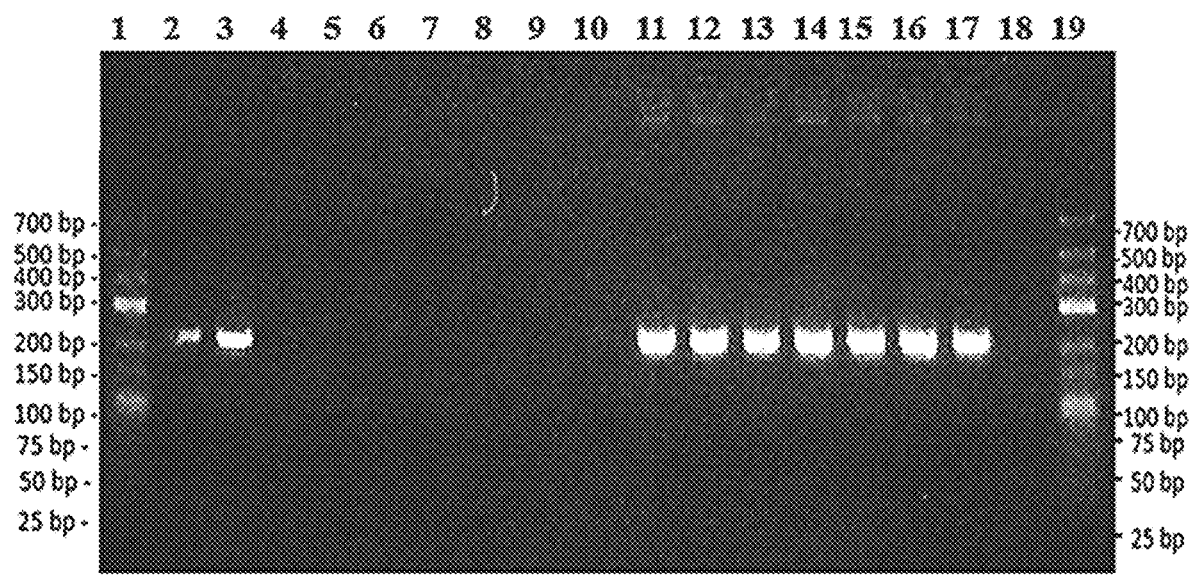
FIG. 26 is a gel image showing the absence of the A05-216 amplicon in six different commercial canola GMO events and the presence of the HMG206-amplicon (206-bp).

Gel lanes showing the amplicons from assay A05-216 with 6 different commercial canola GMO events ordered from AOCS, as depicted in FIG. 26.

| Lane | Assay | Sample | Lane | Assay | Sample |
|---|---|---|---|---|---|
| 1 | DNA ladder | DNA ladder | 11 | HMG206 | Canola event T45 |
| 2 | A05-216 | Event Positive control | 12 | HMG206 | Canola event Rf1 |
| 3 | A05-216 | 100% DHA Positive | 13 | HMG206 | Canola event Rf2 |
| 4 | A05-216 | AV Jade (DHA negative) | 14 | HMG206 | Canola event Rf3 |
| 5 | A05-216 | Canola event T45 | 15 | HMG206 | Canola event Ms8 |
| 6 | A05-216 | Canola event Rf1 | 16 | HMG206 | Canola event Ms1 |
| 7 | A05-216 | Canola event Rf2 | 17 | HMG206 | AV Jade HMG positive |
| 8 | A05-216 | Canola event Rf3 | 18 | HMG206 | NTC |
| 9 | A05-216 | Canola event Ms8 | 19 | DNA ladder | DNA ladder |
| 10 | A05-216 | Canola event Ms1 | | | |

Specificity of the qualitative event-specific assay was analyzed in various events across *Brassica napus* and other different species: The qualitative event-specific Assay A05-216 were tested with twenty-seven CRM materials ordered from AOCS including twenty-finve different commercial GMO events. The results showed assay A05-216 did not have any amplicons from all these materials, including in eight canola CRM (seven GMO events and one non-GMO canola (FIG. 27A), seven soybean events, seven maize events, four cotton events and one non-GMO cotton (FIG. 27B). The DHA canola positive controls amplified the expected amplicons in the same experiment. The results demonstrated the assay A05-216 provided herein is event specific for only canola NS-500274 event.

TABLE 47

Figure 27A:
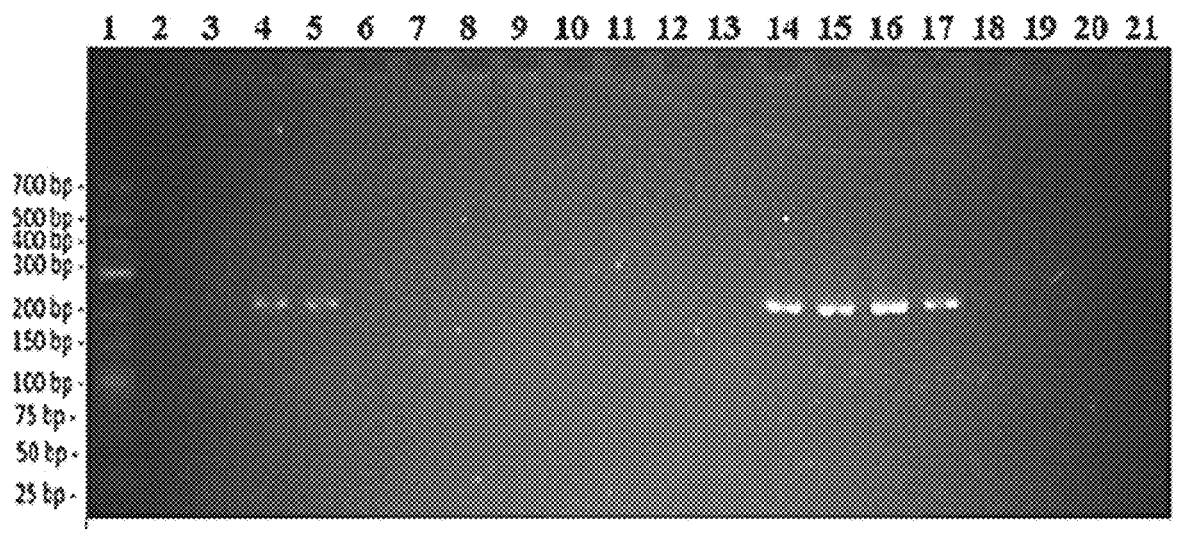
FIG. 27A is a gel image from the qualitative event-specific assay A05-216 with eight canola Certified Reference Materials (CRM; seven genetically modified (GM) and one regular canola materials) from AOCS. The 216-bp amplicon was absent in all of the eight canola CRM.
Figure 27B:
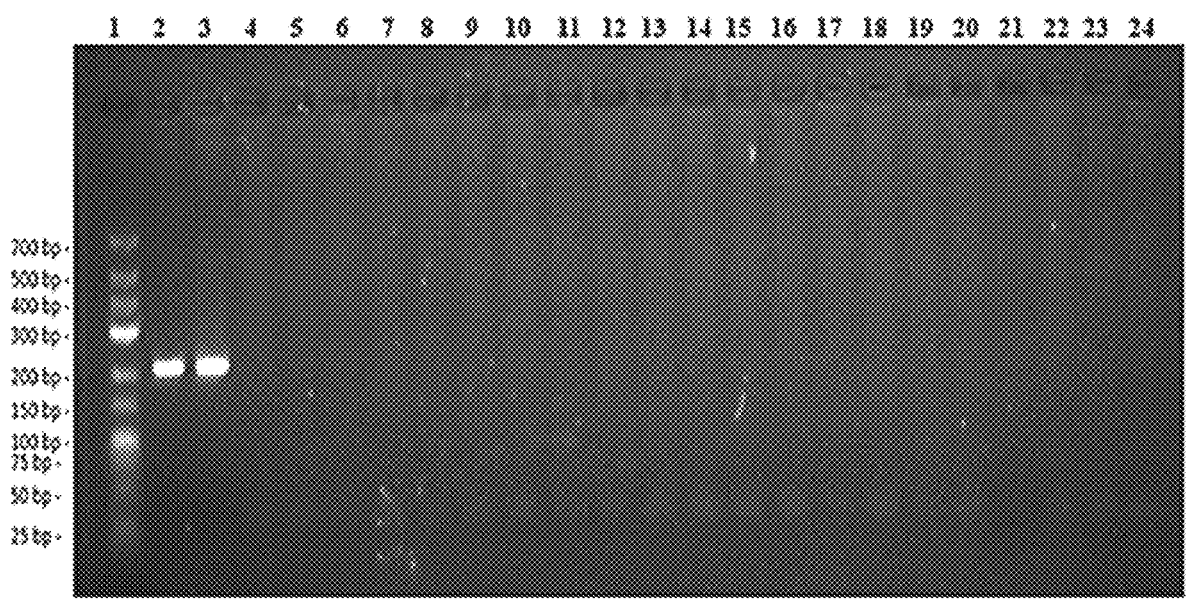
FIG. 27B is a gel image from the qualitative event-specific assay A05-216 with seven soybean, seven maize and five cotton Certified Reference Materials (CRM; four genetically modified (GM) and one regular cotton materials) from AOCS. The 216-bp amplicon was absent in all of the CRM tested.

Gel lanes showing the amplicons from assay A05-216 with eight canola Certified Materials (CRM; 7 GM and 1 regular canola materials), as shown in FIG. 27A

| Lane | Assay | Sample | Lane | Assay | Sample |
|---|---|---|---|---|---|
| 1 | DNA ladder | DNA ladder | 12 | A05-216 | Canola event Ms1 |
| 2 | A05-216 | 0.025% Event Positive | 13 | A05-216 | Canola event Rf3 |
| 3 | A05-216 | 0.025% Event Positive | 14 | A05-216 | Event Positive control |
| 4 | A05-216 | 0.05% Event Positive | 15 | A05-216 | Event Positive control |
| 5 | A05-216 | 0.05% Event Positive | 16 | A05-216 | 50% Event Positive |
| 6 | A05-216 | Non-Modified canola 0306-B4 | 17 | A05-216 | 10% Event Positive |
| 7 | A05-216 | Canola event Topas19/2 | 18 | A05-216 | AV Jade (DHA negative) |
| 8 | A05-216 | Canola event T45 | 19 | A05-216 | AV Jade (DHA negative) |
| 9 | A05-216 | Canola event Rf2 | 20 | A05-216 | NTC |
| 10 | A05-216 | Canola event Rf1 | 21 | A05-216 | NTC |
| 11 | A05-216 | Canola event Ms8 | | | |

TABLE 48

Gel lanes showing the amplicons from assay A05-216 with seven soybean, seven maize and five cotton Certified Reference Materials (4 GM and 1 regular cotton materials), as shown in FIG. 27B

| Lane | Assay | Sample | Lane | Assay | Sample |
|---|---|---|---|---|---|
| 1 | DNA ladder | DNA ladder | 13 | A05-216 | Maize event MON89034 |
| 2 | A05-216 | Event Positive control | 14 | A05-216 | Maize event MIR604 |
| 3 | A05-216 | 100% DHA Positive | 15 | A05-216 | Maize event MON88017 |
| 4 | A05-216 | AV Jade (DHA negative) | 16 | A05-216 | Maize event MON87427 |
| 5 | A05-216 | Soybean event MON89788 | 17 | A05-216 | Maize event MON 87460 |
| 6 | A05-216 | Soybean event MON87769 | 18 | A05-216 | Maize event T25 |
| 7 | A05-216 | Soybean event MON87708 | 19 | A05-216 | Cotton event MON15985-7 |
| 8 | A05-216 | Soybean event MON87705 | 20 | A05-216 | Cotton event MON531 |
| 9 | A05-216 | Soybean event MON87701 | 21 | A05-216 | Cotton event MON1445 |
| 10 | A05-216 | Soybean event FG72 | 22 | A05-216 | Non-GM cotton 0306-A4 |
| 11 | A05-216 | Soybean event A5547-127 | 23 | A05-216 | Cotton event GHB614 |
| 12 | A05-216 | Maize event GA21 | 24 | A05-216 | NTC |

No amplicons of the qualitative event-specific Assay A05-216 were present in non-GM canola materials. More specifically, the qualitative event-specific Assay A05-216 was also validated with eight non-GM conventional canola varieties. Seven were selected from Nuseed germplasm pool with various genetic backgrounds (FIG. 24) and one was ordered from AOCS. The results showed A05-216 assay did not amplify any amplicons from these 8 non-GM conventional canola varieties.

The event specific assay A05-216 was tested with NS-B50027-4 event line DNA at six different spike levels and sensitivity (%) was calculated based on 16 replicates at 0.05% spike level. All samples containing event NS-B50027-4 DNA from 50% to 0.05% (0.05% equals to 43.4 genome copies for NS-B50027-4, see Table 40) showed the expected amplicons consistently from A05-216 assay. So, the Limit of Detection (LOD) is at least 0.05% NS-B50027-4 DNA to total DNA or less than 50 genome copies.

The event specific assay A05-216 was also tested with 25 commercially available GM events from AOCS and 8 different non-GM conventional oilseeds (*Brassica napus*) varieties. The results showed the assay can amplify the expected amplicons only from NS-B50027-4. The event specific assay A05-216 can specifically detect the DNA of DHA canola.

The HMG reference gene PCR profile was designed as internal control, all oilseed samples tested showed the expected 206 bp amplicon in the same lab setting and PCR condition.

Event-specific gel-based assay A05-216, targeting the insert in DHA canola NS-B50027-4 on chromosome A05, has been successfully developed and validated. The assay can be used for adventitious presence testing, trait purity testing, and trait introgression, and to support DHA Canola NS-B50027-4 regulatory submission and commercialization.

We claim:

1. A qualitative gel-based method of identifying the presence of a DHA canola NS-B50027-4 event or progeny thereof in a biological sample, said method comprising detecting a two event-specific detection method that comprises
   (a) extracting a DNA sample from said biological sample;
   (b) providing a first DNA primer pair combination, wherein said first DNA primer pair combination is selected from (i) nucleic acids as set forth in SEQ ID NO:3 (A05-286F) and SEQ ID NO:4 (A05-286R) or (ii) nucleic acids as set forth in SEQ NO:18 (A05-200F) and SEQ ID NO:19 (A05-200R), respectively;
   (c) providing a second DNA primer pair combination, wherein said second DNA primer pair combination is selected from (i) nucleic acids as set forth in SEQ ID NO:5 (A02-282F) and SEQ ID NO:6 (A02-282R) or (ii) nucleic acids as set forth in SEQ NO:20 (A02-258F) and SEQ ID NO:21 (A02-258R), respectively;
   (d) providing DNA amplification reaction conditions; and
   (e) performing two separate DNA amplification reactions with said first (as in step (b)) and second (as in step (c)) DNA primer pair combinations, thereby producing (1) an amplicon pair consisting of a 286-bp amplicon and a 282-bp amplicon, or (2) an amplicon pair consisting of a 200-bp amplicon and a 258-bp amplicon, respectively;
   wherein the presence of said amplicon pair (1) or (2) identifies the presence of the DHA canola NS-B50027-4 event or progeny thereof in the biological sample.

2. The method of claim 1, wherein the first DNA primer pair combination targets a transgenic junction region on chromosome A05.

3. The method of claim 1, wherein the second DNA primer pair combination targets a transgenic junction region on chromosome A02.

4. The method of claim 1, wherein said method is used for adventitious presence testing, low level presence testing, trait purity testing, trait introgression testing, or supporting plant stewardship of the DHA canola designated NS-B50027-4.

5. The method of claim 1, where said qualitative detection uses a polymerase chain reaction (PCR).

6. An event-specific quantitative detection method for identifying the presence of a DHA canola NS-B50027-4 event or progeny thereof in a biological sample, said method comprising a two event-specific detection method that comprises:
   (a) extracting a DNA sample from said biological sample;
   (b) providing a first DNA primer pair combination, wherein said first DNA primer pair combination consists of nucleotides as set forth in SEQ ID NO:12 (A05up2F) and SEQ ID NO:13 (A05up2R), respectively;
   (c) providing a second DNA primer pair combination, wherein said second DNA primer pair combination consists of nucleotides as set forth in SEQ ID NO:15 (A02dn2F) and SEQ ID NO:16 (A02dn2R), respectively;
   (d) providing DNA amplification reaction conditions; and
   (e) performing two separate DNA amplification reactions with said first and second DNA primer pair combinations, thereby producing a 120-bp amplicon and a 170-bp amplicon, respectively, wherein the presence of said 120-bp amplicon and 170-bp amplicon identifies the presence of the DHA canola NS-B50027-4 event or progeny thereof in the biological sample.

7. The method of claim 6, wherein the first DNA primer pair combination targets a transgenic junction region on chromosome A05.

8. The method of claim 6, wherein the second DNA primer pair combination targets a transgenic junction region on chromosome A02.

9. The method of claim 6, wherein said 120-bp amplicon is detected using an FAM-labeled probe having a sequence as set forth in SEQ ID NO:14 (A05up2P).

10. The method of claim 6, wherein said 170-bp amplicon is detected using an FAM-labeled probe having a sequence as set forth in SEQ ID NO:17 (A02dn2P).

11. The method of claim 6, wherein said quantitative detection is carried out using a Taqman assay.

12. The method of claim 6, wherein said method is for adventitious presence testing, low level presence testing, trait purity testing, trait introgression, or supporting plant stewardship of DHA canola NS-B50027-4.

13. A qualitative gel-based method of identifying the presence of a DHA canola NS-B50027-4 event or progeny thereof in a biological sample, said method comprising detecting a two event-specific detection method that comprises
   (a) extracting a DNA sample from said biological sample;
   (b) providing a first DNA primer pair combination, wherein said first DNA primer pair combination is from nucleotides as set forth in SEQ ID NO:28 (A05-216F) and SEQ ID NO:29 (A05-216R);
   (c) providing a second DNA primer pair combination, wherein said second DNA primer pair combination is from nucleotides as set forth in SEQ ID NO:20 (A02-258F) and SEQ ID NO:21 (A02-258R);
   (d) providing DNA amplification reaction conditions; and
   (e) performing two separate DNA amplification reactions with said first (as in step (b)) and second (as in step (c)) DNA primer pair combinations, thereby producing an amplicon pair consisting of a 216-bp amplicon and a 258-bp amplicon, respectively;
   wherein the presence of said amplicon pair identifies the presence of the DHA canola NS-B50027-4 event or progeny thereof in the biological sample.

14. The method of claim 13, wherein the first DNA primer pair combination targets a transgenic junction region on chromosome A05.

15. The method of claim 13, wherein the second DNA primer pair combination targets a transgenic junction region on chromosome A02.

16. The method of claim 13, wherein said method is used for adventitious presence testing, low level presence testing, trait purity testing, trait introgression testing, or supporting plant stewardship of the DHA canola designated NS-B50027-4.

17. The method of claim 13, where said qualitative detection uses a polymerase chain reaction (PCR).

* * * * *

SEQUENCE LISTING

<160> NUMBER OF SEQ ID NOS: 30

<210> SEQ ID NO 1
<211> LENGTH: 15
<212> TYPE: DNA
<213> ORGANISM: Artificial Sequence
<220> FEATURE:
<223> OTHER INFORMATION: B. napus fragment of A02 replaced by transgenic insert

<400> SEQUENCE: 1
gtagcacgac aagtt     15

<210> SEQ ID NO 2
<211> LENGTH: 20

```
<212> TYPE: DNA
<213> ORGANISM: Artificial Sequence
<220> FEATURE:
<223> OTHER INFORMATION: B. napus fragment of A05 replaced by transgenic
      insert

<400> SEQUENCE: 2
cacggtggag gtcaccatgt                                              20

<210> SEQ ID NO 3
<211> LENGTH: 24
<212> TYPE: DNA
<213> ORGANISM: Artificial Sequence
<220> FEATURE:
<223> OTHER INFORMATION: Forward primer for junction of T-DNA insert on
      chromosome A05 (A05-286F)

<400> SEQUENCE: 3
gaacaacaag gaacagagca acgt                                         24

<210> SEQ ID NO 4
<211> LENGTH: 24
<212> TYPE: DNA
<213> ORGANISM: Artificial Sequence
<220> FEATURE:
<223> OTHER INFORMATION: Reverse primer for junction of T-DNA insert on
      on chromosome A05 (A05-286R)

<400> SEQUENCE: 4
gacaatctgc tagtggatct ccca                                         24

<210> SEQ ID NO 5
<211> LENGTH: 20
<212> TYPE: DNA
<213> ORGANISM: Artificial Sequence
<220> FEATURE:
<223> OTHER INFORMATION: Forward primer for junction of T-DNA insert on
      on chromosome A02 (A05-282F)

<400> SEQUENCE: 5
cagatcttcc aaggcctcgt                                              20

<210> SEQ ID NO 6
<211> LENGTH: 23
<212> TYPE: DNA
<213> ORGANISM: Artificial Sequence
<220> FEATURE:
<223> OTHER INFORMATION: Reverse primer for junction of T-DNA insert on
      chromosome A02 (A05-282R)

<400> SEQUENCE: 6
cgctcttata ctgcactggt tag                                          23

<210> SEQ ID NO 7
<211> LENGTH: 22
<212> TYPE: DNA
<213> ORGANISM: Artificial Sequence
<220> FEATURE:
<223> OTHER INFORMATION: Forward primer for internal reference gene HMG
      (hmg99F; control)

<400> SEQUENCE: 7
ggtcgtcctc ctaaggcgaa ag                                           22

<210> SEQ ID NO 8
<211> LENGTH: 20
<212> TYPE: DNA
```

```
-continued

<213> ORGANISM: Artificial Sequence
<220> FEATURE:
<223> OTHER INFORMATION: Reverse primer for internal reference gene HMG
      (hmg99R; control)

<400> SEQUENCE: 8
cttcttcggc ggtcgtccac                                              20

<210> SEQ ID NO 9
<211> LENGTH: 189
<212> TYPE: DNA
<213> ORGANISM: Artificial Sequence
<220> FEATURE:
<223> OTHER INFORMATION: A02 genomic/transgene junction sequence used to
      design primers

<400> SEQUENCE: 9
ctccgccgcc aacaaggctt gtagttaata ggaatcattc agggattgtg attccgggca    60
gtagtaatta ataatatagt attagtatac agaacctctt atttagctaa aagattatgt   120
tcttaatgtt gataagaagt tgagaaaca aatataattg agcttctgat tagttgatcg    180
taattggtc                                                          189

<210> SEQ ID NO 10
<211> LENGTH: 226
<212> TYPE: DNA
<213> ORGANISM: Artificial Sequence
<220> FEATURE:
<223> OTHER INFORMATION: A05 genomic/transgene junction sequence used to
      design primers

<400> SEQUENCE: 10
ttttcgtcga gttgctgaaa ctggacccaa gccagtgtac ggcgcaggag gtactttaag    60
cttataaccc tttgtctatc ctttggctag cggctaatgt tgatgaactt ttttattcaa   120
ccgttggcta aggtaacact gatagtttaa actgaaggcg ggaaacgaca atctgctagt   180
ggatctccca gtcacgacgt tgtaaaacgg gcgccccgcg gaaagc                  226

<210> SEQ ID NO 11
<211> LENGTH: 24
<212> TYPE: DNA
<213> ORGANISM: Artificial Sequence
<220> FEATURE:
<223> OTHER INFORMATION: Reference probe sequence for quantitative
      detection (hmg-P)

<400> SEQUENCE: 11
cggagccact cggtgccgca actt                                          24

<210> SEQ ID NO 12
<211> LENGTH: 20
<212> TYPE: DNA
<213> ORGANISM: Artificial Sequence
<220> FEATURE:
<223> OTHER INFORMATION: Forward primer for A05up2 assay (A05up2F)

<400> SEQUENCE: 12
tctatccttt ggctagcggc                                              20

<210> SEQ ID NO 13
<211> LENGTH: 21
<212> TYPE: DNA
<213> ORGANISM: Artificial Sequence
<220> FEATURE:
<223> OTHER INFORMATION: Reverse primer for A05up2 assay (A05up2R)
```

```
<400> SEQUENCE: 13
tgactgggag atccactagc a                                              21

<210> SEQ ID NO 14
<211> LENGTH: 25
<212> TYPE: DNA
<213> ORGANISM: Artificial Sequence
<220> FEATURE:
<223> OTHER INFORMATION: Probe sequence for A05up2 assay (A05up2P)

<400> SEQUENCE: 14
caaccgttgg ctaaggtaac actga                                          25

<210> SEQ ID NO 15
<211> LENGTH: 26
<212> TYPE: DNA
<213> ORGANISM: Artificial Sequence
<220> FEATURE:
<223> OTHER INFORMATION: Forward primer for A02dn2 assay (A02dn2F)

<400> SEQUENCE: 15
acaaggcttg tagttaatag gaatca                                         26

<210> SEQ ID NO 16
<211> LENGTH: 26
<212> TYPE: DNA
<213> ORGANISM: Artificial Sequence
<220> FEATURE:
<223> OTHER INFORMATION: Reverse primer for A02dn2 assay (A02dn2R)

<400> SEQUENCE: 16
acgatcaact aatcagaagc tcaatt                                         26

<210> SEQ ID NO 17
<211> LENGTH: 22
<212> TYPE: DNA
<213> ORGANISM: Artificial Sequence
<220> FEATURE:
<223> OTHER INFORMATION: Probe sequence for A02dn2 assay (A02dn2P)

<400> SEQUENCE: 17
tcagggattg tgattccggg ca                                             22

<210> SEQ ID NO 18
<211> LENGTH: 20
<212> TYPE: DNA
<213> ORGANISM: Artificial Sequence
<220> FEATURE:
<223> OTHER INFORMATION: Forward primer for junction between T-DNA and
      genomic DNA on Chromosome A05 (A05-200F)

<400> SEQUENCE: 18
tgttgtggtg gtgacgattt                                                20

<210> SEQ ID NO 19
<211> LENGTH: 21
<212> TYPE: DNA
<213> ORGANISM: Artificial Sequence
<220> FEATURE:
<223> OTHER INFORMATION: Reverse primer for junction between T-DNA and
      genomic DNA on Chromosome A05 (A05-200R)

<400> SEQUENCE: 19
tccactagca gattgtcgtt t                                              21
```

<210> SEQ ID NO 20
<211> LENGTH: 21
<212> TYPE: DNA
<213> ORGANISM: Artificial Sequence
<220> FEATURE:
<223> OTHER INFORMATION: Forward primer for junction between T-DNA and
      genomic DNA on Chromosome A02 (A02-258F)

<400> SEQUENCE: 20
cattgagcag tgaacaccaa g                                           21

<210> SEQ ID NO 21
<211> LENGTH: 27
<212> TYPE: DNA
<213> ORGANISM: Artificial Sequence
<220> FEATURE:
<223> OTHER INFORMATION: Reverse primer for junction between T-DNA and
      genomic DNA on Chromosome A02 (A02-258R)

<400> SEQUENCE: 21
cagtttaaac tatcagtgtt tgaacac                                     27

<210> SEQ ID NO 22
<211> LENGTH: 18
<212> TYPE: DNA
<213> ORGANISM: Artificial Sequence
<220> FEATURE:
<223> OTHER INFORMATION: Forward primer for internal reference gene HMG
      as control (Hmg206F)

<400> SEQUENCE: 22
tccttccgtt tcctcgcc                                               18

<210> SEQ ID NO 23
<211> LENGTH: 18
<212> TYPE: DNA
<213> ORGANISM: Artificial Sequence
<220> FEATURE:
<223> OTHER INFORMATION: Reverse primer for internal reference gene HMG
      as control (Hmg206R)

<400> SEQUENCE: 23
ttccacgccc tctccgct                                               18

<210> SEQ ID NO 24
<211> LENGTH: 320
<212> TYPE: DNA
<213> ORGANISM: Artificial Sequence
<220> FEATURE:
<223> OTHER INFORMATION: Transgene junction region of NS-B50027-4
      chromosome A02 for assay A02-282

<400> SEQUENCE: 24
ctgattctgc ccgttcgact cagatcttcc aaggcctcgt ctccgagtcc gctgcttctc    60
gccgcgccga tcacttctcc gccgccaaca aggcttgtag ttaataggaa tcattcaggg   120
attgtgattc cgggcagtag taattaataa tatagtatta gtatacagaa cctcttattt   180
agctaaaaga ttatgttctt aatgttgata agaagtttga gaaacaaata taattgagct   240
tctgattagt tgatcgtaat tggtcattaa taattgtatc taaccagtgc agtataagag   300
cgtataagag catcttcaaa                                              320

<210> SEQ ID NO 25
<211> LENGTH: 380
<212> TYPE: DNA

<213> ORGANISM: Artificial Sequence
<220> FEATURE:
<223> OTHER INFORMATION: Transgene junction region of NS-B50027-4 chromosome A05 for assay A05-286

<400> SEQUENCE: 25

```
tttctttacc caaatctagt tcttgagagg atgaagcatc accgaacagt tctgcaacta      60
tccctcaaaa gctttaaaat gaacaacaag gaacagagca acgttccaaa gatcccaaac     120
gaaacatatt atctatacta atactatatt attaattact actgcccgga atcacaatcc     180
ctgaatgatt cctattaact acaagccttg ttggcggcgg agaagtgatc ggcgcggcga     240
gaagcagcgg actcggagac gaggccttgg aagatctgag tcgaacgggc ggtaccgcgg     300
gcccgtttta caacgtcgtg actgggagat ccactagcag attgtcgttt cccgccttca     360
gtttaaacta tcagtgtttg                                                 380
```

<210> SEQ ID NO 26
<211> LENGTH: 480
<212> TYPE: DNA
<213> ORGANISM: Artificial Sequence
<220> FEATURE:
<223> OTHER INFORMATION: Transgene junction region of NS-B50027-4 chromosome A02 for assay A02-258

<400> SEQUENCE: 26

```
ctacgatggt actcaatgcg gctaaggatt gatgaagatg gagatgttgc agatgagttc      60
ttggaagatg ataactgtaa gactttgccc agaaaatgca aaacaaaagc tgcaaaagtg     120
agaggtttag tgatatcttc tgatgggaaa cttcagccat taatgcattg agcagtgaac     180
accaaggata aatatttact gattagtgtg tgattgaatc aaagaaaggt tagaatctgg     240
ttttcattta gccattcaat ctcgatgtaa aatcggttag attctggttg ttgatacttg     300
agaacttgaa atgttttgta actgtgaatt tgttttgaa aatagacaag tgaatctgtt      360
tggggttgtg tgaaaacgtg tgagcaattg ttggaggtgt tcaaacactg atagtttaaa     420
ctgaaggcgg gaaacgacaa tctgctagtg gatctcccag tcacgacgtt gtaaaacggg     480
```

<210> SEQ ID NO 27
<211> LENGTH: 640
<212> TYPE: DNA
<213> ORGANISM: Artificial Sequence
<220> FEATURE:
<223> OTHER INFORMATION: Transgene junction region of NS-B50027-4 chromosome A05 for assay A05-200

<400> SEQUENCE: 27

```
taatcatgga ggagaagaag gatttttata accatgtctc tgttgcttgc tgcttaaacc      60
ctatataatt ggaaactttt tgttttagtc tgtgtctgaa agtttctata ttcgtattgt     120
ctattttgta aagactaaaa caaaaatgcc tattttagt ttgttcttgt tccgcaacac      180
cgttactgaa ctcttcgttc acttaaacag tttgtgtgtg tgagaaacag cgtaatgagc     240
tgctttggtt gttgtggtgg tgacgatttt cgtcgagttg ctgaaactgg acccaagcca     300
gtgtacggcg caggaggtac tttaagctta taacccttg tctatccttt ggctagcggc      360
taatgttgat gaacttttt attcaaccgt tggctaaggt aacactgata gtttaaactg     420
aaggcgggaa acgacaatct gctagtggat ctcccagtca cgacgttgta aaacgggcgc     480
cccgcggaaa gcttgcggcc gcggtaccgc ccgttcgact cagatcttcc aaggcctcgt     540
ctccgagtcc gctgcttctc gccgcgccga tcacttctcc gccgccaaca aggcttgtag     600
```

```
ttaataggaa tcattcaggg attgtgattc cgggcagtag              640
```

<210> SEQ ID NO 28
<211> LENGTH: 21
<212> TYPE: DNA
<213> ORGANISM: Artificial Sequence
<220> FEATURE:
<223> OTHER INFORMATION: Forward primer for A05-216 assay (A05-216F)

<400> SEQUENCE: 28

```
agattgtcgt ttcccgcctt c                                   21
```

<210> SEQ ID NO 29
<211> LENGTH: 19
<212> TYPE: DNA
<213> ORGANISM: Artificial Sequence
<220> FEATURE:
<223> OTHER INFORMATION: Reverse primer for A05-216 assay (A05-216R)

<400> SEQUENCE: 29

```
gctgccttgc cgcttctaa                                      19
```

<210> SEQ ID NO 30
<211> LENGTH: 399
<212> TYPE: DNA
<213> ORGANISM: Artificial Sequence
<220> FEATURE:
<223> OTHER INFORMATION: Transgene junction region of NS-B50027-4
      chromosome A05 for assay A05-216

<400> SEQUENCE: 30

```
acaagccttg ttggcggcgg agaagtgatc ggcgcggcga gaagcagcgg actcggagac    60
gaggccttgg aagatctgag tcgaacgggc ggtaccgcgg ccgcaagctt tccgcggggc   120
gcccgtttta caacgtcgtg actgggagat ccactagcag attgtcgttt cccgccttca   180
gtttaaacta tcagtgtttg aaggacagac ccacccaaga acacaccagt cattcagatg   240
cagcctatct ccgtgccggc tattccagct gagagttgaa ggatataact gataactatg   300
gttccaagtc cttgattggt gagggctctt atggaagagt gttttacggt gttcttagaa   360
gcggcaaggc agctgccatt aagaagctgg attctagta                          399
```